(12) United States Patent
Brzostowicz et al.

(10) Patent No.: US 6,790,645 B2
(45) Date of Patent: Sep. 14, 2004

(54) OXIDATION OF A CYCLOHEXANONE DERIVATIVE USING A BREVIBACTERIUM CYCLOHEXANONE MONOOXYGENASE

(75) Inventors: Patricia C. Brzostowicz, West Chester, PA (US); Pierre E. Rouviere, Wilmington, DE (US)

(73) Assignee: E. I. du Pont de Nemours and Company, Wilmington, DE (US)

(*) Notice: Subject to any disclaimer, the term of this patent is extended or adjusted under 35 U.S.C. 154(b) by 142 days.

(21) Appl. No.: 10/230,562

(22) Filed: Aug. 29, 2002

(65) Prior Publication Data

US 2003/0113886 A1 Jun. 19, 2003

Related U.S. Application Data

(62) Division of application No. 09/954,314, filed on Sep. 17, 2001, now Pat. No. 6,465,224, which is a division of application No. 09/504,358, filed on Feb. 15, 2000, now Pat. No. 6,365,376.
(60) Provisional application No. 60/120,702, filed on Feb. 19, 1999.

(51) Int. Cl.$^7$ .............................. C12N 9/02; C07H 21/04
(52) U.S. Cl. ....................................... 435/189; 536/23.2
(58) Field of Search ........................... 435/189; 536/23.2

(56) References Cited

U.S. PATENT DOCUMENTS 4,400,468 A    8/1983  Faber .......................... 435/142

FOREIGN PATENT DOCUMENTS

| AU | 669951 | 7/1995 |
| CA | 2103616 | 2/1994 |
| DE | 2140133 | 2/1973 |
| JP | 49043156 B4 | 11/1974 |
| JP | 61128890 A | 6/1986 |
| JP | 01023894 | 1/1989 |
| JP | 01023895 | 1/1989 |
| WO | WO9507996 | 3/1995 |

OTHER PUBLICATIONS

Brzostowicz et al. (May 2002) Identification of two gene clusters involved in cyclohexanone oxidation in *Brevibacterium epidermidis* strain HCU. Applied microbiology and biotechnology, 58 (6), 781–9.*
Brzostowicz et al. (Aug. 2000) Simultaneous identification of two cyclohexanone oxidation genes from an environmental Brevibacterium isolate using mRNA differential display. Journal of bacteriology, 182 (15) 4241–8.*
John Frost, Chem. Engg. (Rugby, Engl.) Renewable feedstocks; 611, 32–35, 1996.
Alexander Steinbuechel, CLB Chem. Labor Biotech., Microorganisms for Manufacturing polymers; 56(6), 277–8, 1995.
Draths et al., ACS Symp. Ser. , *Benign by Design*, 32–45, 1994 Microbial Biocatalysis, Chapter 3.
Takeshi et al., Bio. Ind. 8(10), 671–8,1991 (Abstract).
Hasegawa et al., Biosci., Biotechnol., Biochem., The Metabolism of Cyclohexal by *Exophiala jeanselmei*; 56(8), 1319–20, 1992.
Yoshizako et al., J. Ferment. Bioeng. Metabolism of n–Alkylcyclohexanes with an Even No. of Carbon Atoms in the Side Chain by Micrococcus sp. RCO–4M; 67(5), 335–8, 1989.
Kim et al., Sanop Misaengmul Hakhoechi, 13(1), 71–7, 1985; Utilization of Cyclohexanol and Characterization of Acinetobacter Calcoaceticus C–15.
Donoghue et al., Eur. J. Biochem The Metabolism of Cyclohexanol by Acinetobacter NCIB 9871; 60(1), 1–7, 1975.
Tanaka et al., Hakko Kogaku Kaishi, Metabolism of cyclohexanol by Pseudomonas sp.;55(2), 62–7, 1977.
Chen et al., J. Bacteriol., Acinetobacter Cycohexanone Monooxygenase: Gene Cloning and Sequence Determinaton; 170(2), 781–789, 1988.
A. Stevens et al. Genes Involved in Production of Plasmid–like Forms by a Bacteroides Conjugal Chromosomal Element Share Amino Acid Homology with Two–Component Regulatory Systems; J. Bacteriol. 174(9), 2935–2942 (1992).
Redenbach et al, Mol. Microbiol. 21 (1), 77–96 (1996).
G.E.deVries et al. CloningExpression, and Sequence Analysis of the *Bacillus methanolicus* C1 Methanol Dehydrogenase Gene; J. Bacteriol. vol. 174 (16), 5346–5353.
H–P.Klenk et al. Nature; vol. 390, The Complete Genome Sequence of the Hyperthermophilic, Sulphate–reducing Archaeon *Archaeoglobus fulgidus*, 364–370 (1997).
K. Nelson et al. Evidence for Lateral Gene Transfer between Archaea and Bacteria from Genome Sequence of *Thermotoga maritima*; Nature, vol. 399 323–329, (1999).
R. Cannio et al. Cloning and Overexpression in *Escherichia coli* of the Genes Enlcoding NAD–Dependent Alchol Dehydrogenase from Two Sulfolobus Species; J. Bacteriol. 178(1), 301–305 (1996).
Morii et al, J. Biochem. 126 (3), 624–631 (1999).
Robert J. Neal et al., Nucleotide Sequence Analysis Reveals Similarities between Proteins Determining Methlenomycin A Resistance in Streptomyces and Tetraycline Resistance in Eubacteria; Gene 58, 229–241 (1987).

* cited by examiner

*Primary Examiner*—Elizabeth Slobodyansky

(57) ABSTRACT

Two gene clusters have been isolated from an Brevibacterium sp HCU that encode the enzymes expected to convert cyclohexanol to adipic acid. Individual open reading frames (ORF's) on each gene cluster are useful for the production of intermediates in the adipic acid biosynthetic pathway or of related molecules. All the ORF's have been sequenced. Identification of gene function has been made on the basis of sequence comparison and biochemical analysis.

1 Claim, 8 Drawing Sheets

1: *E. coli*

2: *E. coli* expressing ORF 2.2

3: *Brevibacterium*

1, 3: *E. coli* expressing ORF 2.2

2, 4: *Brevibacterium* HCU 1, 2: *E. coli* expressing ORF 1.4
3, 4: *E. coli* expressing ORF 2.2
5: *E. coli*
6: *E. coli* expressing ORF 1.3 (control)

27

SEQUENCE LISTING

<160> NUMBER OF SEQ ID NOS: 49

<210> SEQ ID NO 1
<211> LENGTH: 1377
<212> TYPE: DNA
<213> ORGANISM: Brevibacterium sp HCU

<400> SEQUENCE: 1

```
atgatcgggc caagaacaca tttgactgct gtagatactg aacgcggttc agacctatcc    60
gaagaggctg tgggaacgaa tggattgggc accgcactta ccactggctc gggaatccaa   120
atccgtggcg ccgaacacta tgcacacttt tacgccaatg ctgtgtgcac aggtgaacca   180
gtcctacatc ccgagtcggg tcagggcctt ggagcgattg tgctctccgg tgacgaaagt   240
cgtcactcta acttactcct cccgttgctc cgaggcctcg tcgcacgaat gcagctgaaa   300
atccttcgta atccggacga cttcaacttc agttcgttgc ccaccatcgg cgactcaaaa   360
gcggccgacc aaccatacga cctattcatt cgtcagaca gagagcgaat caacacaggg    420
agcacgcact acccaagat gcgcgaccac actgccccag ttgttgggag tgtgtcggtt     480
gaaggactcg atgttgggtt cgcccgcgat cataatggtc tccatacgct cagacttttg   540
ggggatgcca catctgccca gtgctccat ggcgagacga actcctcaag aatcgttcgc    600
gacgaacgtt gggagggctg cttcgctgaa actgtgtccg ttttacgaag tcaacgatcc   660
atcgtgttgg tgggcgaggc tggagtaggc aaagcaactc tcgccgctct gggaatgaga   720
gccgtggatc ctcaccggcc gcttaacgag attgacgcag tacgagccaa gtggatggc    780 tgggacactg tccttcgatc gatcgctgag aatcttgacg ctggcaaagg actactcatc   840
cgtggagcag aagggctcac gagcagcgaa cgtacggaga ttcgatcact gttaaatgca   900
accgccgatc ccttcgtcgt cttgacagcc acaatcgact ttgacgatca atccacactt   960
acttcgaacg ccacagtcgc gccaactatt gtcattccac cactacgcca aaacccagaa  1020
cgtgtcgccc cctgtgggga cgccctcgcc gggccgggat ggcgacccgc aagactgacc  1080
gcccccgcgc ggaaagcact ttcccaatac atctggcccg ggaacctaag ggagcttcac  1140
cacattgccg caatgaccgt gcaaaacagt gctggctcag atattaccgt cgatatgctt  1200
cctgacaccg tccgatcagc accttcagga gcgacaatga tcgaaagagc ggaacggcac  1260
gcgctccttc aggctctcca acaagcagat ggaaatcggt ctcaggctgc agcaatcctc  1320
ggtgtctctc gggcaaccat ctatcgcaag attaagcaat acaaacttca ggaataa     1377
```

<210> SEQ ID NO 2
<211> LENGTH: 458
<212> TYPE: PRT
<213> ORGANISM: Brevibacterium sp HCU

<400> SEQUENCE: 2

```
Met Ile Gly Pro Arg Thr His Leu Thr Ala Val Asp Thr Glu Arg Gly
  1               5                  10                  15

Ser Asp Leu Ser Glu Glu Ala Val Gly Thr Asn Gly Leu Gly Thr Ala
             20                  25                  30

Leu Thr Thr Gly Ser Gly Ile Gln Ile Arg Gly Ala Glu His Tyr Ala
         35                  40                  45

His Phe Tyr Ala Asn Ala Val Cys Thr Gly Glu Pro Val Leu His Pro
     50                  55                  60

Glu Ser Gly Gln Gly Leu Gly Ala Ile Val Leu Ser Gly Asp Glu Ser
 65                  70                  75                  80

Arg His Ser Asn Leu Leu Pro Leu Leu Arg Gly Leu Val Ala Arg
                 85                  90                  95

Met Gln Leu Lys Ile Leu Arg Asn Pro Asp Asp Phe Asn Phe Ser Ser
            100                 105                 110

Leu Pro Thr Ile Gly Asp Ser Lys Ala Ala Asp Gln Pro Tyr Asp Leu
        115                 120                 125
```

```
Phe Ile Ser Ser Asp Arg Glu Arg Ile Asn Thr Gly Ser Thr His Leu
    130                 135                 140

Pro Lys Met Arg Asp His Thr Ala Pro Val Val Gly Ser Val Ser Val
145                 150                 155                 160

Glu Gly Leu Asp Val Gly Phe Ala Arg Asp His Asn Gly Leu His Thr
                165                 170                 175

Leu Arg Leu Leu Gly Asp Ala Thr Ser Ala Gln Val Leu His Gly Glu
            180                 185                 190

Thr Asn Ser Ser Arg Ile Val Arg Asp Glu Arg Trp Glu Gly Cys Phe
        195                 200                 205

Ala Glu Thr Val Ser Val Leu Arg Ser Gln Arg Ser Ile Val Leu Val
    210                 215                 220

Gly Glu Ala Gly Val Gly Lys Ala Thr Leu Ala Ala Leu Gly Met Arg
225                 230                 235                 240

Ala Val Asp Pro His Arg Pro Leu Asn Glu Ile Asp Ala Val Arg Ala
                245                 250                 255

Lys Val Asp Gly Trp Asp Thr Val Leu Arg Ser Ile Ala Glu Asn Leu
            260                 265                 270

Asp Ala Gly Lys Gly Leu Leu Ile Arg Gly Ala Glu Gly Leu Thr Ser
        275                 280                 285

Ser Glu Arg Thr Glu Ile Arg Ser Leu Leu Asn Ala Thr Ala Asp Pro
    290                 295                 300

Phe Val Val Leu Thr Ala Thr Ile Asp Phe Asp Asp Gln Ser Thr Leu
305                 310                 315                 320

Thr Ser Asn Ala Thr Val Ala Pro Thr Ile Val Pro Pro Leu Arg
                325                 330                 335

Gln Asn Pro Glu Arg Val Ala Pro Leu Trp Asp Ala Leu Ala Gly Pro
        340                 345                 350

Gly Trp Arg Pro Ala Arg Leu Thr Ala Pro Ala Arg Lys Ala Leu Ser
    355                 360                 365

Gln Tyr Ile Trp Pro Gly Asn Leu Arg Glu Leu His His Ile Ala Ala
370                 375                 380

Met Thr Val Gln Asn Ser Ala Gly Ser Asp Ile Thr Val Asp Met Leu
385                 390                 395                 400

Pro Asp Thr Val Arg Ser Ala Pro Ser Gly Ala Thr Met Ile Glu Arg
                405                 410                 415

Ala Glu Arg His Ala Leu Leu Gln Ala Leu Gln Gln Ala Asp Gly Asn
            420                 425                 430

Arg Ser Gln Ala Ala Ile Leu Gly Val Ser Arg Ala Thr Ile Tyr
        435                 440                 445

Arg Lys Ile Lys Gln Tyr Lys Leu Gln Glu
    450                 455

<210> SEQ ID NO 3
<211> LENGTH: 681
<212> TYPE: DNA
<213> ORGANISM: Brevibacterium sp HCU

<400> SEQUENCE: 3
atgtcattgc aacttatgag atgggtcttc gaagattggc agcgtgtaac aaaagaaccg    60
tcaaacgttc gctacgaaga gacaaccgaa ggcagcgttc caggcatctg ggtgctcccc   120
gacgaagcgg acgacgccaa gcccttcctg gttctccacg gtggaggctt cgcactgggc   180
tcgtcgaata gccatcgcaa attggccggc catctagcca agcaaagcgg cagacaagct   240
```

-continued

```
tttgtcgccg acttccgcct agcccccgaa cacccatttc cagcacagat agaagatgcg      300
ctcaccgtca tctccgcgat gaatagtcgg ggcatcccca ctgagaacat cacactggtc      360
ggcgacagcg caggagcgag catcgcgatc ggaactgttc tttcactgtt aaaagacgga      420
agagctctcc cccgacaggt cgtcaccatg tctccttggg tggatatgga aaactccggt      480
gagactatcg agtcaaacga cgcatacgac ttcctcatca cccgggatgg actacaggga      540
aacattgacc gctacctggc agtggagcgg atcctcgtga cgggactggt aaatccgcta      600
tacgcagatt ccatgggtt tccccgactg tacatctgcg ttagtgacac cgagtcctct       660
acgcggacag catccgtcta g                                                681
```

<210> SEQ ID NO 4
<211> LENGTH: 226
<212> TYPE: PRT
<213> ORGANISM: Brevibacterium sp HCU

<400> SEQUENCE: 4

```
Met Ser Leu Gln Leu Met Arg Trp Val Phe Glu Asp Trp Gln Arg Val
  1               5                  10                  15

Thr Lys Glu Pro Ser Asn Val Arg Tyr Glu Thr Thr Glu Gly Ser
             20                  25                  30

Val Pro Gly Ile Trp Val Leu Pro Asp Glu Ala Asp Ala Lys Pro
         35                  40                  45

Phe Leu Val Leu His Gly Gly Phe Ala Leu Gly Ser Ser Asn Ser
     50                  55                  60

His Arg Lys Leu Ala Gly His Leu Ala Lys Gln Ser Gly Arg Gln Ala
 65                  70                  75                  80

Phe Val Ala Asp Phe Arg Leu Ala Pro Glu His Pro Phe Pro Ala Gln
                 85                  90                  95

Ile Glu Asp Ala Leu Thr Val Ile Ser Ala Met Asn Ser Arg Gly Ile
            100                 105                 110

Pro Thr Glu Asn Ile Thr Leu Val Gly Asp Ser Ala Gly Ala Ser Ile
        115                 120                 125

Ala Ile Gly Thr Val Leu Ser Leu Leu Lys Asp Gly Arg Ala Leu Pro
    130                 135                 140

Arg Gln Val Val Thr Met Ser Pro Trp Val Asp Met Glu Asn Ser Gly
145                 150                 155                 160

Glu Thr Ile Glu Ser Asn Asp Ala Tyr Asp Phe Leu Ile Thr Arg Asp
                165                 170                 175

Gly Leu Gln Gly Asn Ile Asp Arg Tyr Leu Ala Val Glu Arg Ile Leu
            180                 185                 190

Val Thr Gly Leu Val Asn Pro Leu Tyr Ala Asp Phe His Gly Phe Pro
        195                 200                 205

Arg Leu Tyr Ile Cys Val Ser Asp Thr Glu Ser Ser Thr Arg Thr Ala
    210                 215                 220

Ser Val
225
```

<210> SEQ ID NO 5
<211> LENGTH: 1662
<212> TYPE: DNA
<213> ORGANISM: Brevibacterium sp HCU

<400> SEQUENCE: 5

```
atgccaatta cacaacaact tgaccacgac gctatcgtca tcggcgccgg cttctccgga      60
```

```
ctagccattc tgcaccacct gcgtgaaatc ggcctagaca ctcaaatcgt cgaagcaacc    120
gacggcattg gaggaacttg gtggatcaac cgctacccgg gggtgcggac cgacagcgag    180
ttccactact actctttcag cttcagcaag gaagttcgtg acgagtggac atggactcaa    240
cgctacccag acggtgaaga gtttgcgcc tatctcaatt tcattgctga tcgacttgat     300
cttcggaagg acattcagct caactcacga gtgaatactg cccgttggaa tgagacggaa    360
aagtactggg acgtcatttt cgaagacggg tcctcgaaac gcgctcgctt cctcatcagc    420
gcaatgggtg cacttagcca ggcgattttc ccggccatcg acggaatcga cgaattcaac    480
ggcgcgaaat atcacactgc ggcttggcca gctgatggcg tagatttcac gggcaagaag    540
gttggagtca ttgggttgg ggcctcggga attcaaatca ttcccgagct cgccaagttg    600
gctggcgaac tattcgtatt ccagcgaact ccgaactatg tggttgagag caacaacgac    660
aaagttgacg ccgagtggat gcagtacgtt cgcgacaact atgacgaaat tttcgaacgc    720
gcatccaagc acccgttcgg ggtcgatatg gagtatccga cggattccgc cgtcgaggtt    780
tcagaagaag aacgtaagcg agtctttgaa agcaaatggg aggagggagg cttccatttt    840
gcaaacgagt gtttcacgga cctgggtacc agtcctgagg ccagcgagct ggcgtcagag    900
ttcatacgtt cgaagattcg ggaggtcgtt aaggaccccg ctacggcaga tctcctttgt    960
cccaagtcgt actcgttcaa cggtaagcga gtgccgaccg gccacggcta ctacgagacg   1020
ttcaatcgca cgaatgtgca ccttttggat gccagggca ctccaattac tcggatcagc    1080
agcaaaggta tcgttcacgg agacaccgaa tacgaactag atgcaatcgt gttcgcaacc   1140
ggcttcgacg cgatgacagg tacgctcacc aacattgaca tcgtcggccg cgacggagtc   1200
atcctccgcg acaagtgggc ccaggatggg cttaggacaa acattggtct tactgtaaac   1260
ggcttcccga acttcctgat gtctcttgga cctcagaccc cgtactccaa ccttgttgtt   1320
cctattcagt tgggagccca atggatgcag cgattcctta agttcattca ggaacgcggc   1380
attgaagtgt tcgagtcgtc gagagaagct gaagaaatct ggaatgccga aaccattcgc   1440
ggcgctgaat ctacggtcat gtccatcgaa ggacccaaag ccggcgcatg gttcatcggc   1500
ggcaacattc ccggtaaatc acgtgagtac caggtgtata tgggcggcgg tcaggtctac   1560
caggactggt gccgcgaggc ggaagaatcc gactacgcca cttttctgaa tgctgactcc   1620
attgacggcg aaaaggttcg tgaatcggcg ggtatgaaat ag                      1662
```

<210> SEQ ID NO 6
<211> LENGTH: 553
<212> TYPE: PRT
<213> ORGANISM: Brevibacterium sp HCU

<400> SEQUENCE: 6

```
Met Pro Ile Thr Gln Gln Leu Asp His Asp Ala Ile Val Ile Gly Ala
  1               5                  10                  15

Gly Phe Ser Gly Leu Ala Ile Leu His His Leu Arg Glu Ile Gly Leu
                 20                  25                  30

Asp Thr Gln Ile Val Glu Ala Thr Asp Gly Ile Gly Gly Thr Trp Trp
             35                  40                  45

Ile Asn Arg Tyr Pro Gly Val Arg Thr Asp Ser Glu Phe His Tyr Tyr
         50                  55                  60

Ser Phe Ser Phe Ser Lys Glu Val Arg Asp Glu Trp Thr Trp Thr Gln
 65                  70                  75                  80

Arg Tyr Pro Asp Gly Glu Glu Val Cys Ala Tyr Leu Asn Phe Ile Ala
                 85                  90                  95
```

```
Asp Arg Leu Asp Leu Arg Lys Asp Ile Gln Leu Asn Ser Arg Val Asn
            100                 105                 110

Thr Ala Arg Trp Asn Glu Thr Glu Lys Tyr Trp Asp Val Ile Phe Glu
        115                 120                 125

Asp Gly Ser Ser Lys Arg Ala Arg Phe Leu Ile Ser Ala Met Gly Ala
        130                 135                 140

Leu Ser Gln Ala Ile Phe Pro Ala Ile Asp Gly Ile Asp Glu Phe Asn
145                 150                 155                 160

Gly Ala Lys Tyr His Thr Ala Ala Trp Pro Ala Asp Gly Val Asp Phe
                165                 170                 175

Thr Gly Lys Lys Val Gly Val Ile Gly Val Gly Ala Ser Gly Ile Gln
                180                 185                 190

Ile Ile Pro Glu Leu Ala Lys Leu Ala Gly Leu Phe Val Phe Gln
                195                 200                 205

Arg Thr Pro Asn Tyr Val Val Glu Ser Asn Asn Asp Lys Val Asp Ala
                210                 215                 220

Glu Trp Met Gln Tyr Val Arg Asp Asn Tyr Asp Glu Ile Phe Glu Arg
225                 230                 235                 240

Ala Ser Lys His Pro Phe Gly Val Asp Met Glu Tyr Pro Thr Asp Ser
                245                 250                 255

Ala Val Glu Val Ser Glu Glu Arg Lys Arg Val Phe Glu Ser Lys
                260                 265                 270

Trp Glu Glu Gly Gly Phe His Phe Ala Asn Glu Cys Phe Thr Asp Leu
                275                 280                 285

Gly Thr Ser Pro Glu Ala Ser Glu Leu Ala Ser Glu Phe Ile Arg Ser
    290                 295                 300

Lys Ile Arg Glu Val Val Lys Asp Pro Ala Thr Ala Asp Leu Leu Cys
305                 310                 315                 320

Pro Lys Ser Tyr Ser Phe Asn Gly Lys Arg Val Pro Thr Gly His Gly
                325                 330                 335

Tyr Tyr Glu Thr Phe Asn Arg Thr Asn Val His Leu Leu Asp Ala Arg
                340                 345                 350

Gly Thr Pro Ile Thr Arg Ile Ser Ser Lys Gly Ile Val His Gly Asp
    355                 360                 365

Thr Glu Tyr Glu Leu Asp Ala Ile Val Phe Ala Thr Gly Phe Asp Ala
        370                 375                 380

Met Thr Gly Thr Leu Thr Asn Ile Asp Ile Val Gly Arg Asp Gly Val
385                 390                 395                 400

Ile Leu Arg Asp Lys Trp Ala Gln Asp Gly Leu Arg Thr Asn Ile Gly
                405                 410                 415

Leu Thr Val Asn Gly Phe Pro Asn Phe Leu Met Ser Leu Gly Pro Gln
            420                 425                 430

Thr Pro Tyr Ser Asn Leu Val Val Pro Ile Gln Leu Gly Ala Gln Trp
        435                 440                 445

Met Gln Arg Phe Leu Lys Phe Ile Gln Glu Arg Gly Ile Glu Val Phe
450                 455                 460

Glu Ser Ser Arg Glu Ala Glu Glu Ile Trp Asn Ala Glu Thr Ile Arg
465                 470                 475                 480

Gly Ala Glu Ser Thr Val Met Ser Ile Glu Gly Pro Lys Ala Gly Ala
                485                 490                 495

Trp Phe Ile Gly Gly Asn Ile Pro Gly Lys Ser Arg Glu Tyr Gln Val
                500                 505                 510
```

```
Tyr Met Gly Gly Gln Val Tyr Gln Asp Trp Cys Arg Glu Ala Glu
        515                 520                 525

Glu Ser Asp Tyr Ala Thr Phe Leu Asn Ala Asp Ser Ile Asp Gly Glu
    530                 535                 540

Lys Val Arg Glu Ser Ala Gly Met Lys
545                 550

<210> SEQ ID NO 7
<211> LENGTH: 1245
<212> TYPE: DNA
<213> ORGANISM: Brevibacterium sp HCU

<400> SEQUENCE: 7
atggagtcgc acaacgaaaa cacacttggc ctcggattac tacgccaacc cggcactgta      60
gtgttcggcc cagggcagag acgtgagctc ccgtccatag ccaaacgtta cggttcgacc     120
gtattgatct gcaccgacga acgcatgctc gctgaaccaa tgtgtattga cttgcaaaca     180
gcgttggaaa aagcgggaat gcgtgtcgtt gtatacggaa atgtgcgtcc tgacttaccc     240
cgagccgaca ttcagactgc aacacggaaa cttgcccacg acaaaatcga tgtcatcttc     300
ggtcttggcg gaggaagctg catggacttc gcaaaggtta tggggatcct acttctgtcc     360
ccaggcgacg tccgtgacat cttcggcgaa acgtcgtctc cggcccaggg ttttacccgta     420
atcactgtgc ccaccactgg aggtaccggg gccgaggcga cttgtatttc agtggtgcac     480
gatgaggaaa aggcgtgaa ggttggggtc gcaagtgcct atatgcaggc tgtggccacc      540
gtcatcgatc cagagttcac gcttactgcc cagaggggc tgacggctgc gacggcgacg     600
gatgcactct cacatctggt ggagtcgtac accgcgtacg cgaaaaatcc ctcctcggac     660
gatattcggg atcaccttta tgtcggtaag aacctgctga cagacgtatg ggctgaacgt     720
gggctcaagc tcatttcgga cgggattcct gccctggcaa agatctcact gatctcaac     780
gcacgtacca atgtcatgct tgccgctttc tgcggcggga tgggaatcaa cactaccggc     840
acggcaggat gtcatgccct tcaatcaccg ctcagtgcgt tgactggaac atcgcacggc     900
ttcggggtgg gcgcgctgct tccttacgtg atgcggtaca acttaccagc tcgtacacca     960
gagtttgcac gtctcggtga gctagttggg gcggaccgtg aagcactgtt tttggaaagt    1020
gcccagcatg ccgtcgagaa agttaatggg ctagtgtcaa ctattgggc gcccacagat    1080
ttaggtgcct tggggatgac cgaggcggat gtggcgggcg tcgctaaagc gcagctgct    1140
tcaacccgtc tcatagccaa caaccccga cctttaccag ccgaaatcat ggaagaaatt    1200
ctgttgcggg gagttcgcgg agatagaagc tggtgggccg agtga                    1245

<210> SEQ ID NO 8
<211> LENGTH: 414
<212> TYPE: PRT
<213> ORGANISM: Brevibacterium sp HCU

<400> SEQUENCE: 8

Met Glu Ser His Asn Glu Asn Thr Leu Gly Leu Gly Leu Leu Arg Gln
  1               5                  10                  15

Pro Gly Thr Val Val Phe Gly Pro Gly Gln Arg Arg Glu Leu Pro Ser
                20                  25                  30

Ile Ala Lys Arg Tyr Gly Ser Thr Val Leu Ile Cys Thr Asp Glu Arg
            35                  40                  45

Met Leu Ala Glu Pro Met Cys Ile Asp Leu Gln Thr Ala Leu Glu Lys
        50                  55                  60
```

-continued

```
Ala Gly Met Arg Val Val Tyr Gly Asn Val Arg Pro Asp Leu Pro
 65                  70                  75                  80

Arg Ala Asp Ile Gln Thr Ala Thr Arg Lys Leu Ala His Asp Lys Ile
             85                  90                  95

Asp Val Ile Phe Gly Leu Gly Gly Ser Cys Met Asp Phe Ala Lys
            100                 105                 110

Val Met Gly Ile Leu Leu Ser Pro Gly Asp Val Arg Asp Ile Phe
            115                 120                 125

Gly Glu Asn Val Val Ser Gly Pro Gly Leu Pro Val Ile Thr Val Pro
130                 135                 140

Thr Thr Gly Gly Thr Gly Ala Glu Ala Thr Cys Ile Ser Val Val His
145                 150                 155                 160

Asp Glu Glu Lys Gly Val Lys Val Gly Val Ala Ser Ala Tyr Met Gln
                165                 170                 175

Ala Val Ala Thr Val Ile Asp Pro Glu Phe Thr Leu Thr Ala Pro Glu
            180                 185                 190

Gly Leu Thr Ala Ala Thr Ala Thr Asp Ala Leu Ser His Leu Val Glu
            195                 200                 205

Ser Tyr Thr Ala Tyr Ala Lys Asn Pro Ser Ser Asp Asp Ile Arg Asp
210                 215                 220

His Leu Tyr Val Gly Lys Asn Leu Leu Thr Asp Val Trp Ala Glu Arg
225                 230                 235                 240

Gly Leu Lys Leu Ile Ser Asp Gly Ile Pro Ala Leu Ala Lys Asp Leu
                245                 250                 255

Thr Asp Leu Asn Ala Arg Thr Asn Val Met Leu Ala Ala Phe Cys Gly
            260                 265                 270

Gly Met Gly Ile Asn Thr Thr Gly Thr Ala Gly Cys His Ala Leu Gln
            275                 280                 285

Ser Pro Leu Ser Ala Leu Thr Gly Thr Ser His Gly Phe Gly Val Gly
290                 295                 300

Ala Leu Leu Pro Tyr Val Met Arg Tyr Asn Leu Pro Ala Arg Thr Pro
305                 310                 315                 320

Glu Phe Ala Arg Leu Gly Glu Leu Val Gly Ala Asp Arg Gly Ser Thr
                325                 330                 335

Val Leu Glu Ser Ala Gln His Ala Val Glu Lys Val Glu Trp Leu Val
            340                 345                 350

Ser Thr Ile Gly Ala Pro Thr Asp Leu Gly Ala Leu Gly Met Thr Glu
            355                 360                 365

Ala Asp Val Ala Gly Val Ala Lys Ala Ala Ala Ser Thr Arg Leu
370                 375                 380

Ile Ala Asn Asn Pro Arg Pro Leu Pro Ala Glu Ile Met Glu Glu Ile
385                 390                 395                 400

Leu Leu Arg Gly Val Arg Gly Asp Arg Ser Trp Trp Ala Glu
                405                 410
```

<210> SEQ ID NO 9
<211> LENGTH: 951
<212> TYPE: DNA
<213> ORGANISM: Brevibacterium sp HCU

<400> SEQUENCE: 9

```
gtgggccgag tgagccacgt agggatttc ggcgctggct ctataggtac agcctttgcg      60
ctactgttcg ctgatgctgg cttcgctgtt cggatctttg atcctgatcc atcagctctg    120
gaacgatcaa gacatgtcat cgatcagcga atcacggaac ttcaacgatt caccttattg    180
```

```
gcatcgaatc caagtgaagt tcgtgagctc attgaaatcg tttcatctgc tcgaactgcg    240
gcatctggag caattcttgt ccaggaagca ggacctgaag atgtccagac taagcaacat    300
atatttgaag atctaactgc ggtcactagc gacgaaacga ttttggcgag tgcgtcctca    360
gcaattcctt cgagcagatt cgtagacgtt cattcagcgt ttcgatcgtt gattggccat    420
ccgggtaatc caccttactt gcttcgcgtg gttgaactag tgggtaatcc gtcgactgag    480
gagcagacca tattaagggc tggacagcta tatgagcagg ccggtctgtc cgctgtacgt    540
gtgaatcgag aggttgacgg gttcgtcttc aatcggatcc agggcgctgt acttcgtgaa    600
gcgtatgcgc tcgtcggagc tgagattata gatcctatgg acctagacac acttgttcaa    660
gatggtttag tcttcgctg tccgtcgcc ggcccgtttg cgacagttga tttgaacgta    720
cgtggtggga tcacagctca tgccgaacga atgggatctg cctatcaccg gatggccggc    780
gccttggaca cttccaaaga atggaccgac acgctggttg ccaaggtgaa ctgctctaga    840
cgcaaagccg tgcccctcga gcagtgggac caagctgtag ccgaccgaga tacgcaacta    900
atgaagcaat tgaacgcacg aacttctaac ggaggtacta cccgtgactg a            951
```

<210> SEQ ID NO 10
<211> LENGTH: 316
<212> TYPE: PRT
<213> ORGANISM: Brevibacterium sp HCU

<400> SEQUENCE: 10

```
Val Gly Arg Val Ser His Val Gly Ile Phe Gly Ala Gly Ser Ile Gly
  1               5                  10                  15

Thr Ala Phe Ala Leu Leu Phe Ala Asp Ala Gly Phe Ala Val Arg Ile
                 20                  25                  30

Phe Asp Pro Asp Pro Ser Ala Leu Glu Arg Ser Arg His Val Ile Asp
             35                  40                  45

Gln Arg Ile Thr Glu Leu Gln Arg Phe Thr Leu Leu Ala Ser Asn Pro
         50                  55                  60

Ser Glu Val Arg Glu Leu Ile Glu Ile Val Ser Ser Ala Arg Thr Ala
 65                  70                  75                  80

Ala Ser Gly Ala Ile Leu Val Gln Glu Ala Gly Pro Glu Asp Val Gln
                 85                  90                  95

Thr Lys Gln His Ile Phe Glu Asp Leu Thr Ala Val Thr Ser Asp Glu
            100                 105                 110

Thr Ile Leu Ala Ser Ala Ser Ala Ile Pro Ser Ser Arg Phe Val
            115                 120                 125

Asp Val His Ser Ala Phe Arg Ser Leu Ile Gly His Pro Gly Asn Pro
        130                 135                 140

Pro Tyr Leu Leu Arg Val Val Glu Leu Val Gly Asn Pro Ser Thr Glu
145                 150                 155                 160

Glu Gln Thr Ile Leu Arg Ala Gly Gln Leu Tyr Glu Gln Ala Gly Leu
                165                 170                 175

Ser Ala Val Arg Val Asn Arg Glu Val Asp Gly Phe Val Phe Asn Arg
            180                 185                 190

Ile Gln Gly Ala Val Leu Arg Glu Ala Tyr Ala Leu Val Gly Ala Glu
        195                 200                 205

Ile Ile Asp Pro Met Asp Leu Asp Thr Leu Val Gln Asp Gly Leu Gly
    210                 215                 220

Leu Arg Trp Ser Val Ala Gly Pro Phe Ala Thr Val Asp Leu Asn Val
225                 230                 235                 240
```

```
Arg Gly Gly Ile Thr Ala His Ala Glu Arg Met Gly Ser Ala Tyr His
              245                 250                 255

Arg Met Ala Gly Ala Leu Asp Thr Ser Lys Glu Trp Thr Asp Thr Leu
          260                 265                 270

Val Ala Lys Val Asn Cys Ser Arg Arg Lys Ala Val Pro Leu Glu Gln
      275                 280                 285

Trp Asp Gln Ala Val Ala Asp Arg Asp Thr Gln Leu Met Lys Gln Leu
  290                 295                 300

Asn Ala Arg Thr Ser Asn Gly Gly Thr Thr Arg Asp
305                 310                 315

<210> SEQ ID NO 11
<211> LENGTH: 777
<212> TYPE: DNA
<213> ORGANISM: Brevibacterium sp HCU

<400> SEQUENCE: 11
gtactacccg tgactgactc attaggtgga gacgtctttc tcgttactgg cggtgctggc        60
ggtatcggaa agccacgac gacggcactt gcagaacgtg gcggtcgggt ggtcttgacc       120
gatgttgatg aagacgctgg ctctcaagtc gccgacgaag tgcggcgcaa cactaacggt       180
gagattcgct ttgagccgtt ggatgtaaca acccccgcag cggttactga gtgcgcgcaa       240
aagctcgatg atgaaggttg gcccgtgtac ggcctcatgg ccaatgcggg tatcgcccca       300
agttcatcag cggtcgacta ctccgatgaa ctgtggcttc ggaccgtgga catcaacctc       360
aatggagtgt tctggtgctg ccgcgaattc ggaaagcgaa tgattgctcg aggtcgcggg       420
tcggtagtca ctacttcatc tattgcaggt ttccggactg tgtcgcccga gcgccacgca       480
gcgtatggag ccactaaggc cgcggtcgcc catcttgtcg ggctactcgg cgtcgagtgg       540
gcaaaaaccg gtgtgcgggt caacgcggtc gcaccgggct atacgcgaac accgatcctc       600
gaagctttga agccgaatc tcccgaaaca atcagcgaat ggactgaacg tatcccaaat       660
ggacgattga atgatccatc ggaaatcgcc gatggggtgg ttttcctcat gtcgaatgca       720
gccagaggca taactggaac ggtactgcac atcgacggtg gatacgctgc caggtag         777

<210> SEQ ID NO 12
<211> LENGTH: 258
<212> TYPE: PRT
<213> ORGANISM: Brevibacterium sp HCU

<400> SEQUENCE: 12

Val Leu Pro Val Thr Asp Ser Leu Gly Gly Asp Val Phe Leu Val Thr
  1               5                  10                  15

Gly Gly Ala Gly Gly Ile Gly Lys Ala Thr Thr Thr Ala Leu Ala Glu
              20                  25                  30

Arg Gly Gly Arg Val Val Leu Thr Asp Val Asp Glu Asp Ala Gly Ser
          35                  40                  45

Gln Val Ala Asp Glu Val Arg Arg Asn Thr Asn Gly Glu Ile Arg Phe
      50                  55                  60

Glu Pro Leu Asp Val Thr Asn Pro Ala Ala Val Thr Glu Cys Ala Gln
  65                  70                  75                  80

Lys Leu Asp Asp Glu Gly Trp Pro Val Tyr Gly Leu Met Ala Asn Ala
              85                  90                  95

Gly Ile Ala Pro Ser Ser Ser Ala Val Asp Tyr Ser Asp Glu Leu Trp
          100                 105                 110
```

Leu Arg Thr Val Asp Ile Asn Leu Asn Gly Val Phe Trp Cys Cys Arg
    115                 120                 125

Glu Phe Gly Lys Arg Met Ile Ala Arg Gly Arg Gly Ser Val Val Thr
130                 135                 140

Thr Ser Ser Ile Ala Gly Phe Arg Thr Val Ser Pro Glu Arg His Ala
145                 150                 155                 160

Ala Tyr Gly Ala Thr Lys Ala Ala Val Ala His Leu Val Gly Leu Leu
                165                 170                 175

Gly Val Glu Trp Ala Lys Thr Gly Val Arg Val Asn Ala Val Ala Pro
            180                 185                 190

Gly Tyr Thr Arg Thr Pro Ile Leu Glu Ala Leu Lys Ala Glu Ser Pro
        195                 200                 205

Glu Thr Ile Ser Glu Trp Thr Glu Arg Ile Pro Asn Gly Arg Leu Asn
    210                 215                 220

Asp Pro Ser Glu Ile Ala Asp Gly Val Val Phe Leu Met Ser Asn Ala
225                 230                 235                 240

Ala Arg Gly Ile Thr Gly Thr Val Leu His Ile Asp Gly Tyr Ala
                245                 250                 255

Ala Arg

<210> SEQ ID NO 13
<211> LENGTH: 771
<212> TYPE: DNA
<213> ORGANISM: Brevibacterium sp HCU

<400> SEQUENCE: 13
atgaatcgac tcggcggaaa agtagcagtc attactgggg gcgccgcagg catgggcgc      60
atacagtctg aactgtatgc gagtgagggt gcacaagtag cggtagtaga tgtcaatgaa    120
caagaaggcc gtgccactgc cgatgcgata agggccagcg gcggggttgc aaactattgg    180
aaattggacg tttctgacga gtctgaagtt gaaatagtcg tctccgacat tgccaagaga    240
ttcggtgcga ttaacgtact agtgaacaac gcaggcgtca ccggtgccga taaaccaact    300
cacgagatcg acgaacggga cctggacctc gtactgagcg tcgatgtgaa aggagtattc    360
ttcatgacaa acactgcat cccctacttt aaacaggctg gcggcggagc catcgtcaac    420
ttcgcgtcta tctatggtct ggtggggtcg caggagctta ccccgtacca cgcagccaaa    480
ggtgcggtcg ttgcccttac caaacaggac gcggtgactt acggaccgtc aaatatccga    540
gtgaatgcgg tagcacccgg aaccattttg actccactag tcaaggagct cggttcaagg    600
ggccccgatg gcttagatgg atatactaaa cttatgggtg ccaagcatcc gcttggtcgg    660
gtaggaaccc ccgaagaagt cgcggcagca acattgtttc tggcatccga agaagcttcg    720
ttcattactg gcgccgtcct tcccgttgac ggtggatata ctgcgcagtg a              771

<210> SEQ ID NO 14
<211> LENGTH: 256
<212> TYPE: PRT
<213> ORGANISM: Brevibacterium sp HCU

<400> SEQUENCE: 14

Met Asn Arg Leu Gly Gly Lys Val Ala Val Ile Thr Gly Gly Ala Ala
1               5                   10                  15

Gly Met Gly Arg Ile Gln Ser Glu Leu Tyr Ala Ser Glu Gly Ala Gln
            20                  25                  30

Val Ala Val Val Asp Val Asn Glu Gln Glu Gly Arg Ala Thr Ala Asp
        35                  40                  45

```
Ala Ile Arg Ala Ser Gly Gly Val Ala Asn Tyr Trp Lys Leu Asp Val
        50                  55                  60

Ser Asp Glu Ser Glu Val Glu Ile Val Val Ser Asp Ile Ala Lys Arg
 65                  70                  75                  80

Phe Gly Ala Ile Asn Val Leu Val Asn Asn Ala Gly Val Thr Gly Ala
                 85                  90                  95

Asp Lys Pro Thr His Glu Ile Asp Glu Arg Asp Leu Asp Leu Val Leu
            100                 105                 110

Ser Val Asp Val Lys Gly Val Phe Phe Met Thr Lys His Cys Ile Pro
115                 120                 125

Tyr Phe Lys Gln Ala Gly Gly Ala Ile Val Asn Phe Ala Ser Ile
        130                 135                 140

Tyr Gly Leu Val Gly Ser Gln Glu Leu Thr Pro Tyr His Ala Ala Lys
145                 150                 155                 160

Gly Ala Val Val Ala Leu Thr Lys Gln Asp Ala Val Thr Tyr Gly Pro
                165                 170                 175

Ser Asn Ile Arg Val Asn Ala Val Ala Pro Gly Thr Ile Leu Thr Pro
            180                 185                 190

Leu Val Lys Glu Leu Gly Ser Arg Gly Pro Asp Gly Leu Asp Gly Tyr
        195                 200                 205

Thr Lys Leu Met Gly Ala Lys His Pro Leu Gly Arg Val Gly Thr Pro
    210                 215                 220

Glu Glu Val Ala Ala Thr Leu Phe Leu Ala Ser Glu Glu Ala Ser
225                 230                 235                 240

Phe Ile Thr Gly Ala Val Leu Pro Val Asp Gly Gly Tyr Thr Ala Gln
                245                 250                 255

<210> SEQ ID NO 15
<211> LENGTH: 10629
<212> TYPE: DNA
<213> ORGANISM: Brevibacterium sp HCU

<400> SEQUENCE: 15
cttgcgacat ctgtacatca ttctcccacc agcgaaggtg gttgacgtta gggatgttcg      60
cattggatcc tgatgatctc caagaagcta agaaggctgt tctcgctgcc gtaggcagcc     120
acggtaaaca tgcaacaagt tgttggatt cttggggccg gtctcacttg agattcggcg     180
ctccagacgc cgtcaacgag gtaccacatg cgtccgatga cgagatcgac aatgctcttt     240
tcgacctctg tcgagatcag atccagtcat tcgctggtga acttgagggg tcgggccagg     300
gcattctttt gtctgatgca gcgggccgtg tggtagaaac ctggacaagc gatgatcggg     360
ccaagaacac atttgactgc tgtagatact gaacgcggtt cagacctatc cgaagaggct     420
gtgggaacga atggattggg caccgcactt accactggct cgggaatcca atccgtggc     480 gccgaacact atgcacactt ttacgccaat gctgtgtgca caggtgaacc agtcctacat     540
cccgagtcgg gtcagggcct tggagcgatt gtgctctccg gtgacgaaag tcgtcactct     600
aacttactcc tcccgttgct ccgaggcctc gtcgcacgaa tgcagctgaa atccttcgt      660 aatccggacg acttcaactt cagttcgttg cccaccatcg gcgactcaaa agcggccgac     720
caaccatacg acctattcat ttcgtcagac agagagcgaa tcaacacagg gagcacgcac     780
ttacccaaga tgcgcgacca cactgcccca gttgttggga gtgtgtcggt tgaaggactc     840
gatgttgggt tcgcccgcga tcataatggt ctccatacgc tcagactttt ggggatgcc      900 acatctgccc aagtgctcca tggcgagacg aactcctcaa gaatcgttcg cgacgaacgt     960
```

-continued

```
tgggagggct gcttcgctga aactgtgtcc gttttacgaa gtcaacgatc catcgtgttg    1020
gtgggcgagg ctggagtagg caaagcaact ctcgccgctc tgggaatgag agccgtggat    1080
cctcaccggc cgcttaacga gattgacgca gtacgagcca aagtggatgg ctgggacact    1140
gtccttcgat cgatcgctga gaatcttgac gctggcaaag gactactcat ccgtggagca    1200
gaagggctca cgagcagcga acgtacgagg attcgatcac tgttaaatgc aaccgccgat    1260
cccttcgtcg tcttgacagc cacaatcgac tttgacgatc aatccacact tacttcgaac    1320
gccacagtcg cgccaactat tgtcattcca ccactacgcc aaaacccaga acgtgtcgcc    1380
cccctgtggg acgccctcgc cgggccggga tggcgacccg caagactgac cgccccgcg    1440 cggaaagcac tttcccaata catctggccc gggaacctaa gggagcttca ccacattgcc    1500
gcaatgaccg tgcaaaacag tgctggctca gatattaccg tcgatatgct tcctgacacc    1560
gtccgatcag caccttcagg agcgacaatg atcgaaagag cggaacggca cgcgctcctt    1620
caggctctcc aacaagcaga tggaaatcgg tctcaggctg cagcaatcct cggtgtctct    1680
cgggcaacca tctatcgcaa gattaagcaa tacaaacttc aggaataaca ctctccgggc    1740
tccacacgaa gatgtatatt ctcgcttgcc catgacgtca tttaggtctg acaggtgcg    1800 caccgtcacg cttggagccg ggttcctgta cgagctcgcc acataatctg tgaagcttcc    1860
atcatgaaat cttctgcgcc tgcaaggcca ggaatgttcc gctgccgctc cgaaatagaa    1920
gtgatactta ctccgagtat gatcgggctt caccctccgt cgtaaataat tgcgtagtca    1980
tcgcggacgc aaacgttgtt acaccactgc ctccccgatc aacgcgtgcc accttggtgc    2040
taaagggccc cgtacgtgcc cagaataccc tcgtccaata ccgccacttt cttgcacagc    2100
accgaagatt tgcaaaaacc gttaagcgat ttcccgcgt atagattcag acgaattgtt    2160 ggagggctt tctacaaggt aactgagcag gtccactact tcaccggtgc tcgttggtcc    2220
gttgataacc ccggtcattc cgccattgga taagcgtgca cggccttcgg ctggccccac    2280
tctggactgt tgcaggaagt ggctagccaa ttgagtagcg acacgctcc gaagctcgat    2340 agtcgtcgag ttaaacactg gccctgcgcc aatacaccag cagcttctcc ggtgcccag    2400 aggacatcac caaccgattc ctttaacgcg aatgaaacct ccatcggaga gcatgtgggc    2460
cagggtccga cccctatgagc cgtcggcgcg tagcgacggt agagtttcct actgttcgcc    2520
agggtccgaa atgctcacga actaggtcac gccagactct gacaaccagg tatcggaaga    2580
cgatcccctc gacgcctgtt ctcgagcagt cggggcttct tccgggtatt cgaggacagc    2640
ggttccattc gcgtccattg gtctttgccg aagcctcagc gccgttgccg tgtagtccct    2700
tatccagcgt gtcagcccaa agacctcgga tagaggagac ataccctggc ttcgcggctc    2760
gaccactcgc ccgcggagtt atctcgtaag cttcgatcga gtgcgcggag actccgacct    2820
cctcgtctca gaaagtcggg gaacacagat tgttcgccgg atagacattg acaagatctc    2880
taccttgact cggacctcct gccactcacc ctccaacaat catgactaag cgtggcacca    2940
acgagagacc tggaccggaa agatccaca ttcgaagggg caaaacttcc acttgtgtct    3000
caaactgcga ctccgttgct tcaacctgag aatcgacttc ccatcggttc aacccccttg    3060
aacactggtt ccaacgactc attcgagtcc ctcggaacag tcagataagg aggtcacgtt    3120
gactgcgccc caccccacag acccacttgg cgagatttac gccgaatggg ataaggaatt    3180
tcgcgaacac cccaccatgt cattgcaact tatgagatgg gtcttcgaag attggcagcg    3240
tgtaacaaaa gaaccgtcaa acgttcgcta cgaagagaca accgaaggca gcgttccagg    3300
```

-continued

| | | | | |
|---|---|---|---|---|
| catctgggtg | ctccccgacg | aagcggacga | cgccaagccc | ttcctggttc tccacggtgg | 3360 |
| aggcttcgca | ctgggctcgt | cgaatagcca | tcgcaaattg | gccggccatc tagccaagca | 3420 |
| aagcggcaga | caagcttttg | tcgccgactt | ccgcctagcc | cccgaacacc catttccagc | 3480 |
| acagatagaa | gatgcgctca | ccgtcatctc | cgcgatgaat | agtcgggca tccccactga | 3540 |
| gaacatcaca | ctggtcggcg | acagcgcagg | agcgagcatc | gcgatcggaa ctgttctttc | 3600 |
| actgttaaaa | gacggaagag | ctctcccccg | acaggtcgtc | accatgtctc cttggtgga | 3660 |
| tatggaaaac | tccggtgaga | ctatcgagtc | aaacgacgca | tacgacttcc tcatcacccg | 3720 |
| ggatggacta | cagggaaaca | ttgaccgcta | cctggcagtg | gagcggatcc tcgtgacggg | 3780 |
| actggtaaat | ccgctatacg | cagatttcca | tgggtttccc | cgactgtaca tctgcgttag | 3840 |
| tgacaccgag | tcctctacgc | ggacagcatc | cgtctagccg | aacgtgcgaa gactgccaat | 3900 |
| gtcgacgtaa | cgctgtcggt | agaacaaggc | cagcaacacg | tgttccccat gcaagcaggc | 3960 |
| aaccaccctg | cagccgacaa | agcgatctcg | gaaatcgtcg | cttggtgcca ctgaaaacca | 4020 |
| aacaacatct | cttcaacgtt | gaaagatcga | ggaaccatgc | caattacaca caacttgac | 4080 |
| cacgacgcta | tcgtcatcgg | cgccggcttc | tccggactag | ccattctgca ccacctgcgt | 4140 |
| gaaatcggcc | tagacactca | aatcgtcgaa | gcaaccgacg | gcattggagg aacttggtgg | 4200 |
| atcaaccgct | acccgggggt | gcggaccgac | agcgagttcc | actactactc tttcagcttc | 4260 |
| agcaaggaag | ttcgtgacga | gtggacatgg | actcaacgct | acccagacgg tgaagaagtt | 4320 |
| tgcgcctatc | tcaatttcat | tgctgatcga | cttgatcttc | ggaaggacat tcagctcaac | 4380 |
| tcacgagtga | atactgcccg | ttggaatgag | acggaaaagt | actgggacgt cattttcgaa | 4440 |
| gacgggtcct | cgaaacgcgc | tcgcttcctc | atcagcgcaa | tgggtgcact tagccaggcg | 4500 |
| attttccccgg | ccatcgacgg | aatcgacgaa | ttcaacggcg | cgaaatatca cactgcggct | 4560 |
| tggccagctg | atggcgtaga | tttcacgggc | aagaaggttg | gagtcattgg ggttggggcc | 4620 |
| tcgggaattc | aaatcattcc | cgagctcgcc | aagttggctg | gcgaactatt cgtattccag | 4680 |
| cgaactccga | actatgtggt | tgagagcaac | aacgacaaag | ttgacgccga gtggatgcag | 4740 |
| tacgttcgcg | acaactatga | cgaaattttc | gaacgcgcat | ccaagcaccc gttcggggtc | 4800 |
| gatatggagt | atccgacgga | ttccgccgtc | gaggtttcag | aagaagaacg taagcgagtc | 4860 |
| tttgaaagca | aatgggagga | gggaggcttc | cattttgcaa | acgagtgttt cacggacctg | 4920 |
| ggtaccagtc | ctgaggccag | cgagctggcg | tcagagttca | tacgttcgaa gattcgggag | 4980 |
| gtcgttaagg | accccgctac | ggcagatctc | ctttgtccca | agtcgtactc gttcaacggt | 5040 |
| aagcgagtgc | cgaccggcca | cggctactac | gagacgttca | atcgcacgaa tgtgcaccCtt | 5100 |
| ttggatgcca | ggggcactcc | aattactcgg | atcagcagca | aaggtatcgt tcacggagac | 5160 |
| accgaatacg | aactagatgc | aatcgtgttc | gcaaccggct | tcgacgcgat gacaggtacg | 5220 |
| ctcaccaaca | ttgacatcgt | cggccgcgac | ggagtcatcc | tccgcgacaa gtgggcccag | 5280 |
| gatgggctta | ggacaaacat | tggtcttact | gtaaacggct | tcccgaactt cctgatgtct | 5340 |
| cttgacctc | agccccgta | ctccaacctt | gttgttccta | ttcagttggg agcccaatgg | 5400 |
| atgcagcgat | tccttaagtt | cattcaggaa | cgcggcattg | aagtgttcga gtcgtcgaga | 5460 |
| gaagctgaag | aaaatctggaa | tgccgaaacc | attcgcggcg | ctgaatctac ggtcatgtcc | 5520 |
| atcgaaggac | ccaaagccgg | cgcatggttc | atcggcggca | acattcccgg taaatcacgt | 5580 |
| gagtaccagg | tgtatatggg | cggcggtcag | gtctaccagg | actggtgccg cgaggcggaa | 5640 |
| gaatccgact | acgccacttt | tctgaatgct | gactccattg | acggcgaaaa ggttcgtgaa | 5700 |

-continued

```
tcggcgggta tgaaatagcc cagcagtctc gttcgggccc tcaccctgtg gccaagcccc    5760
acgtctcggc ggcaagctga tcgctcaaaa cacttgcagc cgcgtctgct cgaaaccgca    5820
atctttcaac caacgaagat ggtgaacatt tatggagtcg cacaacgaaa acacacttgg    5880
cctcggatta ctacgccaac ccggcactgt agtgttcggc ccagggcaga gacgtgagct    5940
cccgtccata gccaaacgtt acggttcgac cgtattgatc tgcaccgacg aacgcatgct    6000
cgctgaacca atgtgtattg acttgcaaac agcgttggaa aaagcgggaa tgcgtgtcgt    6060
tgtatacgga aatgtgcgtc ctgacttacc ccgagccgac attcagactg caacacggaa    6120
acttgcccac gacaaaatcg atgtcatctt cggtcttggc ggaggaagct gcatggactt    6180
cgcaaaggtt atggggatcc tacttctgtc cccaggcgac gtccgtgaca tcttcggcga    6240
aaacgtcgtc tccggccccg gtttacccgt aatcactgtg cccaccactg gaggtaccgg    6300
ggccgaggcg acttgtattt cagtggtgca cgatgaggaa aaaggcgtga aggttggggt    6360
cgcaagtgcc tatatgcagg ctgtggccac cgtcatcgat ccagagttca cgcttactgc    6420
cccgaggggg ctgacggctg cgacggcgac ggatgcactc tcacatctgg tggagtcgta    6480
caccgcgtac gcgaaaaatc cctcctcgga cgatattcgg gatcaccttt atgtcggtaa    6540
gaacctgctg acagacgtat gggctgaacg tgggctcaag ctcatttcgg acgggattcc    6600
tgccctggca aaagatctca ctgatctcaa cgcacgtacc aatgtcatgc ttgccgcttt    6660
ctgcggcggg atgggaatca acactaccgg cacggcagga tgtcatgccc ttcaatcacc    6720
gctcagtgcg ttgactggaa catcgcacgg cttcggggtg ggcgcgctgc ttccttacgt    6780
gatgcggtac aacttaccag ctcgtacacc agagtttgca cgtctcggtg agctagttgg    6840
ggcggaccgt ggaagcactg ttttggaaag tgcccagcat gccgtcgaga agttgaatg    6900 gctagtgtca actattgggg cgcccacaga tttaggtgcc ttggggatga ccgaggcgga    6960
tgtggcgggc gtcgctaaag ccgcagctgc ttcaacccgt tcatagcca acaaccccg     7020 accttttacca gccgaaatca tggaagaaat tctgttgcgg ggagttcgcg gagatagaag    7080
ctggtgggcc gagtgagcca cgtagggatt ttcggcgctg gctctatagg tacagccttt    7140
gcgctactgt tcgctgatgc tggcttcgct gttcggatct ttgatcctga tccatcagct    7200
ctggaacgat caagacatgt catcgatcag cgaatcacgg aacttcaacg attcaccttc    7260
ttggcatcga atccaagtga agttcgtgag ctcattgaaa tcgtttcatc tgctcgaact    7320
gcggcatctg gagcaattct tgtccaggaa gcaggacctg aagatgtcca gactaagcaa    7380
catatatttg aagatctaac tgcggtcact agcgacgaaa cgattttggc gagtgcgtcc    7440
tcagcaattc cttcgagcag attcgtagac gttcattcag cgtttcgatc gttgattggc    7500
catccgggta atccaccttc cttgcttcgc gtggttgaac tagtgggtaa tccgtcgact    7560
gaggagcaga ccatattaag ggctggacag ctatatgagc aggccggtct gtccgctgta    7620
cgtgtgaatc gagaggttga cgggttcgtc ttcaatcgga tccagggcgc tgtacttcgt    7680
gaagcgtatg cgctcgtcgg agctgagatt atagatccta tggacctaga cacacttgtt    7740
caagatggtt taggtcttcg ctggtccgtc gccggcccgt ttgcgacagt tgatttgaac    7800
gtacgtggtg ggatcacagc tcatgccgaa cgaatgggat ctgcctatca ccggatggcc    7860
ggcgccttgg acacttccaa agaatggacc gacacgctgg ttgccaaggt gaactgctct    7920
agacgcaaag ccgtgcccct cgagcagtgg gaccaagctg tagccgaccg agatacgcaa    7980
ctaatgaagc aattgaacgc acgaacttct aacggaggta ctacccgtga ctgactcatt    8040
```

```
aggtggagac gtctttctcg ttactggcgg tgctggcggt atcggaaaag ccacgacgac   8100
ggcacttgca gaacgtggcg gtcgggtggt cttgaccgat gttgatgaag acgctggctc   8160
tcaagtcgcc gacgaagtgc ggcgcaacac taacggtgag attcgctttg agccgttgga   8220
tgtaacaaac cccgcagcgg ttactgagtg cgcgcaaaag ctcgatgatg aaggttggcc   8280
cgtgtacggc ctcatggcca atgcgggtat cgccccaagt tcatcagcgg tcgactactc   8340
cgatgaactg tggcttcgga ccgtggacat caacctcaat ggagtgttct ggtgctgccg   8400
cgaattcgga aagcgaatga ttgctcgagg tcgcgggtcg gtagtcacta cttcatctat   8460
tgcaggtttc cggactgtgt cgcccagcgc ccacgcagcg tatggagcca ctaaggccgc   8520
ggtcgcccat cttgtcgggc tactcggcgt cgagtgggca aaaccggtg tgcgggtcaa    8580 cgcggtcgca ccgggctata cgcgaacacc gatcctcgaa gctttgaaag ccgaatctcc   8640
cgaaacaatc agcgaatgga ctgaacgtat cccaaatgga cgattgaatg atccatcgga   8700
aatcgccgat ggggtggttt tcctcatgtc gaatgcagcc agaggcataa ctggaacggt   8760
actgcacatc gacggtggat acgctgccag gtagagaaaa gagtcctcga tctactctgt   8820
ccgtccagca ccatcgtctg ggtccatcaa tacgtttatt tacttgtgac gcctcaatat   8880
caagattcag aatttgtaat tgtccaaccc cagaactcca cactggaatc cggacgatcg   8940
cttaattcac cgtactcttt cggcattcga attgaacagt gaataacgag attccactca   9000
aggcgagaga tagagcagag tcaccaattg cagctgcaag aattaggcat tttgtaattt   9060
cttattatga cacgaaaacc gtacacagta cacagaacaa tacaatttca acctgacatt   9120
gggagataac aatgaatcga ctcggcggaa aagtagcagt cattactggg ggcgccgcag   9180
gcatggggcg catacagtct gaactgtatg cgagtgaggg tgcacaagta gcggtagtag   9240
atgtcaatga acaagaaggc cgtgccactg ccgatgcgat aagggccagc ggcggggttg   9300
caaactattg gaaattggac gtttctgacg agtctgaagt tgaaatagtc gtctccgaca   9360
ttgccaagag attcggtgcg attaacgtac tagtgaacaa cgcaggcgtc accggtgccg   9420
ataaaccaac tcacgagatc gacgaacggg acctggacct cgtactgagc gtcgatgtga   9480
aaggagtatt cttcatgaca aaacactgca tcccctactt taaacaggct ggcggcggag   9540
ccatcgtcaa cttcgcgtct atctatggtc tggtggggtc gcaggagctt accccgtacc   9600
acgcagccaa aggtgcggtc gttgcccta ccaaacagga cgcggtgact tacggaccgt    9660
caaatatccg agtgaatgcg gtagcacccg gaaccatttt gactccacta gtcaaggagc   9720
tcggttcaag gggccccgat ggcttagatg gatatactaa acttatgggt gccaagcatc   9780
cgcttggtcg ggtaggaacc cccgaagaag tcgcggcagc aacattgttt ctggcatccg   9840
aagaagcttc gttcattact ggcgccgtcc ttcccgttga cggtggatat actgcgcagt   9900
gacattctca ggacgcggac gcaattcttg tgacagaatt ggttcacctc gcctgtatac   9960 tgccctcac caaaactgca ataaacgacc ggacgaggca ccgattttg aagttgacag     10020 gattacgcac tttaccggac agacgtagct gtgatcggct aaccatagac gttggaaggc   10080
ttcttcgatg acgatcgact ccgtcacaat acgcaggaat ggttgttggt cggtgagcct   10140
gtgtacagga agtaatattt tggtaaccct cggcatagat cgcagttggg gcagtggcgt   10200
ctgactcaaa ccgccggacg acaaatcatc ggcgaaagaa gccggtccgc atctcgaact   10260
gcactggtca agatagag cttcatcgat gcccgaggca cacgcctagt acgggaatca     10320
acgagtgttc gatagcctcg gcgcagaggc cgaagtcggc cgttctccct gatgttcctg   10380
gtcccggcga gataactaat gactatgttg tcgaactcgt cgagcacgct cgcctcgaac   10440
```

-continued

| | |
|---|---|
| tcagctcagt ctttggacac gagaatcgga gcgcacgcgt tcacctcggc aaggaggtga | 10500 |
| aagaggttca acgtgaacga atcggcattg tcgatgagca gagtgcgggt cgcgctcgtc | 10560 |
| ccctcacgtg tcgcgatctt ctagagtcga cctgcaggca tgctgcttaa gggctcatat | 10620 |
| catcgaaat | 10629 |

<210> SEQ ID NO 16
<211> LENGTH: 11471
<212> TYPE: DNA
<213> ORGANISM: Brevibacterium sp HCU

<400> SEQUENCE: 16

| | |
|---|---|
| gcaccgacga cgaaccgccg gcgtaccgac gctggctgcg ctggagcccc ggtgcccacg | 60 |
| actggcgcac cgggacgagc atgaccgtgc ccatggtggc cgtcatcatc gtctgcgtga | 120 |
| tcggcttcgg tccggccgcc ggggctgtcg cggtcttcgg cgcactcgtc tcgatgtgga | 180 |
| acccgggcgg gtcgctgcag cggcgactgc gcaggttcgc aatcgtctgc ccgctgttcc | 240 |
| cggcctcgat ggccatcggt gtgctcacca gcagatggcc gtggctggct ctcggtgcgc | 300 |
| aggtcgtgct cattcttgtc atcaccacgg cctaccatca cttcatgacc gggcccggac | 360 |
| ccggaccgct gcaccttttc tacgcctcgt gcatcggcgg ctacctcggc gcgaccgggc | 420 |
| aggggtgggg tgcggccggc atcaccgcct tcgcgagctg tctgaccgcg gccctcactc | 480 |
| tgctcgggct cttcgggccc gtcgtcgcgg gcctcgtccg caacggactc ggccgcaacg | 540 |
| ggagacgtcg tcctccagtt gaagccgagg agggctccgg cgtgccgggc gatctcgtga | 600 |
| cggctcctgc cgtgatcgac gaagacgcct ctcccgtctt cggtcccggc gcggtctcga | 660 |
| ccggcctgcg ctgctcgacc gccgggctgc tggccggggc ggtcgccctg ctgctgtcct | 720 |
| tcgaccactc ctactgggcc gtgctgtcgg cgacgatcgt cctccacggc gggcaagaca | 780 |
| ctccggcgac cgtgacccgc gcgcgccacc gagtgctggg caccctcggc ggggtcgcga | 840 |
| tcgtcgcact gctggctctg acccatccgg ggccggtcgt tcaactgctc gtcatcgtcc | 900 |
| tcgccgtctg ggggatgaat gtgatcatgg cctggcacta cgccgtgcc gcagcgttca | 960 |
| tcacggtgat gacgctgcag gccaacctgc tcatgctcgg cgagcaagcc actcccgaac | 1020 |
| tcatcatcga acgcctcatc gccaccgcg tcggcgtcgc cgcggcactg atcgtcctcg | 1080 |
| cctgctcgac cgggcgtgca cgaaggatcc tctcgaggtc actgtggttc gcctgtccga | 1140 |
| ttctgggaca gcggcagacc gggcagagac gatagcctcg aaccggaacg gcttgataag | 1200 |
| agcccgcccg gatctgttgc ggaatgaacc gcgccctgcc ggacgagctc ggccgggccg | 1260 |
| caatggcttc aatggatgaa gagaaagggt ggccgtgatg aaagcattcg caatgaaggc | 1320 |
| acagggcgca gcgctcgaag agatcgagtt ggatcgtccg aagcccatgg gcagagaagt | 1380 |
| tctgctcaag gtgacgcacg ccggtgtgtg tcataccgac acccatgttc aggacgcgcg | 1440 |
| ctacgatctg gggtcacggg ggaccctcga tatgtcgacc agaggcgtca cctacccctg | 1500 |
| cgtgatgggc cacagaccg tcggcgaggt cgtcgaagtc ggcgaggacg tcacagacgt | 1560 |
| cgcagtcggc gacacgtgcc tcgccttccc ctggatcggg tgcggggaat gcggaaaatg | 1620 |
| cgcccatgga catgagaacg cctgcgacaa cggtcgcgct ctcggcatca tccagttcgg | 1680 |
| cggcttcgcc gaatacctgc tcctgccgga tcagcggtat gccatcgatg tggctggagt | 1740 |
| cgatccggct tgggcggcca cgctcgcctg ctcgggtgtg acctcgtact cctccgctcg | 1800 |
| aaaagccaca gcgacggtca atcccgacga acccatcggc gtgatgggag tcggcgggt | 1860 |

-continued

```
cggcatgatg acagtcgccg ccctcgtcgc cctcggccac aagaacatca tcgcgatcga      1920
cgtctccgac gagaacctcg catccgcgca ggaactcggc gccaccttga ccgtgaattc      1980
gaagaatgcg accagccacg acctcgtcga ggccgcaggc ggacagttca tcgcaatcat      2040
cgacttggtc aacaccggtg acaccgtcgc gctggccttc gatgcgctct cccgcgcagg      2100
caagatcgtc caggtcggac tgttcggcgg cgagttcgtg gtcccgacgg cgatcatggc      2160
tctcaaaggt ctgaccctgc agggtaacta cgtcggcacg gtcgaagaag tccgcgaggt      2220
cgtcgagctg gcccggcagg gttcgctgcc gaagctgccg atcaccggcg gcacgctgaa      2280
cgtcgacggc gtcaatgacg gtctggagcg gctgcgcacg ggccgagctc gcggtcgcac      2340
ggtgctgacc ccctgacttg tctgacctcg tgaacccaac gtcacgcagc ctcacgcgac      2400
attgccggcc tcctcgcgtc cgaggaggcc ggcaatgtca tacgtgtttg tccgacagat      2460
ctatcagctg gagaccagtt ccgaacgcgc tgtgatccgg gcgcgcggtc cggacgagca      2520
ttcaacgcgc tcagctgagg aaacgtccct gctccaggcc gagagcgcgc agcttccggt      2580
agagcgtcga gcgagcgatg ccgagctgtt ctgcggcgat cgacttgttc ccgcctgctt      2640
cgttgagcac tcggatgacg gtttcgcgtt cggtctgctc gagagaggtc agctcacggc      2700
cgctggtgat cgtccggtat tcggcgggca ggtgctcgag accgatgtcg gagctcatgg      2760
ccttcggcag cgatgagacg aggacggatg cgagttcgcg cacgttgccc ggccagtggt      2820
gagcggccag agacttccgc gtcgccggct gcagccgcgg cgctcgaggt ccggagacat      2880
gctcggtgag tatgacgcgg gcgagatcgt cgatctcgtc ggtgcggtgc cgcagaggcg      2940
agacataggc cctccgcagg aaatgtgagc tcagcccgct ggcgtcatcg ccgcgcagct      3000
ccgtcgatga ggtcgccgtc agcggggaac cggcctcgtt cgtttcgatg acgagcgtgc      3060
ggacctccgc ggccgcctcg gcggggacct catcgatcct cgtgatcaac agggccgagc      3120
cctcatcgat ctgcgcccgc aggcggggca gatccgctgc agtgagaccg gatccggcga      3180
ccgtgagcag attgtccgcg aagccccaga gccgggtcag atacgcggcg gtccgggcct      3240
tgccgacacc gggctcaccg gtgatgagga cgggaccggt ctgctgtgcg aagccatcga      3300
gctgagactg cagctgccgg gtggccaggc tgcgccgggg cagacgttcg acgcccgaac      3360
gcgaaggacc tgtgagcaga gcgagcgcag gcgccgccgt atgtccactc ccggcaacgg      3420
gctctgtgag agcgcgcagc tccataacca cgcccagggg ctcggcggca tcgctgaccc      3480
ggcgggcagt gacttcgacg tctcggccgt cggccaagcg cagagtctcg gtgtggctgg      3540
ggcggtcggg gacgatgccg ctcgcccagt cccacagcat cgcctgatca gagtagtcga      3600
ggtagctcga cgccaccggg gtggcgatga cggtatcggg actcatggcg acgacggcct      3660
tcgccgagga gcgcctgacc tgggcgtatt cacgcaggag acggcgttcc gtgcgggagg      3720
actggccgta gagccgctcc tcgatatcgg agacagcggc ggagatgagc ggagccatga      3780
gatcgttgac atcaccgatt tcgcacgtga tgtcgaggat gccgacgacg gaccggttga      3840
tcgggtggac gatcggtgcg ccgacacagg cgaagcggtg gagggactcg agcagatgtt      3900 cctcacccctt gacccggaat ggggtgcgct cctcgagtgc tgtgccgatg ccgttggtgc      3960
ccgcgaactc ctcagcgaat tggaaacccg gtgccacggt cgcactgtcg agttgggaga      4020
gcagctcgtg cttgcccgtc cagcggtcga tgatgcgggc atcacggtcc gccagaagga      4080
tggtcaccgg agcgtcctgg agctgagtcg agaggcgatc gagaaccgga cgtgccgcga      4140
gcagcacccg gttatccggg atgccgtcgt cggtgaaggg cagctcgcgt gccgaacggt      4200
cgacgccgat gacctgacag cggcgccatg accgatcgat ctcggcccga atagccgccg      4260
```

-continued

```
aatcaggaag cgcctgcgcg tcgaagtcaa cgacaggctc tgctgcggct gcggttctgt    4320
ggcgagcggc tgtgctcaat gtcaacacct cgatgtgttc gatgactgac ggccttggct    4380
atgaccctcc attctaccgt tgccacttcg ggagtggagt gtcccacaat gcaacaccgg    4440
cggacgagag gccgcgtcac gcggtgacgg aagcctcctc ggtgaggtct gacgtggcgt    4500
tcagacgcac cgttgcaata tgggacacgg tcagttccgt cggcgaaagt agtctgatgc    4560
caccaatcaa ccgccgtcac cgtcgccggc gtcaggaatg atggcgcagc agtgcaaaga    4620
cggacagcag aaagcaggtg tcgcaatgag tggaaacgag atctcggaag tcgccagggg    4680
attcacctac ctcgaaggac cgcggtggca tgatggccga ctgtggttcg tggacttcta    4740
cacgtacacg gtcaacgcgg tcaacgatga cggcagcatc gaggagatcg ccgtcgtcga    4800
ccagcagccc tcgggcctgg gctggctgcc cgacgggcgg ctgctcatcg tgtcgatgaa    4860
ggaccgcaag atcctacgcc gcgaagagga cggcaccctc gtcgaacatg ccgacatctc    4920
cgcccactgt gtcggccacg ccaatgacat ggtcgtcgcg gagaacgggc aggcctacgt    4980
cggcgagttc ggcttcgacc tcatgggcgg ggccgatcac aagttcgcca atgtcatctc    5040
gtcaacaccg acggcacctc ggagtcgtcg ccagcggact ctccttcccc aacggcatgg    5100
tcatcactcc cgacggcaag acgctcatcg tcaacgaact cttcggcaac aagatcaccg    5160
ccttcgacat cggagcggac ggaaagctcg ccaataagcg cgacttcgcg aacttcggtg    5220
agatcggaga cgaaccggac gtggcgaagc ggatcgaggc tgcgacgatc gttcccgacg    5280
gtctcgccct cgacgccgag ggcgcggtgt ggatcgcgaa caccgtcaac cagaacgcca    5340
cccgcatcgc cgaaggcgga cagatcctcg acaccgtcga caccgctccc gaagggatct    5400
tcgcagtggc actcggcggc gacgacggca agacgctctt cctgtgtgcg gcccccgact    5460
gggatgaagg cgcacgcagc aaagcgcgcg agggacgcat gctcgcaaca accgtcgccg    5520
tccctcacgc aggcaggccc tgagtcctac agccgacgct taggacaccc tgccgaggcg    5580
gtcgtgccgt catcgatgcc gacatcgatg acggtgcgac cgcctttcgt cgtgcccgga    5640
tgcggctggg ccttcgctcc cgcacggacg agctgagccg cctcggcgag gacgaggtt    5700 acggcatatg tcgtcatttg acgacaaggt ggctgactga ctcgatatag gacaccgcac    5760
gggtcggcgg cgaatctatc gtcgaatcat ccgggcagac gaacgaccat tgtcccgggt    5820
tcgaaggagg agaagacaat gacgtcaacc atgcctgcac cgacagcagc acaggcgaac    5880
gcagacgaga ccgaggtcct cgacgcactc atcgtgggtg gcggattctc ggggcctgta    5940
tctgtcgacc gcctgcgtga agacgggttc aaggtcaagg tctgggacgc cgccggcgga    6000
ttcggcggca tctggtggtg gaactgctac ccgggtgctc gtacggacag caccggacag    6060
atctatcagt tccagtacaa ggacctgtgg aaggacttcg acttcaagga gctctacccc    6120
gacttcaacg gggttcggga gtacttcgag tacgtcgact cgcagctcga cctgtcccgc    6180
gacgtcacat tcaacaccct tgcggagtcc tgcacatggg acgacgctgc caaggagtgg    6240
acggtgcgat cgtcggaagg acgtgagcag cgggcccgtg cggtcatcgt cgccaccggc    6300
ttcggtgcga agcccctcta cccgaacatc gagggcctcg acagcttcga aggcgagtgc    6360
catcacaccg cacgctggcc gcagggtggc ctcgacatga cgggcaagcg agtcgtcgtc    6420
atgggcaccg gtgcttccgg catccaggtc attcaagaag ccgcggcggt tgccgaacac    6480
ctcaccgtct tccagcgcac cccgaaccct tgccctgccga tgcggcagca gcggctgtcg    6540
gccgatgaca acgatcgcta ccgagagaac atcgaagatc gtttccaaat ccgtgacaat    6600
```

-continued

```
tcgtttgccg gattcgactt ctacttcatc ccgcagaacg ccgcggacac ccccgaggac    6660
gagcggaccg cgatctacga aaagatgtgg gacgaaggcg gattcccact gtggctcgga    6720
aacttccagg gactcctcac cgatgaggca gccaaccaca ccttctacaa cttctggcgt    6780
tcgaaggtgc acgatcgtgt gaaggatccc aagaccgccg agatgctcgc accggcgacc    6840
ccaccgcacc cgttcggcgt caagcgtccc tcgctcgaac agaactactt cgacgtatac    6900
aaccaggaca atgtcgatct catcgactcg aatgccaccc cgatcacccg ggtccttccg    6960
aacggggtcg aaaccccgga cggagtcgtc gaatgcgatg tcctcgtgct ggccaccggc    7020
ttcgacaaca acagcggcgg catcaacgcc atcgatatca aagccggcgg gcagctgctg    7080
cgtgacaagt gggcgaccgg cgtggacacc tacatggggc tgtcgacgca cggattcccc    7140
aatctcatgt tcctctacgg cccgcagagc ccttcgggct tctgcaatgg gaccgacttc    7200
ggcggagcgc caggcgatat ggtcgccgac ttcctcatct ggctcaagga caacggcatc    7260
tcgcggttcg aatccaccga agaggtcgag cgggaatggc gcgcccatgt cgacgacatc    7320
ttcgtcaact cgctgttccc caaggcgaag tcctggtact ggggcgccaa cgtccccggc    7380
aagccggcgc agatgctcaa ctattcggag gcgtccccgc atatctagag aagtgggacg    7440
aggtcaacag ccacggctac gccggttttg agttcgatcg tgagcatact gagaaatcgt    7500
gcgaacgtgc tgcctgaggg ctggccattg ggctgaatgc gacttaagtg tgctcagatt    7560
gcatgtctac tcgccagtag cgtgcaatct gagcacactt aactgtcgtt cgcgggcaca    7620
ggtgcctgtt cgtgcaggcg ctgtggcgac tcggccgggt cagtcgtgag attcgggggc    7680
ggccgcctcg gcgcgttcga tgtcctgggc ggcgaacacg cgtccagagc cgggaaagcg    7740
ggcgtcaatc gtccttgcgc aggtattcat gatcttcgtg ccctcatatt cctggcggat    7800
cacccccgct tcgcgcagag tgcggaagtg ataggtcgcc gtggacttcg acaccggcag    7860
ctcgaaggtc gcacacgcat gatcgccgaa agcgtcgttg agtttgcagg cgacggtgcg    7920
gcggaccggg tcggcgaggg cggccaggac ggtgtcgagt ctcatctcgt ccctgctggg    7980
gtggtcgagt gtgcgcatct ggatcctccc atctcgccat cgtgtcggtc agcgtcggtg    8040
gatgtcgtct gaacagccac cgatcacagg tagcgccgta tctctccatt gtacgaaata    8100
tttggtagta cgaaattcat cgtagtaaag tgcgaactcg aagtacgaaa aatctcatac    8160
ttccagccga ctactttcga cgagatcacg aggtgtcatg tctcatctgc tgttcgaacc    8220
gctcacactg cgcggcctga ccttccgcaa tcggatctgg gttccgccca tgtgccagta    8280
ctccgtcgag actctagacg gggtccccgc tccttggcac accgtccact acggtgcgat    8340
ggcccgcggc ggagcggcgc ccgtcatcgt cgaagccacc ggagtcgctc cggaggcgcg    8400
catctcggcc aaggatctgg gctggaacga cgaacagcgc gacgccttcg tccccatcgt    8460
cgacttcctc cacacccagg gcgcggccgc cggcatccag ctcgcccacg ccggccgcaa    8520
ggcctcgacc tatccggagt ggggaaccga ccgcgacggc agcctgcccg tcgacgaagg    8580
cggttggcag accgtggctc cgtccgcact ggccttcgac ggcctcgccg aaccgcgagc    8640
actgaccgaa acagagatcg ccgaggtggt cgcggccttc cggtcctcgg cccgccgggc    8700
gatcgaggcc gggttcgact tcgtcgagat ccacgccgca cacggatacc tcctccatga    8760
gttcctgtcg cccctgagca caaccgcacc gactcctacg gcggatcct tggagaaccg    8820 ggcccgactg ctgctcgaca tcgtcgatgc cacccgcacc gaggtgggcg aggacgttcc    8880
cgtgttcgtg cgcctctccg cgacggactg gacagaaggc gggctcacgc tcgacgcacac    8940 agtggaggtc gccggatggc tcaaggaaca cggtgtcgac ctcatcgacg tctcctccgg    9000
```

```
cggcaatgtg atggcgtcga ttcccgtcgg tcccggctac cagacgaccc tggccgccgg   9060
cgtgcggcag ggatcggggc tgccgaccgc ggccgtcggc ctcatcagcg aaccgttcca   9120
gggcgagcac attctggcca ccggccaggc cgatgtgatc ctcgtgggcc gtgagtacct   9180
ccgcgatccg aacttcgcgc tgcgcgccgc cgacgccctg cgcttcgaca tcgactaccg   9240
cccggctcag taccaccgcg cgtataagtg agctgagctc aattcgctgg agcggctcgg   9300
cgctcatacg ctgacggccc agttgaagtc gacagcaatg ttcaaatgtg tgctgtccga   9360
cttcaactgg gccgttggcg tctgtcatct cgcgggacag cgctcgccga gggtgagcgt   9420
gtggagatgt ggctgagctc agaacggtcg gttgcagcta ggccaggcct ccgagccaca   9480
ttccgatcgc cgcggccgtc gtggtgagaa cgagggtgcc gagcgcgttg accaggccgg   9540
cggcccagcg acgttcctgg agaagccgga ccgtttcgaa gctcgccgtc gaaaacgtcg   9600
tatagccgcc gaggaatccc gtgccgagca ccaggtgcca ggcttgcgga agcaggttcg   9660
ctccggccag tccggtcagc aggccgagca cgagtgatcc cgagacattg atgatgatcg   9720
ttccccacgg cagggccgtg ctcatgcggg acttgatgag tccgtcgatc agcattcgtg   9780
atgaggcgcc gagtccgccg gcggcggcaa gggcgacgaa gaccagcggc gtcatcgggc   9840
acctcctcga cgcagcgtcg tcgccgtggc gatgccggcg aacgtggcga gaccgccgat   9900
gagtaccgtg cccaccgcgt aggcaatccc gatgccgggg ctgctcgccc cacccggacc   9960
cgcgccgagg cggcccgccg tatcggcggc cagcgcgctg tatgtggtga atccgcccat  10020
gaaaccggtc ccgaccagga tccgcgttcg gcgacgccac ctttcatcgg ggccgctgcg  10080
cgccagggaa tccaacagca ggccgagcag aaacgccccg aggatgttga ccgtgaggat  10140
tgcccacggc acatcgccga ggggcggcag gctcaggctg atcgcctcgc gtgccgcagt  10200
tccgactgcg ccgccgatga acgcgagccc cagataggac aggcgcaggt ggactggccg  10260
ggtcactgtt cgcccgcgcc ggcttgagtc tcggcagcgg gggaagcgcc aggggtcggc  10320
gacgtcgcag gggattcggg gttgcccatg tcgtcggtgc ctgtcgccag cggaacgacg  10380 acgaggggc gatgctggcg ccttgacagt tggatcgcga ccgagccatt gaagaactca  10440
tgcagtgagc cgcgaacacc tgcgcgacgg acgccgagga tgatcatgcg ggcatcgagc  10500
gcctcggcga gccggtcgag ttcctgtgcc ggtgacccgg ccagtgcgcg ggtcgaccag  10560
gcaacattcg tgccttccag ggctacagcg atgcggtcct ggagttcggg gtcgaactcg  10620
gtggctgcct cgtcggtggt gtccggatcg atgggcatcg agagcacgga gccgtcggga  10680
cgagtctcaa cggtgtatcg ggagtcgtcg acgtgggcgc agacgaactc ggcgtccaag  10740
tgggcgacgt agtccgcggc ggcggcgatc acctcggcgg gctgatcggg gacgacgccg  10800
aggatgatgc gggcgcgcgg cggcccgtcg tatatcggat cggggctggc ggtcatggtc  10860
tctcctacct ttcgggcatg ctgaagccgt ccgaggtaag ggactgtttt cgaagacgaa  10920
caccgaaggt tccgcttccg agttgggtac ggcgagcccc accgccgtgc cgcgcagtcg  10980
cgacaccaat attgtgccac aggaccatag cgaaagggcc gtcggacggc cggcatccga  11040
agatggccgg catcccgacg gcccccgctg gggtatcagc gctcgtggga ctcacccttc  11100
gcggatcgtc atcctgctca gtttgtcgcc gtcgatgacg aaggcgaacg atgaccgacc  11160
gttggcgtgc gtggagcgcc aatcgccgat gatggtgacg tcgtttccgt cgacggtgac  11220
tcttcgggcg tgaggacgcc ggttgcaccg atgaattcct tatcgctcca ggccttgatg  11280
gcctcccggc cctggaactc gcgtcccag tcgtcgacag tgccatcggg ggtgaatgcg  11340
```

```
tccaggaagc cctggttgtc gtgagcgttg acggtgtcga tgaagccggc gacgggttcg    11400
ggaatctgca ggtctgacat atgtgctcct gtgctgttga gatatgtgct gtcgggatgt    11460
ggttgtcgat c                                                          11471
```

<210> SEQ ID NO 17
<211> LENGTH: 1059
<212> TYPE: DNA
<213> ORGANISM: Brevibacterium sp HCU

<400> SEQUENCE: 17

```
atgaaagcat tcgcaatgaa ggcacagggc gcagcgctcg aagagatcga gttggatcgt      60
ccgaagccca tgggcagaga agttctgctc aaggtgacgc acgccggtgt gtgtcatacc     120
gacacccatg ttcaggacgg cggctacgat ctggggtcac gggggaccct cgatatgtcg     180
accagaggcg tcacctaccc ctgcgtgatg ggccacgaga ccgtcggcga ggtcgtcgaa     240
gtcggcgagg acgtcacaga cgtcgcagtc ggcgacacgt gcctcgcctt ccctggatc      300 gggtgcgggg aatgcggaaa atgcgcccat ggacatgaga acgcctgcga caacggtcgc     360
gctctcggca tcatccagtt cggcggcttc gccgaatacc tgctcctgcc ggatcagcgg     420
tatgccatcg atgtggctgg agtcgatccg gcttgggcgg ccacgctcgc ctgctcgggt     480
gtgacctcgt actcctccgc tcgaaaagcc acagcgacgg tcaatcccga cgaacccatc     540
ggcgtgatgg gagtcggcgg ggtcggcatg atgacagtcg ccgccctcgt cgccctcggc     600
cacaagaaca tcatcgcgat cgacgtctcc gacgagaacc tcgcatccgc gcaggaactc     660
ggcgccacct tgaccgtgaa ttcgaagaat gcgaccagcc acgacctcgt cgaggccgca     720
ggcggacagt tcatcgcaat catcgacttg gtcaacaccg tgacaccgt cgcgctggcc      780 ttcgatgcgc tctcccgcgc aggcaagatc gtccaggtcg actgttcgg cggcgagttc      840 gtggtcccga cggcgatcat ggctctcaaa ggtctgaccc tgcagggtaa ctacgtcggc     900
acggtcgaag aagtccgcga ggtcgtcgag ctggcccggc agggttcgct gccgaagctg     960
ccgatcaccg gcggcacgct gaacgtcgac ggcgtcaatg acggtctgga gcggctgcgc    1020
acgggccgag ctcgcggtcg cacggtgctg accccctga                           1059
```

<210> SEQ ID NO 18
<211> LENGTH: 352
<212> TYPE: PRT
<213> ORGANISM: Brevibacterium sp HCU

<400> SEQUENCE: 18

```
Met Lys Ala Phe Ala Met Lys Ala Gln Gly Ala Ala Leu Glu Glu Ile
  1               5                  10                  15

Glu Leu Asp Arg Pro Lys Pro Met Gly Arg Glu Val Leu Leu Lys Val
             20                  25                  30

Thr His Ala Gly Val Cys His Thr Asp Thr His Val Gln Asp Gly Gly
         35                  40                  45

Tyr Asp Leu Gly Ser Arg Gly Thr Leu Asp Met Ser Thr Arg Gly Val
     50                  55                  60

Thr Tyr Pro Cys Val Met Gly His Glu Thr Val Gly Glu Val Val Glu
 65                  70                  75                  80

Val Gly Glu Asp Val Thr Asp Val Ala Val Gly Asp Thr Cys Leu Ala
                 85                  90                  95

Phe Pro Trp Ile Gly Cys Gly Glu Cys Gly Lys Cys Ala His Gly His
                100                 105                 110
```

```
Glu Asn Ala Cys Asp Asn Gly Arg Ala Leu Gly Ile Ile Gln Phe Gly
            115                 120                 125

Gly Phe Ala Glu Tyr Leu Leu Leu Pro Asp Gln Arg Tyr Ala Ile Asp
        130                 135                 140

Val Ala Gly Val Asp Pro Ala Trp Ala Ala Thr Leu Ala Cys Ser Gly
145                 150                 155                 160

Val Thr Ser Tyr Ser Ser Ala Arg Lys Ala Thr Ala Thr Val Asn Pro
                165                 170                 175

Asp Glu Pro Ile Gly Val Met Gly Val Gly Val Gly Met Met Thr
            180                 185                 190

Val Ala Ala Leu Val Ala Leu Gly His Lys Asn Ile Ile Ala Ile Asp
            195                 200                 205

Val Ser Asp Glu Asn Leu Ala Ser Ala Gln Glu Leu Gly Ala Thr Leu
    210                 215                 220

Thr Val Asn Ser Lys Asn Ala Thr Ser His Asp Leu Val Glu Ala Ala
225                 230                 235                 240

Gly Gly Gln Phe Ile Ala Ile Asp Leu Val Asn Thr Gly Asp Thr
                245                 250                 255

Val Ala Leu Ala Phe Asp Ala Leu Ser Arg Ala Gly Lys Ile Val Gln
            260                 265                 270

Val Gly Leu Phe Gly Gly Glu Phe Val Val Pro Thr Ala Ile Met Ala
        275                 280                 285

Leu Lys Gly Leu Thr Leu Gln Gly Asn Tyr Val Gly Thr Val Glu Glu
    290                 295                 300

Val Arg Glu Val Val Glu Leu Ala Arg Gln Gly Ser Leu Pro Lys Leu
305                 310                 315                 320

Pro Ile Thr Gly Gly Thr Leu Asn Val Asp Gly Val Asn Asp Gly Leu
                325                 330                 335

Glu Arg Leu Arg Thr Gly Arg Ala Arg Gly Arg Thr Val Leu Thr Pro
            340                 345                 350

<210> SEQ ID NO 19
<211> LENGTH: 1761
<212> TYPE: DNA
<213> ORGANISM: Brevibacterium sp HCU

<400> SEQUENCE: 19
gttgacttcg acgcgcaggc gcttcctgat tcggcggcta ttcgggccga gatcgatcgg     60
tcatggcgcc gctgtcaggt catcggcgtc gaccgttcgg cacgcgagct gcccttcacc    120
gacgacggca tcccggataa ccgggtgctg ctcgcggcac gtccggttct cgatcgcctc    180
tcgactcagc tccaggacgc tccggtgacc atccttctgg cggaccgtga tgcccgcatc    240
atcgaccgct ggacgggcaa gcacgagctg ctctcccaac tcgacagtgc gaccgtggca    300
ccgggtttcc aattcgctga ggagttcgcg ggcaccaacg gcatcggcac agcactcgag    360
gagcgcaccc cattccgggt caagggtgag gaacatctgc tcgagtccct ccaccgcttc    420
gcctgtgtcg gcgcaccgat cgtccacccg atcaaccggt ccgtcgtcgg catcctcgac    480
atcacgtgcg aaatcggtga tgtcaacgat ctcatggctc cgctcatctc cgccgctgtc    540
tccgatatcg aggagcggct ctacggccag tcctcccgca cggaacgccg tctcctgcgt    600
gaatacgccc aggtcaggcg ctcctcggcg aaggccgtcg tcgccatgag tcccgatacc    660
gtcatcgcca ccccggtggc gtcgagctac ctcgactact ctgatcaggc gatgctgtgg    720
gactgggcga gcggcatcgt ccccgaccgc cccagccaca ccgagactct gcgcttggcc    780
```

-continued

```
gacggccgag acgtcgaagt cactgcccgc cgggtcagcg atgccgccga gcccctgggc    840
gtggttatgg agctgcgcgc tctcacagag cccgttgccg ggagtggaca tacggcggcg    900
cctgcgctcg ctctgctcac aggtccttcg cgttcgggcg tcgaacgtct gcccggccgc    960
agcctggcca cccggcagct gcagtctcag ctcgatggct tcgcacagca gaccggtccc   1020
gtcctcatca ccggtgagcc cggtgtcggc aaggcccgga ccgccgcgta tctgacccgg   1080
ctctggggct tcgcggacaa tctgctcacg gtcgccggat ccgtctcac tgcagcggat   1140
ctgccccgcc tgcgggcgca gatcgatgag ggctcggccc tgttgatcac gaggatcgat   1200
gaggtccccg ccgaggcggc cgcggaggtc cgcacgctcg tcatcgaaac gaacgaggcc   1260
ggttccccgc tgacggcgac ctcatcgacg gagctgcgcg gcgatgacgc cagcgggctg   1320
agctcacatt tcctgcggag ggcctatgtc tcgcctctgc ggcaccgcac cgacgagatc   1380
gacgatctcg cccgcgtcat actcaccgag catgtctccg gacctcgagc ccgcggctg    1440
cagccggcga cgcggaagtc tctggccgct caccactggc cgggcaacgt gcgcgaactc   1500
gcatccgtcc tcgtctcatc gctgccgaag gccatgagct ccgacatcgg tctcgagcac   1560
ctgcccgcca ataccggac gatcaccagc ggccgtgagc tgacctctct cgagcagacc   1620
gaacgcgaaa ccgtcatccg agtgctcaac gaagcaggcg ggaacaagtc gatcgccgca   1680
gaacagctcg gcatcgctcg ctcgacgctc taccggaagc tgcgcgctct cggcctggag   1740
cagggacgtt tcctcagctg a                                             1761
```

<210> SEQ ID NO 20
<211> LENGTH: 586
<212> TYPE: PRT
<213> ORGANISM: Brevibacterium sp HCU

<400> SEQUENCE: 20

```
Val Asp Phe Asp Ala Gln Ala Leu Pro Asp Ser Ala Ala Ile Arg Ala
  1               5                  10                  15

Glu Ile Asp Arg Ser Trp Arg Arg Cys Gln Val Ile Gly Val Asp Arg
             20                  25                  30

Ser Ala Arg Glu Leu Pro Phe Thr Asp Asp Gly Ile Pro Asp Asn Arg
         35                  40                  45

Val Leu Leu Ala Ala Arg Pro Val Leu Asp Arg Leu Ser Thr Gln Leu
     50                  55                  60

Gln Asp Ala Pro Val Thr Ile Leu Leu Ala Asp Arg Asp Ala Arg Ile
 65                  70                  75                  80

Ile Asp Arg Trp Thr Gly Lys His Glu Leu Leu Ser Gln Leu Asp Ser
                 85                  90                  95

Ala Thr Val Ala Pro Gly Phe Gln Phe Ala Glu Glu Phe Ala Gly Thr
            100                 105                 110

Asn Gly Ile Gly Thr Ala Leu Glu Glu Arg Thr Pro Phe Arg Val Lys
        115                 120                 125

Gly Glu Glu His Leu Leu Glu Ser Leu His Arg Phe Ala Cys Val Gly
    130                 135                 140

Ala Pro Ile Val His Pro Ile Asn Arg Ser Val Val Gly Ile Leu Asp
145                 150                 155                 160

Ile Thr Cys Glu Ile Gly Asp Val Asn Asp Leu Met Ala Pro Leu Ile
                165                 170                 175

Ser Ala Ala Val Ser Asp Ile Glu Glu Arg Leu Tyr Gly Gln Ser Ser
            180                 185                 190

Arg Thr Glu Arg Arg Leu Leu Arg Glu Tyr Ala Gln Val Arg Arg Ser
```

```
                    195                 200                 205
Ser Ala Lys Ala Val Ala Met Ser Pro Asp Thr Val Ile Ala Thr
        210                 215                 220

Pro Val Ala Ser Ser Tyr Leu Asp Tyr Ser Asp Gln Ala Met Leu Trp
225                 230                 235                 240

Asp Trp Ala Ser Gly Ile Val Pro Asp Arg Pro Ser His Thr Glu Thr
                245                 250                 255

Leu Arg Leu Ala Asp Gly Arg Asp Val Glu Val Thr Ala Arg Arg Val
            260                 265                 270

Ser Asp Ala Ala Glu Pro Leu Gly Val Val Met Glu Leu Arg Ala Leu
        275                 280                 285

Thr Glu Pro Val Ala Gly Ser Gly His Thr Ala Ala Pro Ala Leu Ala
    290                 295                 300

Leu Leu Thr Gly Pro Ser Arg Ser Gly Val Glu Arg Leu Pro Gly Arg
305                 310                 315                 320

Ser Leu Ala Thr Arg Gln Leu Gln Ser Gln Leu Asp Gly Phe Ala Gln
                325                 330                 335

Gln Thr Gly Pro Val Leu Ile Thr Gly Glu Pro Gly Val Gly Lys Ala
            340                 345                 350

Arg Thr Ala Ala Tyr Leu Thr Arg Leu Trp Gly Phe Ala Asp Asn Leu
        355                 360                 365

Leu Thr Val Ala Gly Ser Gly Leu Thr Ala Ala Asp Leu Pro Arg Leu
    370                 375                 380

Arg Ala Gln Ile Asp Glu Gly Ser Ala Leu Leu Ile Thr Arg Ile Asp
385                 390                 395                 400

Glu Val Pro Ala Glu Ala Ala Glu Val Arg Thr Leu Val Ile Glu
                405                 410                 415

Thr Asn Glu Ala Gly Ser Pro Leu Thr Ala Thr Ser Ser Thr Glu Leu
            420                 425                 430

Arg Gly Asp Asp Ala Ser Gly Leu Ser Ser His Phe Leu Arg Arg Ala
        435                 440                 445

Tyr Val Ser Pro Leu Arg His Arg Thr Asp Glu Ile Asp Asp Leu Ala
    450                 455                 460

Arg Val Ile Leu Thr Glu His Val Ser Gly Pro Arg Ala Pro Arg Leu
465                 470                 475                 480

Gln Pro Ala Thr Arg Lys Ser Leu Ala Ala His His Trp Pro Gly Asn
                485                 490                 495

Val Arg Glu Leu Ala Ser Val Leu Val Ser Ser Leu Pro Lys Ala Met
            500                 505                 510

Ser Ser Asp Ile Gly Leu Glu His Leu Pro Ala Glu Tyr Arg Thr Ile
        515                 520                 525

Thr Ser Gly Arg Glu Leu Thr Ser Leu Glu Gln Thr Glu Arg Glu Thr
    530                 535                 540

Val Ile Arg Val Leu Asn Glu Ala Gly Gly Asn Lys Ser Ile Ala Ala
545                 550                 555                 560

Glu Gln Leu Gly Ile Ala Arg Ser Thr Leu Tyr Arg Lys Leu Arg Ala
                565                 570                 575

Leu Gly Leu Glu Gln Gly Arg Phe Leu Ser
            580                 585

<210> SEQ ID NO 21
<211> LENGTH: 1590
<212> TYPE: DNA
<213> ORGANISM: Brevibacterium sp HCU
```

<400> SEQUENCE: 21

```
atgacgtcaa ccatgcctgc accgacagca gcacaggcga acgcagacga gaccgaggtc      60
ctcgacgcac tcatcgtggg tggcggattc tcggggcctg tatctgtcga ccgcctgcgt     120
gaagacgggt tcaaggtcaa ggtctgggac gccgccggcg gattcggcgg catctggtgg     180
tggaactgct acccgggtgc tcgtacggac agcaccggac agatctatca gttccagtac     240
aaggacctgt ggaaggactt cgacttcaag gagctctacc ccgacttcaa cggggttcgg     300
gagtacttcg agtacgtcga ctcgcagctc gacctgtccc gcgacgtcac attcaacacc     360
tttgcggagt cctgcacatg ggacgacgct gccaaggagt ggacggtgcg atcgtcggaa     420
ggacgtgagc agcgggcccg tgcggtcatc gtcgccaccg gcttcggtgc gaagcccctc     480
tacccgaaca tcgagggcct cgacagcttc gaaggcgagt gccatcacac cgcacgctgg     540
ccgcagggtg gcctcgacat gacgggcaag cgagtcgtcg tcatgggcac cggtgcttcc     600
ggcatccagg tcattcaaga gccgcggcg gttgccgaac acctcaccgt cttccagcgc      660
accccgaacc ttgccctgcc gatgcggcag cagcggctgt cggccgatga caacgatcgc     720
taccgagaga acatcgaaga tcgttttcca atccgtgaca attcgtttgc cggattcgac     780
ttctacttca tcccgcagaa cgccgcggac accccgaggg acgagcggac cgcgatctac     840
gaaaagatgt gggacgaagg cggattccca ctgtggctcg gaaacttcca gggactcctc     900
accgatgagg cagccaacca caccttctac aacttctggc gttcgaaggt gcacgatcgt     960
gtgaaggatc ccaagaccgc cgagatgctc gcaccggcga ccccaccgca cccgttcggc    1020
gtcaagcgtc cctcgctcga acagaactac ttcgacgtat acaaccagga caatgtcgat    1080
ctcatcgact cgaatgccac cccgatcacc cgggtccttc cgaacggggt cgaaaccccg    1140
gacggagtcg tcgaatgcga tgtcctcgtg ctggccaccg gcttcgacaa caacagcggc    1200
ggcatcaacg ccatcgatat caaagccggc gggcagctgc tgcgtgacaa gtgggcgacc    1260
ggcgtggaca cctacatggg gctgtcgacg cacggattcc ccaatctcat gttcctctac    1320
ggcccgcaga gcccttcggg cttctgcaat gggaccgact cggcggagc gccaggcgat     1380
atggtcgccg acttcctcat ctggctcaag gacaacggca tctcgcggtt cgaatccacc    1440
gaagaggtcg agcgggaatg gcgcgcccat gtcgacgaca tcttcgtcaa ctcgctgttc    1500
cccaaggcga agtcctggta ctggggcgcc aacgtccccg gcaagccggc gcagatgctc    1560
aactattcgg aggcgtcccc gcatatctag                                      1590
```

<210> SEQ ID NO 22
<211> LENGTH: 529
<212> TYPE: PRT
<213> ORGANISM: Brevibacterium sp HCU

<400> SEQUENCE: 22

```
Met Thr Ser Thr Met Pro Ala Pro Thr Ala Gln Ala Asn Ala Asp
  1               5                  10                  15

Glu Thr Glu Val Leu Asp Ala Leu Ile Val Gly Gly Gly Phe Ser Gly
             20                  25                  30

Pro Val Ser Val Asp Arg Leu Arg Glu Asp Gly Phe Lys Val Lys Val
         35                  40                  45

Trp Asp Ala Ala Gly Gly Phe Gly Gly Ile Trp Trp Asn Cys Tyr
     50                  55                  60

Pro Gly Ala Arg Thr Asp Ser Thr Gly Gln Ile Tyr Gln Phe Gln Tyr
 65                  70                  75                  80
```

-continued

```
Lys Asp Leu Trp Lys Asp Phe Asp Phe Lys Glu Leu Tyr Pro Asp Phe
             85                  90                  95

Asn Gly Val Arg Glu Tyr Phe Glu Tyr Val Asp Ser Gln Leu Asp Leu
            100                 105                 110

Ser Arg Asp Val Thr Phe Asn Thr Phe Ala Glu Ser Cys Thr Trp Asp
            115                 120                 125

Asp Ala Ala Lys Glu Trp Thr Val Arg Ser Ser Glu Gly Arg Glu Gln
        130                 135                 140

Arg Ala Arg Ala Val Ile Val Ala Thr Gly Phe Gly Ala Lys Pro Leu
145                 150                 155                 160

Tyr Pro Asn Ile Glu Gly Leu Asp Ser Phe Glu Gly Glu Cys His His
                165                 170                 175

Thr Ala Arg Trp Pro Gln Gly Gly Leu Asp Met Thr Gly Lys Arg Val
            180                 185                 190

Val Val Met Gly Thr Gly Ala Ser Gly Ile Gln Val Ile Gln Glu Ala
        195                 200                 205

Ala Ala Val Ala Glu His Leu Thr Val Phe Gln Arg Thr Pro Asn Leu
        210                 215                 220

Ala Leu Pro Met Arg Gln Gln Arg Leu Ser Ala Asp Asp Asn Asp Arg
225                 230                 235                 240

Tyr Arg Glu Asn Ile Glu Asp Arg Phe Gln Ile Arg Asp Asn Ser Phe
                245                 250                 255

Ala Gly Phe Asp Phe Tyr Phe Ile Pro Gln Asn Ala Ala Asp Thr Pro
            260                 265                 270

Glu Asp Glu Arg Thr Ala Ile Tyr Glu Lys Met Trp Asp Glu Gly Gly
        275                 280                 285

Phe Pro Leu Trp Leu Gly Asn Phe Gln Gly Leu Leu Thr Asp Glu Ala
        290                 295                 300

Ala Asn His Thr Phe Tyr Asn Phe Trp Arg Ser Lys Val His Asp Arg
305                 310                 315                 320

Val Lys Asp Pro Lys Thr Ala Glu Met Leu Ala Pro Ala Thr Pro Pro
                325                 330                 335

His Pro Phe Gly Val Lys Arg Pro Ser Leu Glu Gln Asn Tyr Phe Asp
            340                 345                 350

Val Tyr Asn Gln Asp Asn Val Asp Leu Ile Asp Ser Asn Ala Thr Pro
        355                 360                 365

Ile Thr Arg Val Leu Pro Asn Gly Val Glu Thr Pro Asp Gly Val Val
        370                 375                 380

Glu Cys Asp Val Leu Val Leu Ala Thr Gly Phe Asp Asn Asn Ser Gly
385                 390                 395                 400

Gly Ile Asn Ala Ile Asp Ile Lys Ala Gly Gln Leu Leu Arg Asp
                405                 410                 415

Lys Trp Ala Thr Gly Val Asp Thr Tyr Met Gly Leu Ser Thr His Gly
            420                 425                 430

Phe Pro Asn Leu Met Phe Leu Tyr Gly Pro Gln Ser Pro Ser Gly Phe
        435                 440                 445

Cys Asn Gly Thr Asp Phe Gly Gly Ala Pro Gly Asp Met Val Ala Asp
        450                 455                 460

Phe Leu Ile Trp Leu Lys Asp Asn Gly Ile Ser Arg Phe Glu Ser Thr
465                 470                 475                 480

Glu Glu Val Glu Arg Glu Trp Arg Ala His Val Asp Asp Ile Phe Val
                485                 490                 495
```

```
Asn Ser Leu Phe Pro Lys Ala Lys Ser Trp Tyr Trp Gly Ala Asn Val
            500                 505                 510

Pro Gly Lys Pro Ala Gln Met Leu Asn Tyr Ser Glu Ala Ser Pro His
        515                 520                 525

Ile

<210> SEQ ID NO 23
<211> LENGTH: 339
<212> TYPE: DNA
<213> ORGANISM: Brevibacterium sp HCU

<400> SEQUENCE: 23
atgcgcacac tcgaccaccc cagcagggac gagatgagac tcgacaccgt cctggccgcc      60
ctcgccgacc cggtccgccg caccgtcgcc tgcaaactca acgacgcttt cggcgatcat     120
gcgtgtgcga ccttcgagct gccggtgtcg aagtccacgg cgacctatca cttccgcact     180
ctgcgcgaag cggggggtgat ccgccaggaa tatgagggca cgaagatcat gaatacctgc     240
gcaaggacga ttgacgcccg ctttcccggc tctggacgcg tgttcgccgc ccaggacatc     300
gaacgcgccg aggcggccgc ccccgaatct cacgactga                              339

<210> SEQ ID NO 24
<211> LENGTH: 112
<212> TYPE: PRT
<213> ORGANISM: Brevibacterium sp HCU

<400> SEQUENCE: 24

Met Arg Thr Leu Asp His Pro Ser Arg Asp Glu Met Arg Leu Asp Thr
  1               5                  10                  15

Val Leu Ala Ala Leu Ala Asp Pro Val Arg Arg Thr Val Ala Cys Lys
               20                  25                  30

Leu Asn Asp Ala Phe Gly Asp His Ala Cys Ala Thr Phe Glu Leu Pro
            35                  40                  45

Val Ser Lys Ser Thr Ala Thr Tyr His Phe Arg Thr Leu Arg Glu Ala
        50                  55                  60

Gly Val Ile Arg Gln Glu Tyr Glu Gly Thr Lys Ile Met Asn Thr Cys
 65                  70                  75                  80

Ala Arg Thr Ile Asp Ala Arg Phe Pro Gly Ser Gly Arg Val Phe Ala
                85                  90                  95

Ala Gln Asp Ile Glu Arg Ala Glu Ala Ala Pro Glu Ser His Asp
            100                 105                 110

<210> SEQ ID NO 25
<211> LENGTH: 1074
<212> TYPE: DNA
<213> ORGANISM: Brevibacterium sp HCU

<400> SEQUENCE: 25
atgtctcatc tgctgttcga accgctcaca ctgcgcggcc tgaccttccg caatcggatc      60
tgggttccgc ccatgtgcca gtactccgtc gagactctag acgggtccc cgctccttgg      120 cacaccgtcc actacggtgc gatggcccgc ggcggagccg gcgccgtcat cgtcgaagcc     180
accggagtcg ctccggaggc gcgcatctcg gccaaggatc tgggctggaa cgacgaacag     240
cgcgacgcct tcgtccccat cgtcgacttc ctccacaccc agggcgcggc cgccggcatc     300
cagctcgccc acgccggccg caaggcctcg acctatccgg agtggggaac cgaccgcgac     360
ggcagcctgc ccgtcgacga aggcggttgg cagaccgtgg ctccgtccgc actggccttc     420
```

-continued

```
gacggcctcg ccgaaccgcg agcactgacc gaaacagaga tcgccgaggt ggtcgcggcc      480
ttccggtcct cggcccgccg ggcgatcgag gccgggttcg acttcgtcga gatccacgcc      540
gcacacggat acctcctcca tgagttcctg tcgcccctga gcaacaaccg caccgactcc      600 tacgcggat  ccttggagaa ccgggcccga ctgctgctcg acatcgtcga tgccacccgc      660
accgaggtgg gcgaggacgt tcccgtgttc gtgcgcctct ccgcgacgga ctggacagaa      720
ggcgggctca cgctcgacga cacagtggag gtcgccggat ggctcaagga acacggtgtc      780
gacctcatcg acgtctcctc cggcggcaat gtgatggcgt cgattcccgt cggtcccggc      840
taccagacga ccctggccgc cggcgtgcgg cagggatcgg ggctgccgac cgcggccgtc      900
ggcctcatca gcgaaccgtt ccagggcgag cacattctgg ccaccggcca ggccgatgtg      960
atcctcgtgg ccgtgagta  cctccgcgat ccgaacttcg cgctgcgcgc cgccgacgcc     1020
ctgcgcttcg acatcgacta ccgcccggct cagtaccacc gcgcgtataa gtga           1074
```

<210> SEQ ID NO 26
<211> LENGTH: 357
<212> TYPE: PRT
<213> ORGANISM: Brevibacterium sp HCU

<400> SEQUENCE: 26

```
Met Ser His Leu Leu Phe Glu Pro Leu Thr Leu Arg Gly Leu Thr Phe
  1               5                  10                  15

Arg Asn Arg Ile Trp Val Pro Pro Met Cys Gln Tyr Ser Val Glu Thr
             20                  25                  30

Leu Asp Gly Val Pro Ala Pro Trp His Thr Val His Tyr Gly Ala Met
         35                  40                  45

Ala Arg Gly Gly Ala Gly Ala Val Ile Val Glu Ala Thr Gly Val Ala
     50                  55                  60

Pro Glu Ala Arg Ile Ser Ala Lys Asp Leu Gly Trp Asn Asp Glu Gln
 65                  70                  75                  80

Arg Asp Ala Phe Val Pro Ile Val Asp Phe Leu His Thr Gln Gly Ala
                 85                  90                  95

Ala Ala Gly Ile Gln Leu Ala His Ala Gly Arg Lys Ala Ser Thr Tyr
            100                 105                 110

Pro Glu Trp Gly Thr Asp Arg Asp Gly Ser Leu Pro Val Asp Glu Gly
        115                 120                 125

Gly Trp Gln Thr Val Ala Pro Ser Ala Leu Ala Phe Asp Gly Leu Ala
    130                 135                 140

Glu Pro Arg Ala Leu Thr Glu Thr Glu Ile Ala Glu Val Val Ala Ala
145                 150                 155                 160

Phe Arg Ser Ser Ala Arg Arg Ala Ile Glu Ala Gly Phe Asp Phe Val
                165                 170                 175

Glu Ile His Ala Ala His Gly Tyr Leu Leu His Glu Phe Leu Ser Pro
            180                 185                 190

Leu Ser Asn Asn Arg Thr Asp Ser Tyr Gly Gly Ser Leu Glu Asn Arg
        195                 200                 205

Ala Arg Leu Leu Leu Asp Ile Val Asp Ala Thr Arg Thr Glu Val Gly
    210                 215                 220

Glu Asp Val Pro Val Phe Val Arg Leu Ser Ala Thr Asp Trp Thr Glu
225                 230                 235                 240

Gly Gly Leu Thr Leu Asp Asp Thr Val Glu Val Ala Gly Trp Leu Lys
                245                 250                 255

Glu His Gly Val Asp Leu Ile Asp Val Ser Ser Gly Gly Asn Val Met
```

-continued

```
                260             265             270
Ala Ser Ile Pro Val Gly Pro Gly Tyr Gln Thr Thr Leu Ala Ala Gly
        275                     280                 285

Val Arg Gln Gly Ser Gly Leu Pro Thr Ala Ala Val Gly Leu Ile Ser
        290                     295                 300

Glu Pro Phe Gln Gly Glu His Ile Leu Ala Thr Gly Gln Ala Asp Val
305                     310                 315                 320

Ile Leu Val Gly Arg Glu Tyr Leu Arg Asp Pro Asn Phe Ala Leu Arg
                325                 330                 335

Ala Ala Asp Ala Leu Arg Phe Asp Ile Asp Tyr Arg Pro Ala Gln Tyr
            340                 345                 350

His Arg Ala Tyr Lys
        355

<210> SEQ ID NO 27
<211> LENGTH: 2200
<212> TYPE: DNA
<213> ORGANISM: Brevibacterium sp HCU

<400> SEQUENCE: 27
gctgagctca attcgctgga gcggctcggc gctcatacgc tgacggccca gttgaagtcg      60
acagcaatgt tcaaatgtgt gctgtccgac ttcaactggg ccgttggcgt ctgtcatctg     120
cgcggacagc gctcgccgag ggtgagcgtg tggagatgtg gctgagctca gaacggtcgg     180
ttgcagctag gccaggcctc cgagccacat tccgatcgcc gcggccgtcg tggtgagaac     240
gagggtgccg agcgcgttga ccaggccggc ggcccagcga cgttcctgga gaagccggac     300
cgtttcgaag ctcgccgtcg aaaacgtcgt atagccgccg aggaatcccg tgccgagcac     360
caggtgccag gcttgcggaa gcaggttcgc tccggccagt ccggtcagca ggccgagcac     420
gagtgatccc gagacattga tgatgatcgt tccccacggc agggccgtgc tcatgcggga     480
cttgatgagt ccgtcgatca gcattcgtga tgaggcgccg agtccgccgg cggcggcaag     540
ggcgacgaag accagcggcg tcatcgggca cctcctcgac gcagcgtcgt cgccgtggcg     600
atgccggcga acgtggcgag accgccgatg agtaccgtgc ccaccgcgta ggcaatcccg     660
atgccggggc tgctcgcccc acccggaccc gcgccgaggc ggcccgccgt atcggcggcc     720
agcgcgctgt atgtggtgaa tccgcccatg aaaccggtgc cgaccaggat ccgcgttcgg     780
cgacgccacc tttcatcggg gccgctgcgc gccagggaat ccaacagcag gccgagcaga     840
aacgccccga ggatgttgac cgtgaggatt gcccacggca tcgccgaggg ggcggcagg      900
ctcaggctga tcgcctcgcg tgccgcagtt ccgactgcgc cgccgatgaa cgcgagcccc     960
agataggaca ggcgcaggtg gactggccgg gtcactgttc gcccgcgccg gcttgagtct    1020
cggcagcggg ggaagcgcca ggggtcggcg acgtcgcagg ggattcgggg ttgcccatgt    1080
cgtcggtgcc tgtcgccagc ggaacgacga cgagggggcg atgctggcgc cttgacagtt    1140
ggatcgcgac cgagccattg aagaactcat gcagtgagcc gcgaacacct gcgcgacgga    1200
cgccgaggat gatcatgcgg gcatcgagcg cctcggcgag ccggtcgagt tcctgtgccg    1260
gtgacccggc cagtgcgcgg gtcgaccagg caacattcgt gccttccagg gctacagcga    1320
tgcggtcctg gagttcgggg tcgaactcgg tggctgcctc gtcggtggtg tccgatcga    1380
tgggcatcga gagcacggag ccgtcgggac gagtctcaac ggtgtatcgg gagtcgtcga    1440
cgtgggcgca gacgaactcg gcgtccaagt gggcgacgta gtccgcgcg gcggcgatca    1500
cctcggcggg ctgatcgggg acgacgccga ggatgatgcg ggcgcgcggc ggcccgtcgt    1560
```

```
atatcggatc ggggctggcg gtcatggtct ctcctacctt tcgggcatgc tgaagccgtc    1620
cgaggtaagg gactgttttc gaagacgaac accgaaggtt ccgcttccga gttgggtacg    1680
gcgagcccca ccgccgtgcc gcgcagtcgc gacaccaata ttgtgccaca ggaccatagc    1740
gaaagggccg tcggacggcc ggcatccgaa gatggccggc atcccgacgg ccccgctgg     1800 ggtatcagcg ctcgtgggac tcacccttcg cggatcgtca tcctgctcag tttgtcgccg    1860
tcgatgacga aggcgaacga tgaccgaccg ttggcgtgcg tggagcgcca atcgccgatg    1920
atggtgacgt cgtttccgtc gacggtgact cttcgggcgt gaggacgccg gttgcaccga    1980
tgaattcctt atcgctccag gccttgatgg cctcccggcc ctggaactcg cgtccccagt    2040
cgtcgacagt gccatcgggg gtgaatgcgt ccaggaagcc ctggttgtcg tgagcgttga    2100
cggtgtcgat gaagccggcg acgggttcgg gaatctgcag gtctgacata tgtgctcctg    2160
tgctgttgag atatgtgctg tcgggatgtg gttgtcgatc                          2200
```

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 28

```
gagtttgatc ctggctcag                                                   19
```

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: unsure
<222> LOCATION: (5)
<223> OTHER INFORMATION: m stands for nucleotide base A or C
<220> FEATURE:
<221> NAME/KEY: unsure
<222> LOCATION: (17)
<223> OTHER INFORMATION: w stands for nucleotide base A or T

<400> SEQUENCE: 29

```
caggmgccgc ggtaatwc                                                    18
```

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 30

```
gctgcctccc gtaggagt                                                    18
```

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 31

```
ctaccagggt aactaatcc                                                   19
```

<210> SEQ ID NO 32
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 32
acgggcggtg tgtac                                                        15

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 33
cacgagctga cgacagccat                                                   20

<210> SEQ ID NO 34
<211> LENGTH: 16
<212> TYPE: DNA
<213> ORGANISM: Artificial Sequence
<220> FEATURE:
<223> OTHER INFORMATION: Description of Artificial Sequence: primer

<400> SEQUENCE: 34
taccttgtta cgactt                                                       16

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: unsure
<222> LOCATION: (2)
<223> OTHER INFORMATION: w stands for nucleotide base A or T
<220> FEATURE:
<221> NAME/KEY: unsure
<222> LOCATION: (14)
<223> OTHER INFORMATION: k stands for nucleotide base G or T

<400> SEQUENCE: 35
gwattaccgc ggckgctg                                                     18

<210> SEQ ID NO 36
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 36
ggattagata ccctggtag                                                    19

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 37
atggctgtcg tcagctcgtg                                                   20

```
<210> SEQ ID NO 38
<211> LENGTH: 17
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: unsure
<222> LOCATION: (14)..(17)
<223> OTHER INFORMATION: v stands for any combination of A, C, or G
      at the last 4 positions at the 3' end

<400> SEQUENCE: 38
cggagcagat cgavvvv                                                 17

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 39
gatccaccaa gttcctcc                                                18

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 40
cccggtaaat cacgtgagta ccacg                                        25

<210> SEQ ID NO 41
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 41
gaaagatcga ggatccatgc caattacaca ac                                32

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 42
tcgagcaagc ttggctgcaa                                              20

<210> SEQ ID NO 43
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 43
tcgaaggagg aggcatgcat gacgtcaacc                                   30
```

<210> SEQ ID NO 44
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 44
cagcagggac aagcttagac tcgaca                                    26

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 45
atgaaagcat tcgcaatgaa ggca                                      24

<210> SEQ ID NO 46
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 46
ccgcacggaa cccgtctcc                                            19

<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 47
atggagtcgc acaacgaaaa cac                                       23

<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 48
gctcactcgg cccaccagc                                            19

<210> SEQ ID NO 49
<211> LENGTH: 1388
<212> TYPE: DNA
<213> ORGANISM: Brevibacterium sp HCU

<400> SEQUENCE: 49
cgcccttgag tttgatcctg gctcaggacg aacgctggct gcgtgcttaa cacatgcaag    60
tcgaacgctg aagccgacag cttgctgttg gtggatgagt ggcgaacggg tgagtaacac   120
gtgagtaacc tgcccctgat ttcgggataa gcctgggaaa ctgggtctaa taccggatac   180
gaccacctga cgcatgttgg gtggtggaaa gttttcgat cggggatggg ctcgcggcct   240
atcagcttgt tggtggggta atggcctacc aaggcgacga cgggtagccg gcctgagagg   300
gcgaccggcc acactgggac tgagacacgg cccagactcc tacgggaggc agcagtgggg   360

```
aatattgcac aatgggggaa accctgatgc agcgacgcag cgtgcgggat gacggccttc    420
gggttgtaaa ccgctttcag cagggaagaa gcgaaagtga cggtacctgc agaagaagta    480
ccggctaact acgtgccagc agccgcggta atacgtaggg tacgagcgtt gtccggaatt    540
attgggcgta aagagctcgt aggtggttgg tcacgtctgc tgtggaaacg caacgcttaa    600
cgttgcgcgt gcagtgggta cgggctgact agagtgcagt aggggagtct ggaattcctg    660
gtgtagcggt gaaatgcgca gatatcagga ggaacaccgg tggcgaaggc gggactctgg    720
gctgtaactg acactgagga gcgaaagcat ggggagcgaa caggattaga taccctggta    780
gtccatgccg taaacgttgg gcactaggtg tgggggacat tccacgttct ccgcgccgta    840
gctaacgcat aagtgcccc gcctggggag tacggtcgca aggctaaaac tcaaaggaat     900
tgacggggc ccgcacaagc ggcggagcat gcggattaat tcgatgcaac gcgaagaacc    960
ttaccaaggc ttgacataca ctggaccgtt ctggaaacag ttcttctctt tggagctggt   1020
gtacaggtgg tgcatggttg tcgtcagctc gtgtcgtgag atgttgggtt aagtcccgca   1080
acgagcgcaa ccctcgttct atgttgccag cacgtgatgg tgggaactca taggagactg   1140
ccggggtcaa ctcggaggaa ggtggggatg acgtcaaatc atcatgccct ttatgtcttg   1200
ggcttcacgc atgctacaat ggctggtaca gagagaggcg aacccgtgag ggtgagcgaa   1260
tcccttaaag ccagtctcag ttcggatcgt agtctgcaat tcgactacgt gaagtcggag   1320
tcgctagtaa tcgcagatca gcaacgctgc ggtgaatacg ttcccgggcc ttgtacacac   1380
cgcccgta                                                            1388
```

OXIDATION OF A CYCLOHEXANONE DERIVATIVE USING A BREVIBACTERIUM CYCLOHEXANONE MONOOXYGENASE

This is a Divisional case claiming to priority to U.S. Ser. No. 09/954,314, filed Sep. 17, 2001, now U.S. Pat. No. 6,465,224 which is a Divisional of appl. Ser. No. 09/504,358, U.S. Pat. No. 6,365,376 filed Feb. 15, 2000 now issued, which claims the benefit of U.S. Provisional Application No. 60/120,702, filed Feb. 19, 1999 now abandoned.

FIELD OF THE INVENTION

The invention relates to the field of molecular biology and microbiology. More specifically, genes have been isolated from Brevibacterium sp HCU and sequences that encode for enzymes useful for production of intermediates in the adipic acid biosynthetic pathway or for the production of related molecules.

BACKGROUND OF THE INVENTION

Production of adipic acid in the U.S. was 1.96 billion pounds in 1997 with an estimated 2.0 billion pounds in 1998. Historically the demand for adipic acid has grown 2% per year and 1.5–2% is expected through the year 2002. Adipic acid consistently ranks as one of the top fifty chemicals produced domestically. Nearly 90% of domestic adipic acid is used to produce nylon-6,6. Other uses of adipic acid include production of lubricants and plasticizers, and as a food acidulant.

The dominant industrial process for synthesizing adipic acid employs initial air oxidation of cyclohexane to yield a mixture of cyclohexanone (ketone) and cyclohexanol (alcohol), which is designated KA (see for example U.S. Pat. No. 5,221,800). Hydrogenation of phenol to yield KA is also used commercially, although this process accounts for just 2% of all adipic acid production. KA produced via both methods is oxidized with nitric acid to produce adipic acid. Reduced nitrogen oxides including $NO_2$, NO, and $N_2O$ are produced as by-products and are recycled back to nitric acid at varying levels.

Research has also focused on synthesis of adipic acid from alternative feedstocks. Significant attention has been directed at carbonylation of butadiene (U.S. Pat. No. 5,166,421). More recently, a method of dimerizing methyl acrylates was reported, opening up the possibility of adipic acid synthesis from C-3 feedstocks.

These processes are not entirely desirable due to their heavy reliance upon environmentally sensitive feedstocks, and their propensity to yield undesirable by-products. Non-synthetic, biological routes to adipic acid would be more advantageous to industry and beneficial to the environment.

A number of microbiological routes are known. Wildtype and mutant organisms have been shown to convert renewable feedstocks such as glucose and other hydrocarbons to adipic acid [Frost, John, Chem. Eng. (Rugby, Engl.) (1996), 611, 32–35; WO 9507996; Steinbuechel, AlexanderCLB Chem. Labor Biotech. (1995), 46(6), 277–8; Draths et al., ACS Symp. Ser. (1994), 577 (Benign by Design), 32–45; U.S. Pat. No. 4,400,468; JP 49043156 B4; and DE 2140133]. Similarly, organisms possessing nitrilase activity have been shown to convert nitriles to carboxylic acids including adipic acid [Petre et al., AU 669951; CA 2103616].

Additionally, wildtype organisms have been used to convert cyclohexane and cyclohexanol and other alcohols to adipic acid [JP 01023894 A2; Cho, Takeshi et al., Bio Ind. (1991), 8(10), 671–8; Horiguchi et al., JP 01023895 A2; JP 01023894 A2; JP 61128890 A; Hasegawa et al., Biosci., Biotechnol., Biochem. (1992), 56(8), 1319–20; Yoshizako et al., J. Ferment. Bioeng. (1989), 67(5), 335–8; Kim et al., Sanop Misaengmul Hakhoechi (1985), 13(1), 71–7; Donoghue et al., Eur. J. Biochem. (1975), 60(1), 1–7].

One enzymatic pathway for the conversion of cyclohexanol to adipic acid has been suggested as including the intermediates cyclohexanol, cyclohexanone, 2-hydroxycyclohexanone, ε-caprolactone, 6-hydroxycaproic acid, and adipic acid. Some specific enzyme activities in this pathway have been demonstrated, including cyclohexanol dehydrogenase, NADPH-linked cyclohexanone oxygenase, ε-caprolactone hydrolase, and NAD (NADP)-linked 6-hydroxycaproic acid dehydrogenase (Tanaka et al., Hakko Kogaku Kaishi (1977), 55(2), 62–7). An alternate enzymatic pathway has been postulated to comprise cyclohexanol→cyclohexanone→1-oxa-2-oxocycloheptane→6-hydroxyhexanoate→6-oxohexanoate→adipate [Donoghue et al., Eur. J. Biochem. (1975), 60(1), 1–7]. The literature is silent on the specific gene sequences encoding the cyclohexanol to adipic acid pathway, with the exception of the monoxygenase, responsible for the conversion of cyclohexanone to caprolactone, [Chen,et al., J. Bacteriol., 170, 781–789 (1988)].

The problem to be solved, therefore is to provide a synthesis route for adipic acid which not only avoids reliance on environmentally sensitive starting materials but also makes efficient use of inexpensive, renewable resources. It would further be desirable to provide a synthesis route for adipic acid which avoids the need for significant energy inputs and which minimizes the formation of toxic by-products.

Applicants have solved the stated problem by identifying, isolating and cloning a two unique monooxygenase genes, a hydrolase gene, a hydroxycaproate dehydrogenase gene, a cyclohexanol dehydrogenase gene and a gene encoding an acyl-CoA dehydrogenase, all implicated in the adipic acid biosynthetic pathway.

SUMMARY OF THE INVENTION

The invention provides an isolated nucleic acid fragment encoding an adipic acid synthesizing protein selected from the group consisting of: (a) an isolated nucleic acid molecule encoding the amino acid sequence set forth in SEQ ID NO:2, SEQ ID NO:4, SEQ ID NO:6, SEQ ID NO:8, SEQ ID NO:12, SEQ ID NO:14, SEQ ID NO:18, SEQ ID NO:20, SEQ ID NO:22, and SEQ ID NO:24; (b) an isolated nucleic acid molecule that hybridizes with (a) under the following hybridization conditions: 0.1×SSC, 0.1% SDS at 65° C.; and washed with 2×SSC, 0.1% SDS followed by 0.1×SSC, 0.1% SDS; (c) an isolated nucleic acid molecule that is completely complementary to (a) or (b).

In another embodiment the invention provides methods for the isolation of nucleic acid fragments substantially similar to those encoding the polypeptides as set forth in SEQ ID NO:2, SEQ ID NO:4, SEQ ID NO:6, SEQ ID NO:8, SEQ ID NO:12, SEQ ID NO:14, SEQ ID NO:18, SEQ ID NO:20, SEQ ID NO:22, and SEQ ID NO:24 based on the partial sequence of the nucleic acid fragments.

The invention further provides a method for the production of adipic acid comprising: contacting a transformed host cell under suitable growth conditions with an effective amount of cyclohexanol whereby adipic acid is produced, the transformed host cell containing the nucleic acid fragments as set forth in SEQ ID NO:15 and SEQ ID NO:16.

The invention additionally provides methods for the production of intermediates in the pathway for the synthesis of adipic acid from cyclohexanol comprising transformed organisms transformed with any one of the open reading frames encoding SEQ ID NO:4, SEQ ID NO:6, SEQ ID NO:8, SEQ ID NO:12, SEQ ID NO:14, SEQ ID NO:18, and SEQ ID NO:22.

Additionally the invention provides for recombinant cells transformed with any gene encoding the polypeptides selected from the group consisting of SEQ ID NO:4, SEQ ID NO:6, SEQ ID NO:8, SEQ ID NO:12, SEQ ID NO:14, SEQ ID NO:18, SEQ ID NO:22, and SEQ ID NO:24.

The invention further provides an isolated Brevibacterium sp HCU containing the genes required for the production of adipic acid intermediates as identified by its 16s rDNA profile.

BRIEF DESCRIPTION OF THE DRAWINGS, SEQUENCE DESCRIPTIONS AND BIOLOGICAL DEPOSITS

Figure 1:
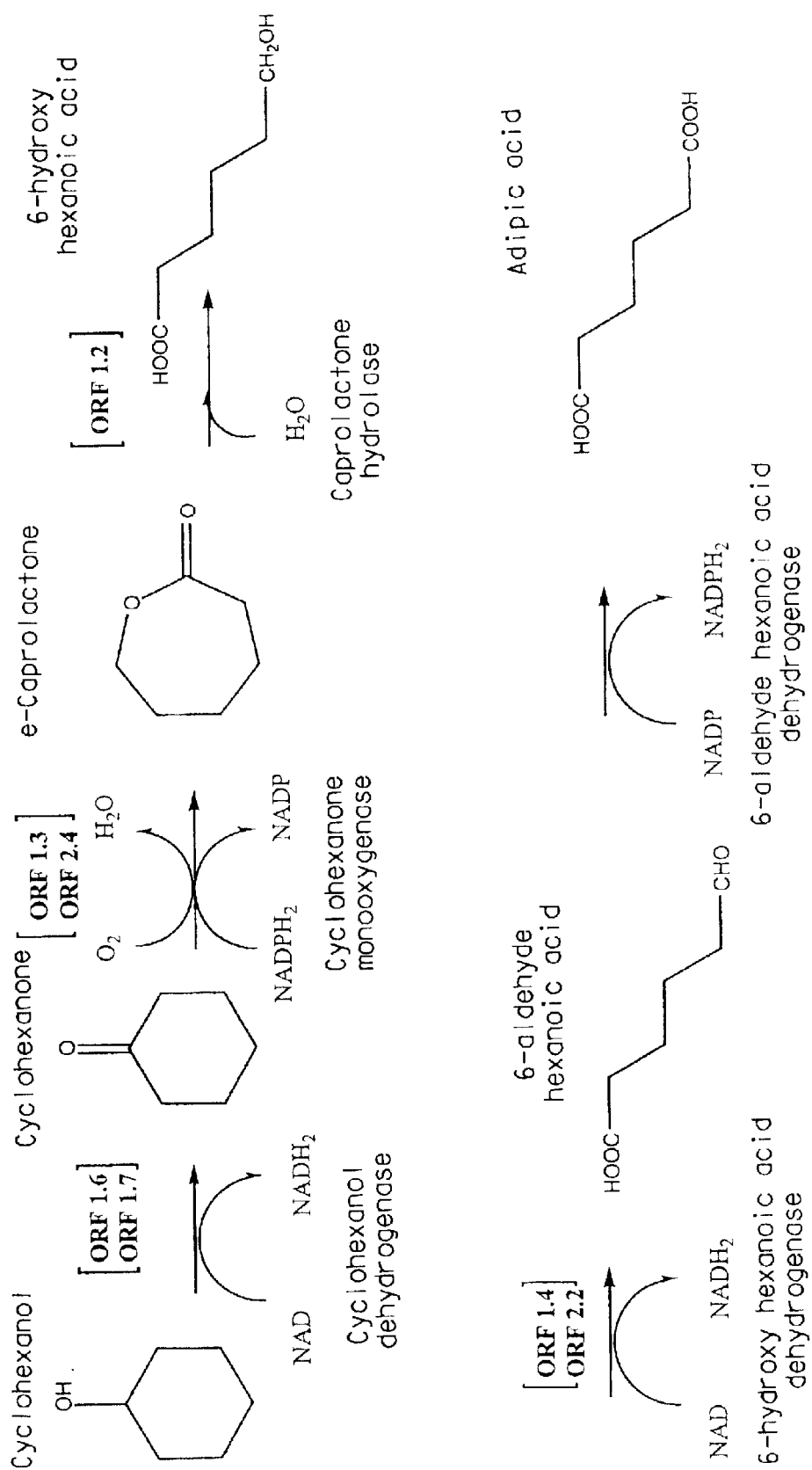
FIG. 1 is a diagram showing the pathway for the conversion of cyclohexanol to adipic acid, and the corresponding ORF's encoding the relevant enzymes.

The invention can be more fully understood from the following detailed description and the accompanying sequence descriptions which form a part of this application.

The following sequence descriptions and sequences listings attached hereto comply with the rules governing nucleotide and/or amino acid sequence disclosures in patent applications as set forth in 37 C.F.R. §1.821–1.825. The Sequence Descriptions contain the one letter code for nucleotide sequence characters and the three letter codes for amino acids as defined in conformity with the IUPAC-IYUB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

SEQ ID NO:1 is the nucleotide sequence of ORF 1.1 isolated from gene cluster 1 (GC-1) from Brevibacterium sp HCU and encoding a regulator element, the element being most similar to a transcription factor.

SEQ ID NO:2 is deduced amino acid sequence of ORF 1.1, encoded by SEQ ID NO:1.

SEQ ID NO:3 is the nucleotide sequence of ORF 1.2 isolated from gene cluster 1 (GC-1) from Brevibacterium sp HCU and encoding a hydrolase enzyme, the enzyme being most similar to a Streptomyces acetyl-hydrolase.

SEQ ID NO:4 is the deduced amino acid sequence of ORF 1.2, encoded by SEQ ID NO:3.

SEQ ID NO:5 is the nucleotide sequence of ORF 1.3 isolated from gene cluster 1 (GC-1) from Brevibacterium sp HCU and encoding a monooxygenase enzyme, the enzyme being most similar to an Acinetobacter monooxygenase.

SEQ ID NO:6 is the deduced amino acid sequence of ORF 1.3, encoded by SEQ ID NO:5.

SEQ ID NO:7 is the nucleotide sequence of ORF 1.4 isolated from gene cluster 1 (GC-1) from Brevibacterium sp HCU and encoding an alcohol dehydrogenase, the enzyme being most similar to an Bacillus methanol dehydrogenase.

SEQ ID NO:8 is the deduced amino acid sequence of ORF 1.4, encoded by SEQ ID NO:7.

SEQ ID NO:9 is the nucleotide sequence of ORF 1.5 isolated from gene cluster 1 (GC-1) from Brevibacterium sp HCU and encoding a hydroxyacyl CoA dehydrogenase, the enzyme being most similar to an Archaeoglobus 3-hydroxyacyl CoA dehydrogenase.

SEQ ID NO:10 is the deduced amino acid sequence of ORF 1.5, encoded by SEQ ID NO:9.

SEQ ID NO:11 is the nucleotide sequence of ORF 1.6 isolated from gene cluster 1 (GC-1) from Brevibacterium sp HCU and encoding an alcohol dehydrogenase, the enzyme being most similar to an Sphingomonas 2,5-Dichloro-2,5-cyclohexadienel,4-diol dehydrogenase.

SEQ ID NO:12 is the deduced amino acid sequence of ORF 1.6, encoded by SEQ ID NO:11.

SEQ ID NO:13 is the nucleotide sequence of ORF 1.7 isolated from gene cluster 1 (GC-1) from Brevibacterium sp HCU and encoding an alcohol dehydrogenase, the enzyme being most similar to an Streptomyces beta-hydroxy-steroid dehydrogenase.

SEQ ID NO:14 is the deduced amino acid sequence of ORF 1.7, encoded by SEQ ID NO:13, where the N-terminal sequence is highly similar to that of the cyclohexanol dehydrogenase from Arthrobacter (Cho, Takeshi et al.,*Bio Ind.* (1991), 8(10), 671–8).

SEQ ID NO:15 is the complete nucleotide sequence of gene cluster 1 isolated from gene from Brevibacterium sp HCU.

SEQ ID NO:16 is the complete nucleotide sequence of gene cluster 2 isolated from gene from Brevibacterium sp HCU.

SEQ ID NO:17 is the nucleotide sequence of ORF 2.2 isolated from gene cluster 2 (GC-2) from Brevibacterium sp HCU and encoding an alcohol dehydrogenase, the enzyme being most similar to an Sulfolobus alcohol dehydrogenase.

SEQ ID NO:18 is the deduced amino acid sequence of ORF 2.2, encoded by SEQ ID NO:17.

SEQ ID NO:19 is the nucleotide sequence of ORF 2.3 isolated from gene cluster 2 (GC-2) from Brevibacterium sp HCU and encoding a regulator gene, the gene product being most similar to an transcription factor.

SEQ ID NO:20 is the deduced amino acid sequence of ORF 2.3, encoded by SEQ ID NO:19.

SEQ ID NO:21 is the nucleotide sequence of ORF 2.4 isolated from gene cluster 2 (GC-2) from Brevibacterium sp HCU and encoding a monooxygenase, the enzyme being most similar to an Rhodococcus monooxygenase.

SEQ ID NO:22 is the deduced amino acid sequence of ORF 2.4, encoded by SEQ ID NO:20.

SEQ ID NO:23 is the nucleotide sequence of ORF 2.5 isolated from gene cluster 2 (GC-2) from Brevibacterium sp HCU and encoding a small transcriptional regulator which has homology to the ArsR family of regulators.

SEQ ID NO:24 is the deduced amino acid sequence of ORF 2.5, encoded by SEQ ID NO:23.

SEQ ID NO:25 is the nucleotide sequence of ORF 2.6 isolated from gene cluster 2 (GC-2) from Brevibacterium sp HCU and encoding a oxidoreductatse, the enzyme being most similar to an Bacillus NADH-dependent flavin oxidoreductase.

SEQ ID NO:26 is the deduced amino acid sequence of ORF 2.6, encoded by SEQ ID NO:25.

SEQ ID NO:27 is the nucleotide sequence of ORF 2.7 isolated from gene cluster 2 (GC-2) from Brevibacterium sp HCU and encoding an unknown protein.

SEQ ID NO's:28–44 correspond to primers used to amplify and clone genes and for 16s RNA identification of the Brevibacterium sp HCU.

SEQ ID NO's:45–48 are PCR primers used to amplify various ORF's for expression studies.

SEQ ID NO:49 is the 16s rDNA sequence of the isolated Brevibacterium sp HCU having GC-1 or GC-2.

DETAILED DESCRIPTION OF THE INVENTION

The present invention provides new sequences encoding key enzymes in the synthesis of adipic acid from cyclohexanol. The genes and their expression products are useful for the creation of recombinant organisms that have the ability to produce adipic acid while growing on cyclohexanol or intermediates in this oxidation pathway, and for the identification of new species of bacteria having the ability to produce adipic acid. Full length sequence for 14 ORF's from two separate gene clusters have been obtained. Eleven have been identified by comparison to public databases containing nucleotide and protein sequences using the BLAST algorithms well known to those skilled in the art. Seven of the relevant ORF's all reside on a single gene cluster termed here "gene cluster 1" or "GC-1". This cluster contains ORF's 1.1–1.7. Gene cluster 2 (GC-2) also contains 7 ORF's, identified as 2.1–2.7.

In this disclosure, a number of terms and abbreviations are used. The following definitions are provided.

"Open reading frame" is abbreviated ORF.

"Polymerase chain reaction" is abbreviated PCR.

"High performance liquid chromatography" is abbreviated HPLC.

"Gas chromatography" is abbreviated GC.

"Mass spectrometry" is abbreviated MS.

"High performance liquid chromatography coupled with mass spectrometry" is abbreviated LC/MS.

The term "cycloalkanone derivative" refers to any molecule containing a complete oxidized or derivatized cycloalkanone substructure, including but not limited to cyclobutanone, cyclopentanone, cyclohexanone, 2-methylcyclo-pentanone, 2-methylcyclohexanone, cyclohex-2-ene-1-one, 2-(cyclohex-1-enyl)cyclohexanone, 1,2-cyclohexanedione, 1,3-cyclohexanedione, and 1,4-cyclohexanedione.

"HCU" is the abbreviation for "Halophilic Cyclohexanol Utilizer" and is used to identify the unique Brevibacterium sp. strain of the instant invention The term "adipic acid biosynthetic pathway" will mean and enzyme mediated conversion of cyclohexanol to adipic acid comprising the conversion of:
(1) cyclohexanol to cyclohexanone via cyclohexanol dehydrogenase,
(2) cyclohexanone to ϵ-caprolactone via cyclohexanone monooxygenase
(3) ϵ-caprolactone to 6-hydroxy hexanoic acid via caprolactone hydrolase,
(4) 6-hydroxy hexanoic acid to 6-aldehyde hexanoic acid via 6-hydroxy hexanoic acid dehydrogenase, (5) 6-aldehyde hexanoic acid to adipic acid via 6-aldehyde hexanoic acid dehydrogenase.

"Regulator" as used herein refers to a protein that modifies the transcription of a set of genes under its control.

"Cyclohexanol dehydrogenase" refers to an enzyme that catalyzes the conversion of cyclohexanol to cyclohexanone. Within the context of the present invention this enzyme is encoded by ORF 1.6 or ORF 1.7 resident on GC-1.

"Cyclohexanone monooxygenase" refers to an enzyme that catalyzes the conversion of cyclohexanone to c-caprolactone. Within the context of the present invention this enzyme is encoded by one of two ORF's, ORF 1.3 (resident on GC-1) or ORF 2.4 (resident on GC-2).

"Caprolactone hydrolase" refers to an enzyme that catalyzes the conversion of caprolactone to 6-alcohol hexanoic acid. Within the context of the present invention this enzyme is encoded by ORF 1.2 and is resident on GC-1.

"6-hydroxy hexanoic acid dehydrogenase" refers to an enzyme that catalyzes the conversion of 6-hydroxy hexanoic acid to 6-aldehyde hexanoic acid. Within the context of the present invention this enzyme is encoded by ORF 2.2 and is resident on GC-2.

The term "gene cluster" will mean genes organized in a single expression unit or in close proximity on the chromosome.

The term "Gene cluster 1" or "GC-1" refers to the 10.6 kb gene cluster comprising ORF's 1.1.–1.7 useful in generating intermediates in the adipic acid biosynthetic pathway.

The term "Gene cluster 2" or "GC-2" refers to the 11.5 kb gene cluster comprising ORF 2.1–2.7, useful in generating intermediates in the adipic acid biosynthetic pathway.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

The term "adipic acid synthesizing protein" means the gene product of any of the sequences set forth in SEQ ID NO:1, SEQ ID NO:3, SEQ ID NO:5, SEQ ID NO:7, SEQ ID NO:9, SEQ ID NO:1, SEQ ID NO:13, SEQ ID NO:17, SEQ ID NO:19, SEQ ID NO:21, SEQ ID NO:23, and SEQ ID NO:25.

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotide bases that do not substantially affect the functional properties of the resulting transcript. It is therefore understood that the invention encompasses more than the specific exemplary sequences.

For example, it is well known in the art that alterations in a gene which result in the production of a chemically equivalent amino acid at a given site, but do not effect the functional properties of the encoded protein are common. Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product. Nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products. Moreover, the skilled artisan recognizes that substantially similar sequences encompassed by this invention are also defined by their ability to hybridize, under stringent conditions (0.1×SSC, 0.1% SDS, 65° C. and washed with 2×SSC, 0.1% SDS followed by 0.1×SSC, 0.1% SDS), with the sequences exemplified herein. Preferred substantially similar nucleic acid fragments of the instant invention are those nucleic acid fragments whose DNA sequences are at least 80% identical to the DNA sequence of the nucleic acid fragments reported herein. More preferred nucleic acid fragments are at least 90% identical to the DNA sequence of the nucleic acid fragments reported herein. Most preferred are nucleic acid fragments that are at least 95% identical to the DNA sequence of the nucleic acid fragments reported herein.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS. Moderate stringency hybridization conditions correspond to a higher $T_m$, e.g., 40% formamide, with 5×or 6×SSC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–9.51). For hybridizations with shorter nucleic acids, i.e., oligonucleotides, the position of mismatches becomes more important, and the length of the oligonucleotide determines its specificity (see Sambrook et al., supra, 11.7–11.8). In one embodiment the length for a hybridizable nucleic acid is at least about 10 nucleotides. Preferable a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

A "substantial portion" of an amino acid or nucleotide sequence comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215:403–410; see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches partial or complete amino acid and nucleotide sequences encoding one or more particular fungal proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable to hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing as well as those substantially similar nucleic acid sequences.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, New York (1988); *Biocomputing: Infor-* matics and Genome Projects (Smith, D. W., ed.) Academic Press, New York (1993); Computer Analysis of Sequence Data, Part I (Griffin, A. M., and Griffin, H. G., eds.) Humana Press, New Jersey (1994); Sequence Analysis in Molecular Biology (von Heinje, G., ed.) Academic Press (1987); and Sequence Analysis Primer (Gribskov, M. and Devereux, J., eds.) Stockton Press, New York (1991). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG Pileup program found in the GCG program package, as used in the instant invention, using the Needleman and Wunsch algorithm with their standard default values of gap creation penalty=12 and gap extension penalty=4 (Devereux et al., Nucleic Acids Res. 12:387–395 (1984)), BLASTP, BLASTN, and FASTA (Pearson et al., Proc. Natl. Acad. Sci. U.S.A. 85:2444–2448 (1988). The BLAST X program is publicly available from NCBI and other sources (BLAST Manual, Altschul et al., Natl. Cent. Biotechnol. Inf., Natl. Library Med. (NCBI NLM) NIH, Bethesda, Md. 20894; Altschul et al., J. Mol. Biol. 215:403–410 (1990)). Another preferred method to determine percent identity, is by the method of DNASTAR protein alignment protocol using the Jotun-Hein algorithm (Hein et al., Methods Enzymol. 183:626–645 (1990)). Default parameters for the Jotun-Hein method for alignments are: for multiple alignments, gap penalty=11, gap length penalty=3; for pairwise alignments ktuple=6. As an illustration, by a polynucleotide having a nucleotide sequence having at least, for example, 95% "identity" to a reference nucleotide sequence of SEQ ID NO:1 it is intended that the nucleotide sequence of the polynucleotide is identical to the reference sequence except that the polynucleotide sequence may include up to five point mutations per each 100 nucleotides of the reference nucleotide sequence of SEQ ID NO:1. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having an amino acid sequence having at least, for example, 95% identity to a reference amino acid sequence of SEQ ID NO:2 is intended that the amino acid sequence of the polypeptide is identical to the reference sequence except that the polypeptide sequence may include up to five amino acid alterations per each 100 amino acids of the reference amino acid of SEQ ID NO:2. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

"Codon degeneracy" refers to divergence in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the bacterial adipic acid synthesizing proteins as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:18, SEQ ID NO:22, SEQ ID NO:24, and SEQ ID NO:26. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that is not translated yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The terms "plasmid", "vector" and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et al., *Current Protocols in Molecular Biology*, published by Greene Publishing Assoc. and Wiley-Interscience (1987).

The nucleic acid fragments of the instant invention may be used to isolate cDNAs and genes encoding homologous enzymes from the same or other bacterial species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding similar enzymes to those of the instant adipic acid pathway, either as cDNAs or genomic DNAs, could be isolated directly by using all or a portion of the instant nucleic acid fragments as DNA hybridization probes to screen libraries from any desired bacteria using methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or full-length of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant ORF's may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding bacterial genes. Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., *PNAS USA* 86:5673 (1989); Loh et al., *Science* 243:217 (1989)).

Availability of the instant nucleotide and deduced amino acid sequences facilitates immunological screening cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner, R. A. *Adv. Immunol.* 36:1 (1984); Maniatis).

The enzymes and gene products of the instant ORF's may be produced in heterologous host cells, particularly in the cells of microbial hosts, and can be used to prepare antibodies to the resulting proteins by methods well known to those skilled in the art. The antibodies are useful for detecting the proteins in situ in cells or in vitro in cell extracts. Preferred heterologous host cells for production of the instant enzymes are microbial hosts. Microbial expression systems and expression vectors containing regulatory sequences that direct high level expression of foreign proteins are well known to those skilled in the art. Any of these could be used to construct chimeric genes for production of the any of the gene products of the instant ORF's. These chimeric genes could then be introduced into appropriate microorganisms via transformation to provide high level expression of the enzymes.

Figure 2:
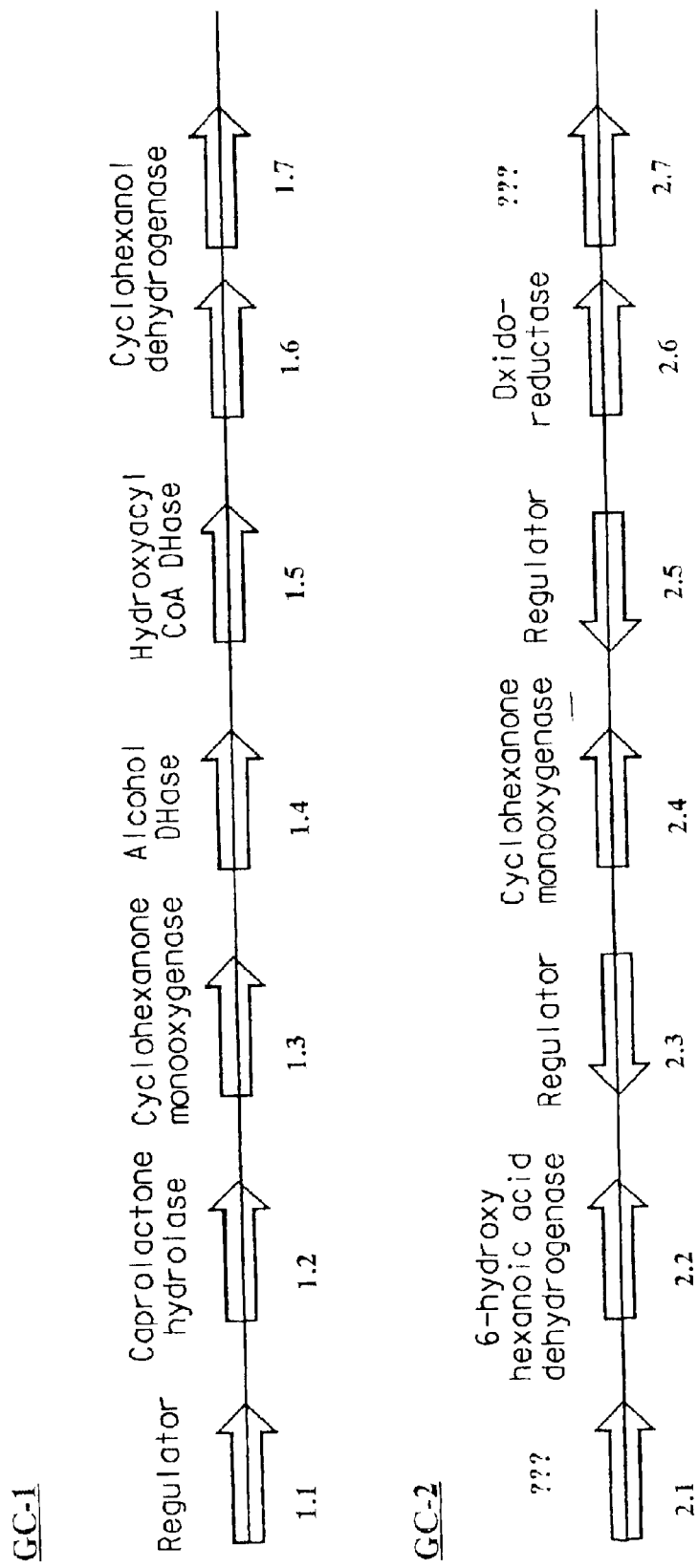
FIG. 2 is a diagram showing the organization of the two gene clusters containing ORF's relevant in the adipic acid biosynthetic pathway.

Additionally, chimeric genes will be effective in altering the properties of the host bacteria. It is expected, for example, that introduction of chimeric genes encoding one or more of the ORF's 1.2, 1.3, 1.4, 1.6, 1.7, 2.2 and 2.4 under the control of the appropriate promoters, into a host cell comprising at least one copy of these genes will demonstrate the ability to produce various intermediates in the adipic acid biosynthetic pathway. For example, the appropriately regulated ORF 1.2, would be expected to express an enzyme capable of converting ε-caprolactone to 6-hydroxy hexanoic acid (FIG. 1). Similarly, ORF 2.2 or ORF 1.4 would be expected to express an enzyme capable of converting 6-hydroxy hexanoic acid to 6-aldehyde hexanoic acid (FIG. 1). Additionally ORF 1.6 or ORF 1.7 would, be expected to express an enzyme capable of converting cyclohexanol to cyclohexanone (FIG. 1). Finally, expression of both GC-1 (SEQ ID NO:15) or GC-2 (SEQ ID NO:16) in a single recombinant organism will be expected to effect the conversion of cyclohexanol to adipic acid in a transformed host (FIG. 2).

ORF 1.3 or ORF 2.4 encode the Brevibacterium sp HCU monooxygenase. Applicant has demonstrated that this monooxygenase, although useful for the conversion of cyclohexanone to ε-caprolactone, has substrate specificity for a variety of other single ring compounds, including, but not limited to cyclobutanone, cyclopentanone, 2-methylcyclopentanone, 2-methylcyclo-hexanone, cyclohex-2-ene-1-one, 2-(cyclohex-1-enyl)cyclohexanone, 1,2-cyclohexanedione, 1,3-cyclohexanedione, and 1,4-cyclohexanedione (see Table 2). It is contemplated that the instant monooxygenases would be useful in the bioconversion of any molecule containing a complete oxidized or derivatized cyclohexanone substructure, such as for example progesterone or 2-amino hydroxycaproate.

It is further contemplated that the open reading frames showing high homology to bacterial regulatory elements may in fact be useful in constructing various expression vectors. For example, ORF's 1.1 and 2.3 each appear to encode a transcriptional regulator. It is contemplated that these ORF's may be used in regulatable expression vectors for for HiGC Gram positive bacteria (a group including, but not limited to, the genera Brevibacterium, Corynebacterium, Mycobacterium, Rhodococcus, Arthrobacter, Nocardia, Streptomyces, Actinomyces). For example, such vectors may include the gene encoding the transcription regulator (whether repressor or activator) as well as promoter derived from the upstream sequence of GC-1 or GC-2. Induction of transcription of genes cloned downstream of the promoter sequence would be induced by the addition in the growth medium of the molecule that induces either cluster. Likely inducers of GC-1 or GC-2 expression would be cyclohexanol or cyclohexanone or products of their oxidation.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters, which are useful to drive expression of the instant ORF's in the desired host cell are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI (useful for expression in Saccharomyces); AOX1 (useful for expression in Pichia); and lac, trp, $1P_L$, $1P_R$, T7, tac, and trc (useful for expression in *Escherichia coli*).

Termination control regions may also be derived from various genes native to the preferred hosts. Optionally, a termination site may be unnecessary, however, it is most preferred if included.

Description of the Preferred Embodiments

The present invention relates to the isolation of genes encoding enzymes useful for the conversion of cyclohexanol to adipic acid, and for the production of enzymatic intermediates in the adipic acid biosynthetic pathway. The relevant genes were isolated from a Brevibacterium sp. which was cultured from an industrial waste stream. Colonies that had the ability to grow on halophilic minimal medium in the presence of cyclohexanone were selected for further study. Taxonomic identification of the Brevibacterium sp HCU was accomplished on the basis of 16s rDNA analysis. Using RT-PCR, two gene clusters (GC-1 and GC-2) were identified and cloned. All open reading frames (ORF's) residing on both gene clusters were sequenced. The organization of the ORF's as well as the putative identification of gene function is shown in FIG. 2. The ORF's encoding two cyclohexanone monooxygenases were cloned into expression hosts and expression of the genes was confirmed on the basis of gel electrophoresis. GC-MS analysis confirmed the activity of the expressed Cyclohexanone monoooxygenase proteins in vitro as well as expressed in the E. coli host.

In similar fashion, ORF's 2.2 and 1.4 were isolated and cloned into an E. coli expression host for expressions studies. GC MS analysis confirmed that 6-hydroxy hexanoic promotes the reduction of NAD into NADH, suggesting that both transformants obtained the ability to convert 6-hydroxy hexanoic acid to the corresponding aldehyde. This data provided evidence that ORF's 2.2 and 1.4 encode a 6-hydroxy hexanoic acid dehydrogenase activity.

The method for the identification of GC-1 and GC-2 as well as the relevant open reading frames is a modified RT-PCT protocol, and is based on the concept of mRNA differential display (McClelland et al., U.S. Pat. No. 5,487,985; Liang, et al., Nucleic Acids Res. (1994), 22(25), 5763–4; Liang et al., Nucleic Acids Res. (1993), 21(14), 3269–75; Welsh et al., Nucleic Acids Res. (1992), 20 (19), 4965–70). The method was particularly adaptable to the instant isolation of the monooxygenase genes as it relies on the inducibility of the gene or pathway message.

The instant method is a technique that compares the mRNAs sampled by arbitrary RT-PCR amplification between control and induced cells. For the analysis of bacterial genomes, typically only a small set of primers is used to generate many bands which are then analyzed by long high resolution sequencing gels. Applicant has modified this approach using a larger set of about 81 primers analyzed on relatively short polyacrylamide urea gels (15 cm long and 1.5 mm thick). Due to their thickness and small length these gels do not have the resolution of sequencing gels and faint bands are difficult to detect. Each primer generates a RAPD pattern of an average of ten DNA fragments. Theoretically, a set of 81 primers should generate about 800 independent bands.

The basic protocol involves 6 steps which follow growth of the cells and total RNA extraction. The steps are: (i) arbitrarily primed reverse transcription and PCR amplification, (ii) separation and visualization of PCR products, (iii) elution, reamplification and cloning of differentially expressed DNA fragments, (iv) sequencing of clones (v) assembly of clones in contigs and sequence analysis; and (vi) identification of induced metabolic pathways Arbitrarily primed reverse transcription and PCR amplification were performed with the commercial enzyme kit from Gibco-BRL "Superscript One-Step RT-PCR System" which provides buffers, the reverse transcriptase and the Taq polymerase in a single tube. The reaction mix contains 0.4 mM of each dNTP and 2.4 mM MgSO$_4$ in addition to other components.

The primers used were a collection of 81 primers with the sequence 5'-CGGAGCAGATCGAVVVV(SEQ ID NO:38) where VVVV represent all the combinations of the three bases A, G and C at the last four positions of the 3'-end. The 5' end sequence was designed as to have minimal homology towards both orientations of the 16S rDNA sequences from many organisms with widespread phylogenetic position in order to minimize non specific amplification of these abundant and stable RNA species.

The 81 primers were pre-aliquoted on five 96 well PCR plates. In each plate, each primer was placed in two adjacent positions as indicated below.

| A1 | A1 | A2 | A2 | A3 | A3 | A4 | A4 | A5 | A5 | A6 | A6 |
|----|----|----|----|----|----|----|----|----|----|----|----|
| A7 | A7 | A8 | A8 | A9 | A9 | A10 | A10 | A11 | A11 | A12 | A12 |
| A13 | A13 | A14 | A14 | A15 | A15 | A16 | A16 | A17 | A17 | A18 | A18 |
| A19 | A19 | A20 | A20 | A21 | A21 | A22 | A22 | A23 | A23 | A24 | A24 |
| A25 | A25 | A26 | A26 | A27 | A27 | A28 | A28 | A29 | A29 | A30 | A30 |
| A31 | A31 | A32 | A32 | A33 | A33 | A34 | A34 | A35 | A35 | A36 | A36 |
| A37 | A37 | A38 | A38 | A39 | A39 | A40 | A40 | A41 | A41 | A42 | A42 |
| A43 | A43 | A44 | A44 | A45 | A45 | A46 | A46 | A47 | A47 | A48 | A48 |

Typical RT-PCT was then performed using standard protocols well known in the art.

Separation and visualization of PCR products was carried out as follows: 5 μl out each 25 μl RT-PCR reaction were analyzed on precuts acrylamide gels (Excell gels Pharmacia Biotech). PCR products from control and Induced RNA generated from the same primers were analyzed side by side. The gels were stained with the Plus One DNA silver staining Kit (Pharmacia Biotech) to visualized the PCR Fragments then rinsed extensively with distilled water for one hour to remove the acetic acid used in the last step of the staining procedure. DNA fragments from control and induced lanes generated from the same primers were compared. Bands present in the induced lane but not in the control lane were excised with a scalpel.

Elution, reamplification and cloning of differentially expressed DNA fragments was carried out as follows. Each band excised from the gel was placed in a tube containing 50 μl of 10 mM KCl and 10 mM Tris-HCl pH 8.3 and heated to 95° C. for 1 hr to allow some of DNA to diffuse out of the gel. Serial dilutions of the eluate (1/10) were used as template for a new PCR reaction using the following reactions: Mg Acetate (4 mM), dNTPs (0.2 μM), Taq polymerase buffer (Perkin Elmer), oligonucleotide primer (0.2 μM). The primer used for each reamplification was the one that had generated the DNA pattern.

Each reamplified fragment was cloned into the blue/white cloning vector pCR2.1-Topo (Invitrogen).

Four to eight clones from the cloning of each differentially expressed band were submitted to sequencing using the universal forward. Inserts that did not yield a complete sequence where sequenced on the other strand with the reverse universal primer.

The nucleotide sequences obtained where trimmed for vector, primer and low quality sequences, and aligned using the Sequencher program (Gene Code Corporation). The sequences of the assembled contigs were then compared to protein and nucleic acid sequence databases using the BLAST alignment program (BLAST Manual, Altschul et al., Natl. Cent. Biotechnol. Inf:, Natl. Library Med. (NCBI NLM) NIH, Bethesda, Md. 20894; Altschul et al., J. Mol. Biol. 215:403–410 (1990)).

Once all contigs were assembled, the number of bands having yielded clones included in the contig was plotted. Many contigs were composed of the sequence of distinct identical clones from the cloning of a single band. Such contigs may represent false positives, i.e., PCR bands not really differentially expressed. In other cases the PCR bands may represent genes actually induced but having been sampled by only one primer in the experiment. Some contigs were generated from the alignment of DNA sequences from bands amplified by distinct primers.

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

EXAMPLES

General Methods

Procedures for phosphorylations, ligations and transformations are well known in the art. Techniques suitable for use in the following examples may be found in Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis").

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

The meaning of abbreviations is as follows: "h" means hour(s), "min" means minute(s), "sec" means second(s), "d" means day(s), "mL" means milliliters, "L" means liters.

Bacterial Strains and Plasmids:

Brevibacterium sp HCU was isolated from enrichment of activated sludge obtained from an industrial wastewater treatment facility. Max Efficiency competent cells of *E. coli* DH5α and DH10B were purchased from GIBCO/BRL (Gaithersburg, Md.). Expression plasmid pQE30 were purchased from Qiagen (Valencia, Calif.). Cloning vector pCR2.1 and expression vector p Trc/His2-Topo were purchased from Invitrogen (San Diego, Calif.).

Growth Conditions:

Bacterial cells were usually grown in Luria-Bertani medium containing 1% of bacto-tryptone, 0.5% of bacto-yeast extract and 1% of NaCl unless otherwise indicated below.

Growth substrates for Brevibacterium sp. HCU were added to S12 medium as sole source of carbon to the concentration of 100 ppm.

| | |
|---|---|
| Yeast Extract | +++ |
| Casaminoacids | +++ |
| Glucose | + |
| Fructose | ++ |

-continued

| | |
|---|---|
| Maltose | − |
| Sucrose | − |
| Methanol | − |
| Ethanol | ++ |
| 1-Propanol | ++ |
| 2-Propanol | − |
| 1-Butanol | ++ |
| Glycerol | ++ |
| Acetate | +++ |
| Propionate | +++ |
| Butyrate | +++ |
| Lactate | +++ |
| Succinate | ++ |
| Decanoate | + |
| Decane | − |
| Hexadecane | − |
| Phenol | − |
| Benzene | − |
| Benzoate | − |
| Toluene | − |
| Cyclohexane | − |
| Cyclohexanone | ++ |
| Cyclohexanol | + |
| Cyclopentanone | + |
| Cycloheptanone | − |
| Cycloheptanol | − |
| Cyclooctanone | − |
| Cyclododecanone | − |

Enzymatic Assays

The cyclohexanone monooxygenase activity of each over-expressed enzyme was assayed spectrophotometrically at 340 nm by monitoring the oxidation of NADPH. In a spectrophotometer cuvette containing 50 mM Tris-HCl, 50 mM K Acetate pH7 at 30° C. NADPH 0.3 mM and 20–50 µg of homogenous monooxygenase the reaction was initiated by the addition of 1 mM of cyclohexanone. Substrate specificity of each enzyme was tested with other cyclic ketones added at 0.1 or 0.5 mM.

Confirmation of the oxidation of cyclohexanone into caprolactone was determined by GC-Mass Spectrometry on a HP 5890 Gas Chromatograph with HP 5971 mass selective detector equipped with a HP-1 capillary column (Hewlett Packard). Prior to analysis, samples were acidified to pH 3 by HCl, extracted by dichloromethane three times, dried with MgSO4 and filtered.

Example 1

Isolation of a Cyclohexanone Degrading Brevibacterium sp. HCU

Selection for a halotolerant bacterium degrading cyclohexanol and cyclohexanone was performed on agar plates of a halophilic minimal medium (Per 1: Agar 15 g, NaCl 100 g, MgSO4 10 g, KCl 2 g, NH4Cl 1 g, KH2PO4 50 mg, FeSO4 2 mg, Tris HCl 8 g, pH 7) containing traces of yeast extract and casaminoacids (0.005% each) and incubated under vapors of cyclohexanone at 30° C. The inoculum was a resuspension of sludge from industrial wastewater treatment plant. After two weeks, beige colonies were observed and streaked to purity on the same plates under the same conditions.

Taxonomic identification was performed by PCR amplification of 16S rDNA using primers corresponding to conserved regions of the 16S rDNA molecule (Amann).

These primers were:

| | |
|---|---|
| 5'-GAGTTTGATCCTGGCTCAG-3' | SEQ ID NO:28 |
| 5'-CAGG(A/C)GCCGCGGTAAT(A/T)C-3' | SEQ ID NO:29 |
| 5'-GCTGCCTCCCGTAGGAGT-3' | SEQ ID NO:30 |
| 5'-CTACCAGGGTAACTAATCC-3' | SEQ ID NO:31 |
| 5'-ACGGGCGGTGTGTAC-3' | SEQ ID NO:32 |
| 5'-CACGAGCTGACGACAGCCAT-3' | SEQ ID NO:33 |
| 5'-TACCTTGTTACGACTT-3' | SEQ ID NO:34 |
| 5'-G(A/T)ATTACCGCGGC(G/T)GCTG-3' | SEQ ID NO:35 |
| 5'-GGATTAGATACCCTGGTAG-3' | SEQ ID NO:36 |
| 5'-ATGGCTGTCGTCAGCTCGTG-3' | SEQ ID NO:37 |

The complete 16s DNA sequence of the isolated Brevibacterium sp. HCU was found to be unique and is shown as SEQ ID NO:49.

Induction of the Cyclohexanone Degradation Pathway

Inducibility of the cyclohexanone pathway was tested by respirometry in low salt medium. One colony of strain HCU was inoculated in 300 ml of S12 mineral medium (50 mM KHPO$_4$ buffer (pH 7.0), 10 mM (NH4)$_2$SO$_4$, 2 mM MgCl$_2$, 0.7 mM CaCl$_2$, 50 uM MnCl$_2$, 1 μM FeCl$_3$, 1 μM ZnCl$_3$, 1.72 μM CuSO$_4$, 2.53 μM CoCl$_2$, 2.42 μM Na$_2$MoO$_2$, and 0.0001% FeSO$_4$) containing 0.005% yeast extract. The culture was then split in two flasks which received respectively 10 mM Acetate and 10 mM cyclohexanone. Each flask was incubated for six hrs at 30° C. to allow for the induction of the cyclohexanone degradation genes. The cultures were then chilled on iced, harvested by centrifugation and washed three times with ice cold S12 medium lacking traces of yeast extract. Cells were finally resuspended to an absorption of 2.0 at 600 nm and kept on ice until assayed.

Half a ml of each culture was placed in a water jacketed respirometry cell equipped with an oxygen electrode (Yellow Spring Instruments Co., Yellow spring, Ohio) and containing 5 ml of air saturated S12 medium at 30° C. After establishing the baseline respiration for each of the cell suspensions, acetate or cyclohexanone were added to a final concentration of 0.02% and the rate of O$_2$ consumption was further monitored.

Example 2

Identification of Genes Involved in the Oxidation of Cyclohexanone

Identification of genes involved in the oxidation of cyclohexanone made use of the fact that this oxidation pathway is inducible. The mRNA populations of a control culture and a cyclohexanone-induced culture were compared using a technique based on the random amplification of DNA fragments by reverse transcription followed by PCR.

Isolation of Total Cellular RNA

The cyclohexanone oxidation pathway was induced by addition of 0.1% cyclohexanone in one of two "split" cultures of Brevibacterium HCU grown as described in the GENERAL METHODS. Each 10 ml culture was chilled rapidly in an ice/water bath and transferred to a 15 ml tube. Cells were collected by centrifugation for 2 min. at 12,000×g in a rotor chilled to −4° C. The supernatants were discarded, the pellets resuspended in 0.7 ml of ice cold solution of 1% SDS and 100 mM Na acetate at pH 5 and transferred to a 2 ml tube containing 0.7 ml of aqueous phenol pH 5 and 0.3 ml of 0.5 mm zirconia beads (Biospec Products, Bartlesville, Okla.). The tubes were placed in a bead beater (Biospec Products, Bartlesville, Okla.) and disrupted at 2400 beats per min. for two min.

Following the disruption of the cells, the liquid phases of the tubes were transferred to new microfuge tubes and the phases separated by centrifugation for 3 min. at 15,000×g. The aqueous phase containing total RNA was extracted twice more with phenol at pH 5 and twice with a mixture of phenol/chloroform/isoamyl alcohol pH 7.5 until a precipitate was no longer visible at the phenol/water interface. Nucleic acids were then recovered from the aqueous phase by ethanol precipitation with three volumes of ethanol and the pellet resuspended in 0.5 ml of diethyl pyrocarbonate (DEPC) treated water. DNA was digested by 6 units of RNAse-free DNAse (Boehringer Mannheim, Indianapolis, Ind.) for 1 hr at 37° C. The total RNA solution was then extracted twice with phenol/chloroform/isoamyl alcohol pH 7.5, recovered by ethanol precipitation and resuspended in 1 ml of DEPC treated water to an approximate concentration of 0.5 mg per ml.

RT-PCR Oligonucleotide Set

A set of 81 primers was designed with the sequence CGGAGCAGATCGAVVVV (SEQ ID NO:38) where VVVV represent all the combinations of the three bases A, G and C at the last four positions of the 3'-end.

Generation of RAPDs Patterns From Arbitrarily Reverse-Transcribed Total RNA

Arbitrarily amplified DNA fragments were generated from the total RNA of control and induced cells by following the protocol described by Wong K. K. et al., (*Proc Natl Acad Sci USA*. 91:639 (1994)). A series of parallel reverse transcription/PCR amplification experiments each using one oligonucleotide per reaction were performed on the total RNA from the control and induced cells. Briefly, 50 μl reverse transcription reactions were performed on 20–100 ng of total RNA using the 100 u Moloney Murine Leukemia Virus (MMLV) reverse transcriptase (Promega, Madison, Wis.) with 0.5 mM of each dNTP and 1 mM for each oligonucleotide primer. Reactions were prepared on ice and incubated at 37° C. for 1 hr.

Five μl from each RT reaction were then used as template in a 50 μl PCR reaction containing the same primer used for the RT reaction (0.25 μM), dNTPs (0.2 mM each), Mg Acetate (4 mM) and 2.5 u of the Taq DNA polymerase Stoffel fragment (Perkin Elmer, Foster City, Calif.). The following temperature program was used: 94° C. (5 min.), 40° C. (5 min.), 72° C. (5 min.) for I cycle followed by 40 cycles of: 94° C. (1 min.), 60° C. (1 min.), 72° C. (5 min.).

RAPD fragments were separated by electrophoresis on acrylamide gels (15 cm×15 cm×1.5 mm, 6% acrylamide, 29/1 acryl/bisacrylamide, 100 mM Tris, 90 mM borate, 1 mM EDTA pH 8.3). Five μl from each PCR reaction were analyzed, running side by side the reactions from the control and the induced RNA for each primer. Electrophoresis was performed at 1 V/cm. DNA fragment were visualized by silver staining using the Plus One® DNA silver staining kit in the Hoefer automated gel stainer (Amersham Pharmacia Biotech, Piscataway, N.J.)

Reamplification of the Differentially Expressed DNA

Stained gels were rinsed extensively for one hr with distilled water. Bands generated from the RNA of cyclohexanone induced cells but absent in the reaction from the RNA of control cells were excised from the gel and placed in a tube containing 50 μl of 10 mM KCl and 10 mM Tris-HCl pH 8.3 and heated to 95° C. for 1 hr to allow some of the DNA to diffuse out of the gel. Serial dilutions of the eluate over a 200 fold range were used as template for a new PCR reaction using the taq polymerase. The primer used for each reamplification (0.25 μM) was the one that had generated the pattern.

Each reamplified fragment was cloned into the blue/white cloning vector pCR2.1 (Invitrogen, San Diego, Calif.) and sequenced using the universal forward and reverse primers.

Example 3

Cloning, Sequencing and Identification of ORF's on GC-1 and GC-2

Kilobase-long DNA fragments extending the sequences fragments identified by differential display were generated by "Out-PCR", a PCR technique using an arbitrary primer in addition to a sequence specific primer.

Genomic DNA was used as template in 10 separate 50 μl PCR reactions using the long range rTth XL DNA polymerase (Perkin-Elmer, Foster City, Calif.) and one of 10 arbitrary primers described above. The reaction included the rTth XL buffer provided by the manufacturer, 1.2 mM Mg Acetate, 0.2 mM of each dNTP, genomic DNA (10–100 ng) and 1 unit of rTth XL repolymerase. Annealing was performed at 45° C. to allow arbitrary priming of the genomic DNA and the DNA replication was extended for 15 min. at 72° C. At that point each reaction was split in two. One of the two tubes was kept unchanged and used as a control while the other tube received a specific primer corresponding to the end sequence of a differentially expressed fragment to be extended and directed towards the outside of the fragment. For example to extend the sequence of the first monooxygenase, two primers were designed one diverging from the 5' end of the differentially displayed fragment #1 (5'-GATCCACCAAGTTCCTCC-3', [SEQ ID NO:39]) and one diverging from 3' end of the differentially displayed fragment #3 (5'-CCCGGTAAATCACGTGAGTACCACG-3', [SEQ ID NO:40]). Thirty additional PCR cycles were performed and the two reactions were analyzed side by side by agarose electrophoresis. For about one fifth of the arbitrary primers used, one or several additional bands were present in the sample having received the specific primer.

These bands were excised from the gel, melted in 0.5 ml H2O and used as template in a set of new PCR reactions that included rTth XL buffer, 1.2 mM Mg Acetate, 0.2 mM of each dNTP, 0.4 μM of primers, 1/1000 dilution of the melted slice 1 μl and 1 unit of rTth XL polymerase.

For each reamplification, two control reactions were performed in order to test that the reamplification of the band of interest. Each reaction omitted either the arbitrary or the specific primer.

The Reaction Components

The DNA fragments that fulfilled that condition were sequenced using the specific primer. The subset of DNA fragment with sequence overlap with the differentially expressed fragment to be extended were further sequenced either by "primer walking" or "shotgun cloning" of a partial MobI digest in pCR2.1 (Invitrogen, San Diego, Calif.).

To rule out the creation of PCR artifacts, overlapping DNA fragments 2–3 kb long were reamplified from chromosomal DNA using primers derived from the assembled sequence.

ORF's contained on GC-1 and GC-2 were identified by conducting BLAST (Basic Local Alignment Search Tool; Altschul, S. F., et al., (1993) *J. Mol. Biol.* 215:403–410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, SWISS-PROT protein sequence database, EMBL, and DDBJ databases). The sequences obtained were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J. (1993) *Nature Genetics* 3:266–272) provided by the NCBI.

The sequence comparisons based on BLASTX analysis against the "nr" database are given below in Table 1 using Xnr BLAST algorithm.

TABLE 1

| ORF | Similarity Identified | SEQ ID base | SEQ ID Peptide | % Identity[a] | % Similarity[b] | E-value[c] | Citation |
|---|---|---|---|---|---|---|---|
| 1.1 | gi\|143969 rteB [*Bacteroides thetaiotaomicron*] | 1 | 2 | 35% | 54% | 9e − 12 | J. Bacteriol. 174, 2935–2942 (1992) |
| 1.2 | emb\|CAB42768.1\| putative esterase [*Streptomyces coelicolor*] | 3 | 4 | 37% | 54% | 8e − 30 | Mol. Microbiol. 21 (1), 77–96 (1996) |
| 1.3 | dbj\|BAA24454.1\| steroid monooxygenase [*Rhodococcus rhodochrous* | 5 | 6 | 44% | 59% | 1e − 123 | J. Biochem. 126 (3) 624–631 (1999) |
| 1.4 | sp\|P31005\| Methanol dehydrogenase. [*Bacillus sp.*] | 7 | 8 | 25% | 44% | 3e − 34 | J. Bacteriol. 174 (16), 5346–5353 (1992) |
| 1.5 | gi\|2649379 3-hydroxyacyl-CoA dehydrogenase [*Archaeoglobus fulgidus*] | 9 | 10 | 27% | 44% | 1e − 25 | Nature 390 (6658), 364–370 (1997) |
| 1.6 | >gb\|AAD35385.1\| oxidoreductase, short chain dehydrogenase/reductase family [*Thermotoga maritima*] | 11 | 12 | 33% | 51% | 9e − 30 | Nature 399, 323–329 (1999) |
| 1.7 | >gb\|AAD36790.1\| 3-oxoacyl-(acyl carrier protein) reductase [*Thermotoga maritima*] | 13 | 14 | 38% | 57% | 6e − 40 | Nature 399, 323–329 (1999) |

TABLE 1-continued

| ORF | Similarity Identified | SEQ ID base | SEQ ID Peptide | % Identity[a] | % Similarity[b] | E-value[c] | Citation |
|---|---|---|---|---|---|---|---|
| 2.1 | No homology identified | | | | | | |
| 2.2 | sp|P50381| alcohol dehydrogenase [*Sulfolobus sp.*] | 17 | 18 | 30% | 47% | 1e − 37 | J. Bacteriol. 178 (1), 301–305 (1996) |
| 2.3 | >emb|CAB53399.1| putative transcriptional regulator [*Streptomyces coelicolor* A3(2)] | 19 | 20 | 32% | 46% | 3e − 21 | Mol. Microbiol. 21 (1), 77–96 (1996) |
| 2.4 | |PID|d1025370 Steroid monooxygenase [*Rhodococcus rhodochrous*] | 21 | 22 | 38% | 53% | 2e − 95 | J. Biochem. 126 (3), 624–631 (1999) |
| 2.5 | >pir||A29606 Member of the ArsR family of transcriptional regulators [*Streptomyces coelicolor*] | 23 | 24 | 51% | 64% | 9e − 18 | Gene 58:229–41 (1987) |
| 2.6 | >gb|AAF11740.1|NADH-dependent oxidoreductase, putative [*Deinococcus radiodurans*] | 25 | 26 | 50% | 61% | 2e − 76 | Science 286, 1571–1577 (1999) |
| 2.7 | No Homology identified | 27 | | | | | |

[a] %Identity is defined as percentage of amino acids that are identical between the two proteins.
[b] % Similarity is defined as percentage of amino acids that are identical or conserved between the two proteins.
[c] Expect value. The Expect value estimates the statistical significance of the match, specifying the number of matches, with a given score, that are expected in a search of a database of this size absolutely by chance.

Example 4

Expression of Monooxygenases in *E. coli*

The monooxygenase genes were cloned in the multiple cloning site of the N-terminal His6 expression vector pQE30 (Qiagen). Each gene was amplified by PCR from chromosomal DNA using primers corresponding to the ends of the gene and engineered to introduce a restriction site (underlined) not present in the gene. The oligonucleotides 5'-GAAAGATCGAGGATCCATGCCAATTACACAAC-3' (SEQ ID NO:41) and 5'-TCGAGCAAGCTTGGCTGCAA-3' (SEQ ID NO:42) were used for the cluster 1 monooxygenase gene and 5'-TCGAAGGAGGAGGC-ATGCATGACGTCAACC-3' (SEQ ID NO:43) and 5'-CAGCAGGGACAAGCTTAGACTCGACA-3' (SEQ ID NO:44) for the cluster 2 monooxygenase gene.

The resulting plasmids (pPCB1 and pPCB2) were introduced into *E. coli* strain DH10B containing a pACYC 184 (tet[R]) derivative with the lacIQ gene cloned in the EcoRI site of the chloramphenicol acetyl transferase gene to provide a tighter repression of the gene to be expressed.

Figure 3:
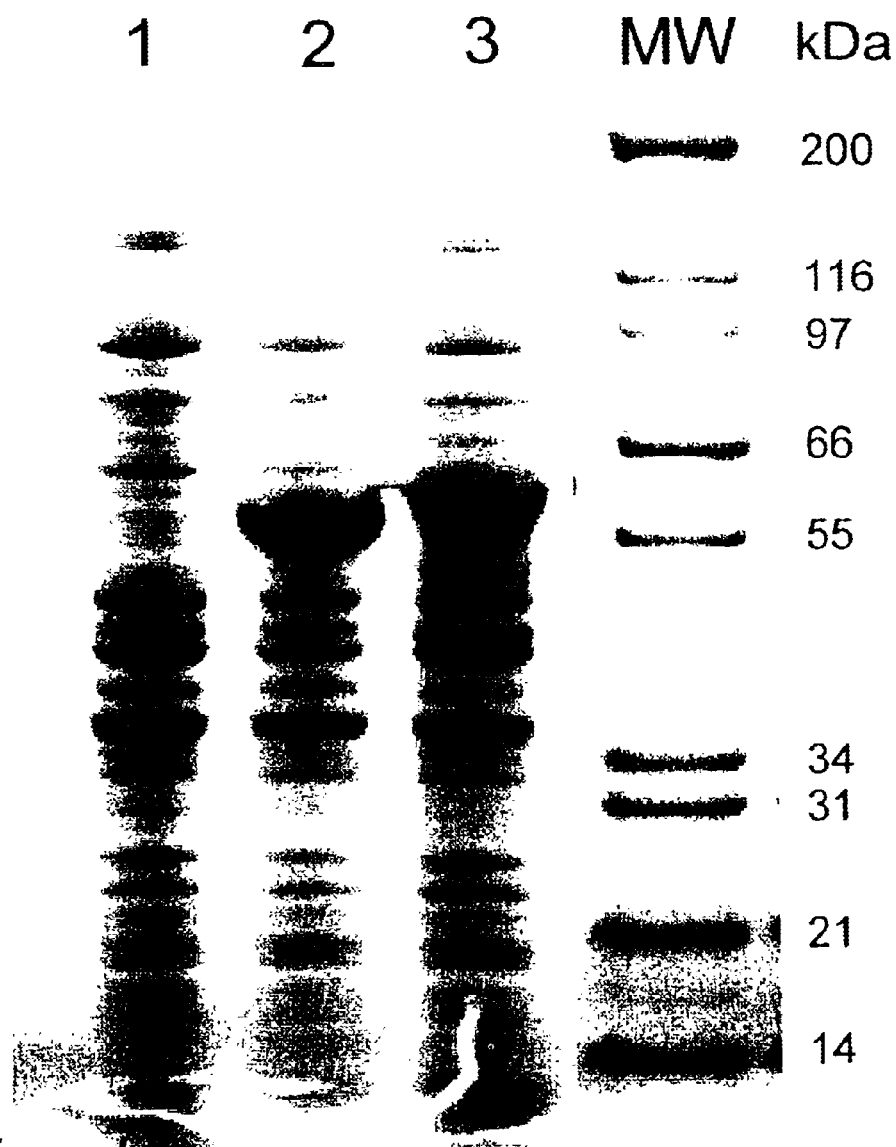
FIG. 3 is a digitized image of an acrylamide gel showing the purification of two Brevibacterium monooxygenases expressed in *E. coli*.

Expression of the His6-tagged proteins was done by growing the cells carrying the expression plasmids in 1 l of Luria-Bertani broth (Miller 1972) containing Ampicillin (100 μg/ml) and tetracyclin (10 μg/ml) at 28° C. Riboflavin (1 μg/ml) was also added to the medium since both monooxygenases are flavoproteins. When the absortion reached 0.5 at 600 nm, 1 mM isopropy-thio-b-galactoside (IPTG) was added to the culture. Cells were harvested 1.5 hr later, resuspended in 2 ml of 300 mM NaCl 5% glycerol 20 mM Tris-HCl pH 8.0 (Buffer A) containing 10 mM EDTA and 100 μg lysozyme and disrupted by three freeze/thaw cycles. Nucleic acids were digested by addition of MgCl2 (20 mM) RNAseA and DNAse I (10 μg each). The particulate fraction was removed by centrifugation at 14,000 RPM and the supernatant was mixed for 1 hr at 4° C. with 100 μl of a metal chelation agarose (Ni-NTA Superflow Qiagen, Valencia, Calif.) saturated with Ni(II) and equilibrated Buffer A containing 5 mM imidazole. The resin was washed bathchwise with 10 ml each of Buffer A containing 5, 10, 15, 20, 40, 80, 150 and 300 mM respectively. The bound proteins were eluted between 80 and 150 mM imidazole. Eluted proteins were concentrated by ultrafiltration with a Centricon device (cut off 10,000 Da, Amicon) and the buffer replaced by Buffer A. Homogeneity of the overexpressed proteins is shown in FIG. 3, which show a gel electrophoresis separation of proteins from control *E. coli* (lane 1), *E. coli* expressing ORF 1.3 (lane 2) and *E. coli* expressing ORF 2.4 (lane 3).

Figure 4:
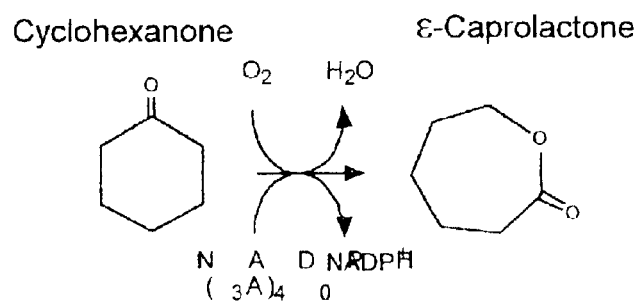
FIG. 4 is a plot of the spectrophotometric assay of the oxidation of cyclohexanone by one of monooxygenase 1.
Figure 4:
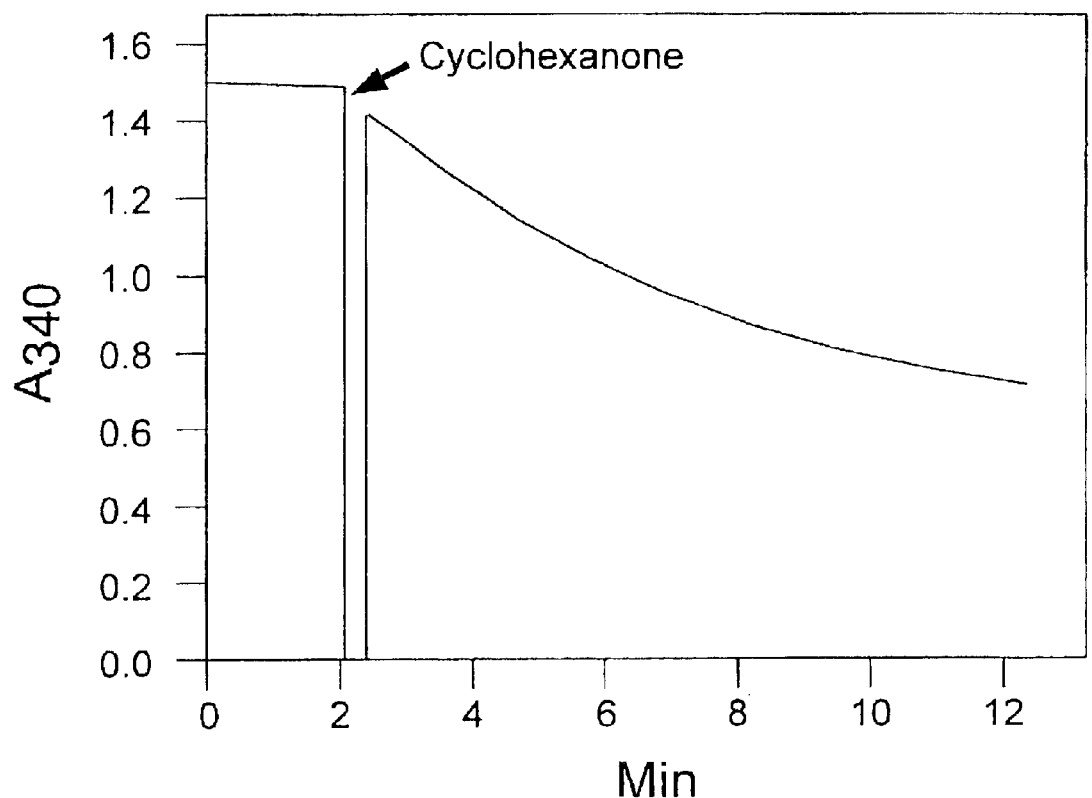

Each monooxygenase oxidized cyclohexanone as measured spectrophoto-metrically by monitoring the oxidation of NADPH at 340 nm. For example, monooxygenase activity from the expression of ORF 1.3 is shown in FIG. 4. No activity was observed when NADPH was replaced by NADH. The product of the cyclohexanone oxidation was confirmed to be caprolactone by GC-MS analysis. Monooxygenase 1 and 2 have different substrate specificity relative to the number of carbon atoms, the oxidation or the substitution of the ring. The specificity of each enzyme for various cyclic ketones is shown in Table 2.

TABLE 2

| SUBSTRATE | CONC'N | Mono 1 rate (min-1) | Mono 2 rate (min-1) |
|---|---|---|---|
| 1. cyclobutanone | 0.1 mM | 235 | 92 |
| | 0.5 mM | 171 | 96 |
| 2. cyclopentanone | 0.1 mM | 1.2 | 90 |
| | 0.5 mM | 7.0 | 120 |
| 3. 2-methylcyclopentanone | 0.1 mM | 40 | 120 |
| | 0.5 mM | 110 | 110 |
| 4. cyclohexanone | 0.1 mM | 160 | 100 |
| | 0.5 mM | 290 | 100 |
| 5. 2-methylcyclohexanone | 0.1 mM | 250 | 37 |
| | 0.5 mM | 260 | 97 |
| 6. cyclohex-2-ene-1-one | 0.1 mM | 2.3 | 64 |
| | 0.5 mM | 1.9 | 80 |
| 7. 2-(cyclohex-1-enyl)cyclohexanone | 0.1 mM | 160 | |
| | 0.5 mM | 260 | 2.4 |
| 8. 1,2-cyclohexanedione | 0.1 mM | 9 | 7.6 |
| | 0.5 mM | 52 | 34 |
| 9. 1,3-cyclohexanedione | 0.1 mM | 0.3 | 18 |
| | 0.5 mM | 1.2 | 60 |
| 10. 1,4-cyclohexanedione | 0.1 mM | 130 | 53 |
| | 0.5 mM | 210 | 88 |

TABLE 2-continued

| SUBSTRATE | CONC'N | Mono 1 rate (min-1) | Mono 2 rate (min-1) |
|---|---|---|---|
| 11. cycloheptanone | 0.1 mM | 4.5 | 3.9 |
| | 0.5 mM | 18 | 8.6 |
| 12. cyclooctanone | 0.1 mM | 0.9 | 1.3 |
| | 0.5 mM | 0.4 | 1.3 |
| 13. cyclodecanone | 0.1 mM | | 1.8 |
| | 0.5 mM | 1 | 1.2 |
| 14. cycloundecanone | 0.1 mM | 1.2 | 0.6 |
| | 0.5 mM | 1.4 | 0.9 |
| 15. cyclododecanone | 0.1 mM | 1 | 1.2 |
| | 0.5 mM | 0.9 | 1.8 |

Note:
Substrates were tested as provided by the manufacturers and were not further purified.
Activities below 2.0 could reflect contaminants in the preparations which are themselves substrate for the enzyme.

Example 5

Conversion of Cyclohexanone into Caprolactone by Cell Suspentions

Figure 5:
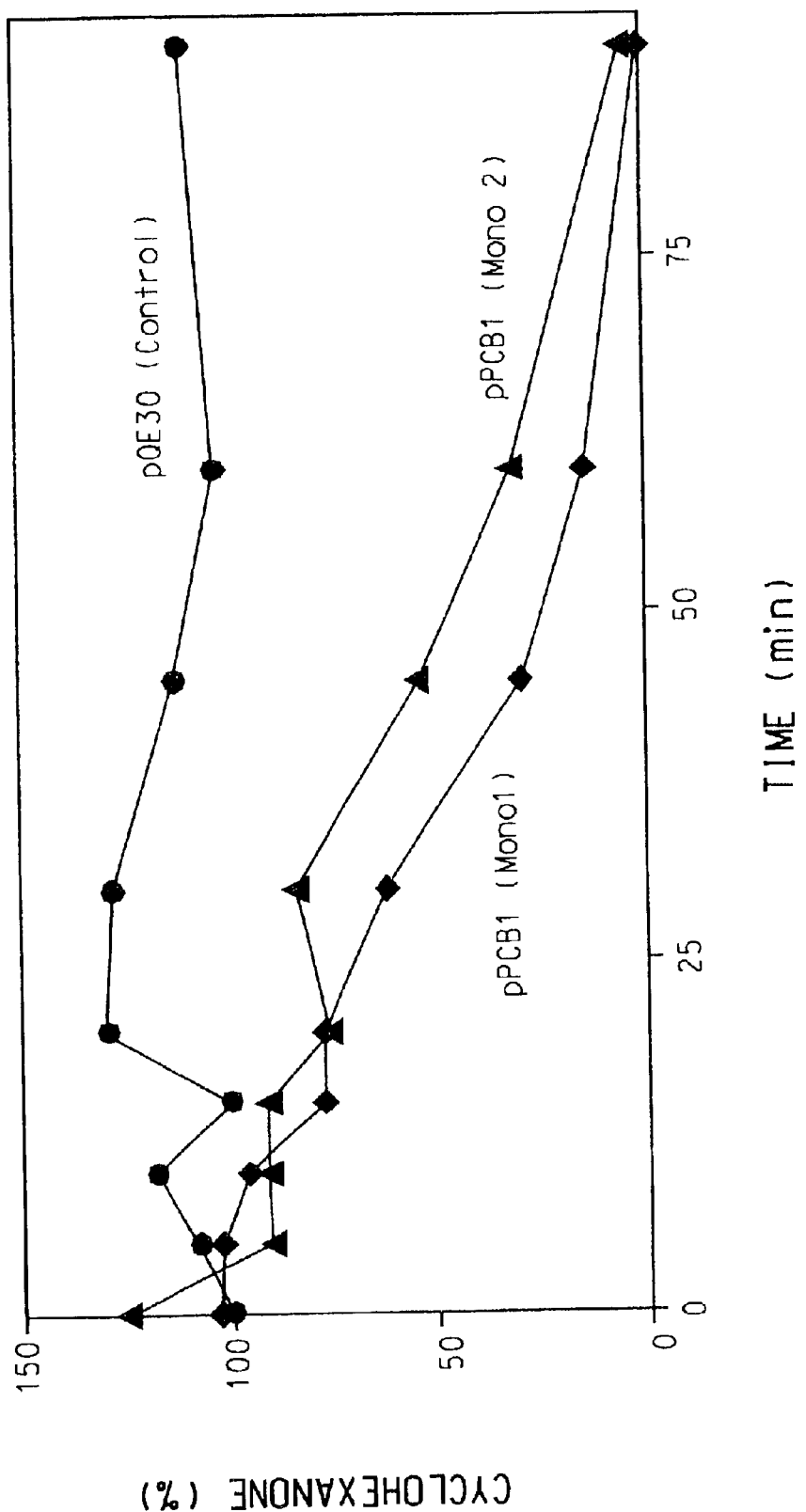
FIG. 5 is a plot showing the timecourse of degradation of cyclohexanone by *E. coli* strains expressing the Brevibacterium monooxygenase 1 or monooxygenase 2.

Twenty ml cultures of *E. coli* strains carrying plasmids pPCB1 and pPCB2 that express the monooxygenase ORF 1.3 and ORF 2.4 respectively were grown at 30° C. in LB medium containing Ampicillin (100 µg/ml) and tetracyclin (10 µg/ml). When the absorbance reached 0.1 at 600 nm, 1 mM IPTG was added to the culture to induce the monooxygenases. After 1 hr, the cultures were chilled and washed twice with M9 mineral medium (Sambrook, J., Fritsch, E. F. and Maniatis, T. *Molecular Cloning: A Laboratory Manual*, Second Edition, Cold Spring Harbor Laboratory Press, Cold Spring Harbor (1989)) and resuspended in 2 ml of the same medium containing 0.2% glucose and 100 ppm of cyclohexanone. After one hr the cells were removed from the culture by centrifugation and supernatant was analyzed by GC-MS as described in the General Methods. The GC-MS analysis indicated the disappearance of cyclohexanone and the appearance of caprolactone. When the rate of cyclohexanone oxidation was plotted as % cyclohexanone remaining vs. time it was seen that all cyclohexanone was oxidized in about 75 min. (FIG. 5).

Example 6

Expression and Activity of Hydroxycaproate Dehydrogenase by *E. coli* Expressing ORF 2.2

ORF 2.2 encoding a member of the long chain Zn-dependent dehydrogenase was amplified by PCR using the primers 5'-ATGAAAGCATTCGCAATGAAGGCA-3' (SEQ ID NO:45) and 5'-CCGCACGGAACCCGTCTCC-3' (SEQ ID NO:48) and cloned in the expression vector pTrc/His-Topo to yield plasmid pPCB7.

*E. coli* strains carrying plasmid pPCB7 that express ORF 2.2 or plasmid pPCB1 that express ORF 1.3, here used as a negative control for dehydrogenase expression, were grown at 25° C. in LB medium containing Ampicillin (100 µg/ml). When the absorbance reached 0.1 at 600 nm, 1 mM IPTG was added to the cultures to induce the dehydrogenase or the monooxygenase 1.

After 3 hr, the cells were harvested, resuspended in 1 ml of 100 mM Tris Buffer pH 8 containing 10 mM EDTA, treated for 30 min with lyzozyme (10 µg/ml) at 0° C. and lysed by three freeze/thaw cycles. Brevibacterium sp. HCU was grown in LB at 30° C. until it reached 1.0 at 600 nm. Cells were harvested, resuspended in S12 medium containing 0.005% yeast extract and 0.1% cyclohexanone and incubated at 30° C. for six hr to induce the cyclohexanone degradation pathway. At that points cells were harvested and lysed by overnight treatment with lyzozyme (100 µg/ml) at 0° C. and freeze thaw cycles. Extracts of the two *E. coli* strains and the Brevibacterium were analyzed at 4° C. by non-denaturing electrophoresis on 12% acrylamide gels (PAGEr™, FMC Rockland, Me.) at 10 V/cm. Protein bands with hydroxycaproate dehydrogenase activity were detected by activity stain using containing 3-(4,5-dimethylthiazolyl)-2,5-diphenyl tetrazolium bromide (MTT) (25 µg/ml), phenazine metosulfate (2.5 µg/ml), NAD (0.15 mM) and hydroxycaproate (1 mM), ammonium sulfate (30 mM) in 100 mM Tris Buffer pH 8.5 (Johnson, E. A. and Lin, E. C., *J. Bacteriol* 169:2050 (1987)). A blue precipitate band indicated the catalysis of NAD reduction by hydroxycaproate and the subsequent reduction of the tetrazolium dye by NADH via the phenazine metosulfate.

Figure 6:
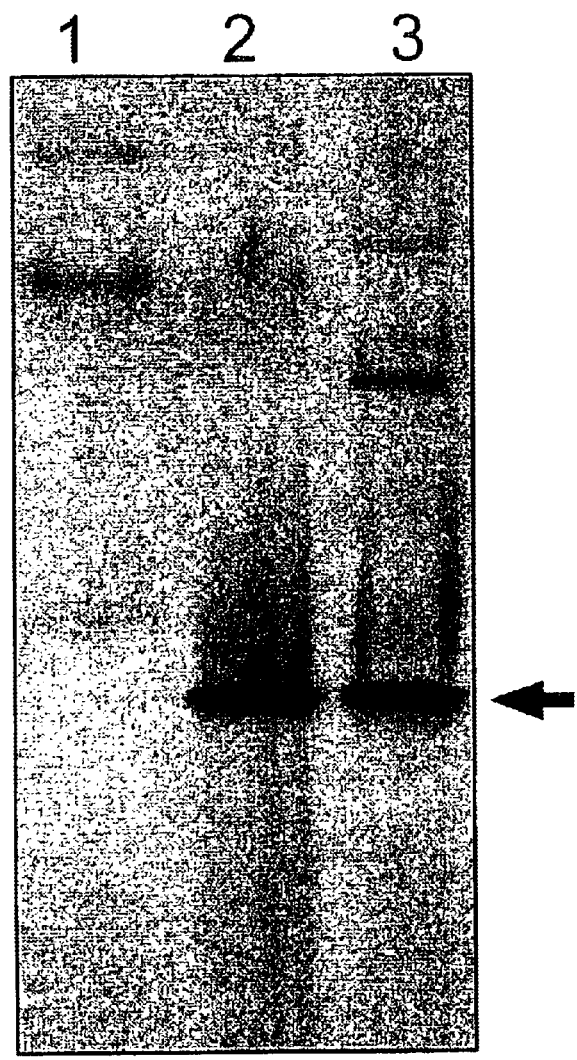
FIG. 6 is a digitized image of the hydroxycaproate dehydrogenase activity stain of an acrylamide gel of cell extract of *E. coli* expressing ORF 2.2.
Figure 7:
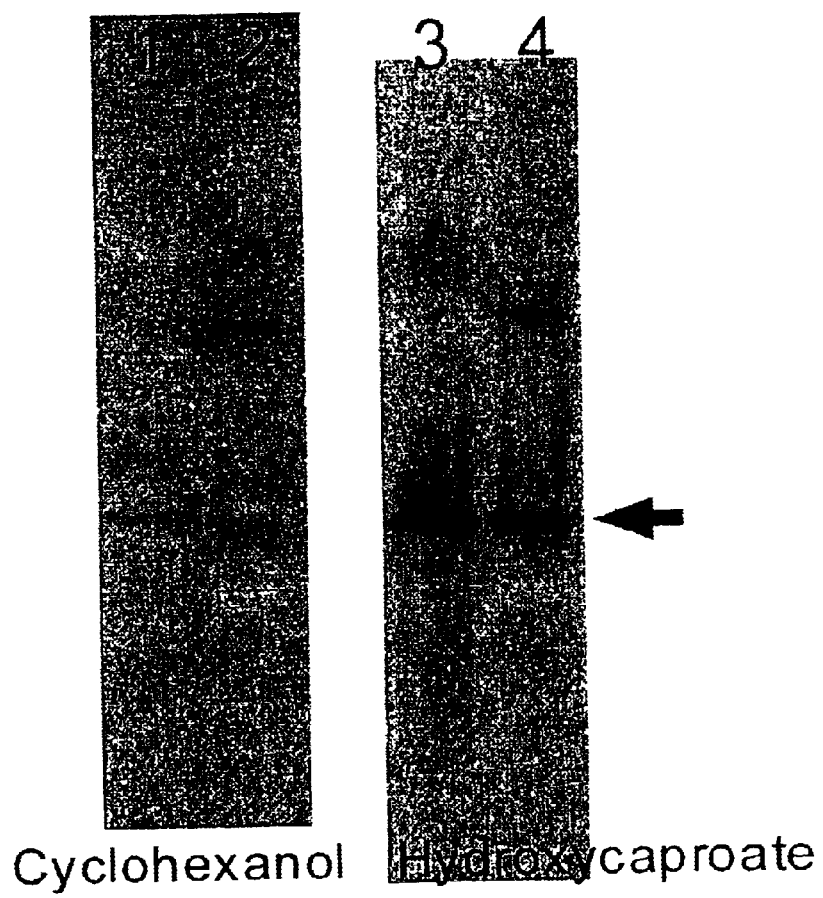
FIG. 7 is a digitized image of the cyclohexanol dehydrogenase activity stain of an acrylamide gel of cell extract of *E. coli* expressing ORF 2.2.

As seen in FIG. 6 (gel electrophoresis protein separation) the *E. coli* strain expressing ORF 2.2 (lane 2) expressed a hydroxycaproate dehydrogenase that comigrated with that of Brevibacterium sp. HCU (lane 3). This band was not observed in the control *E. coli* strain (lane 1). The enzyme expressed by pPCB7, and the commigrating enzyme from Brevibacterium sp. HCU also oxidized cyclohexanol and catalyzed the first step of the oxidation of cyclohexanol into adipic acid as show in FIG. 7. FIG. 7 shows two gel strips illustrating protein separation from *E. coli* expressing ORF 2.2 (lanes 1 and 3) and Brevibacterium HCU (lanes 2 and 4).

Figure 8:
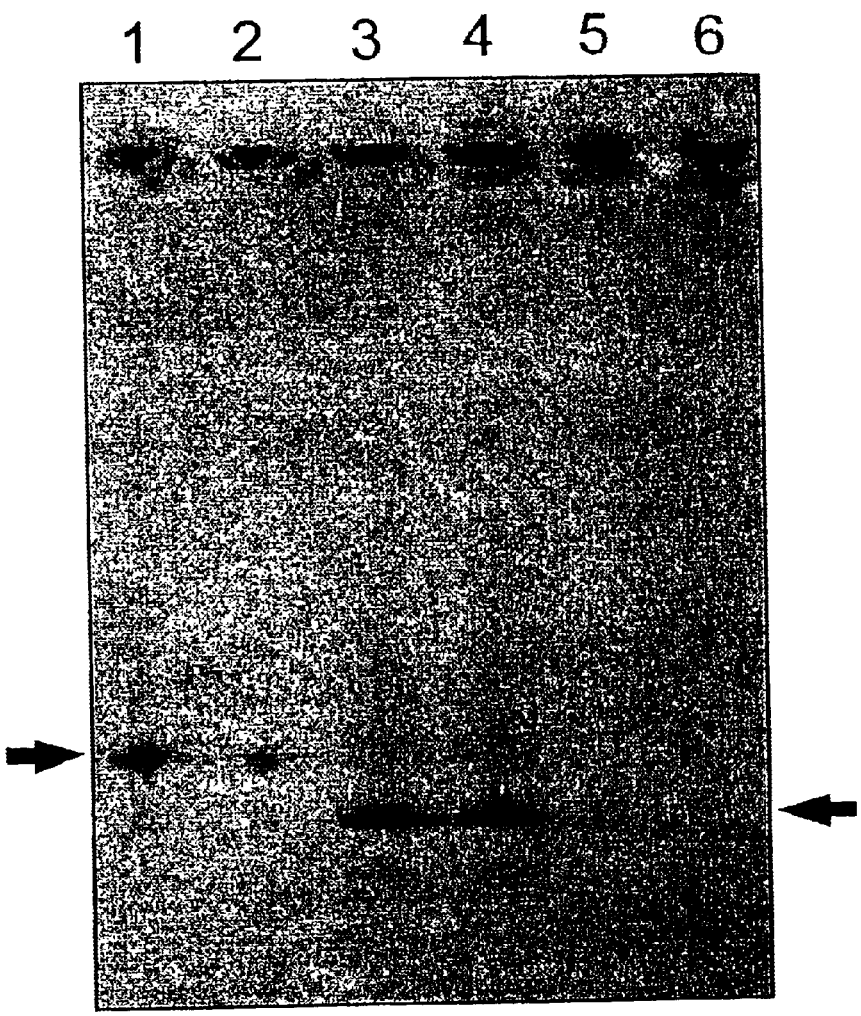
FIG. 8 is a digitized image of the hydroxycaproate dehydrogenase activity stain of an acrylamide gel of cell extract of *E. coli* expressing ORF 1.4

An identical experiment was performed for the Fe-dependent dehydrogenase gene ORF 1.4. It was amplified from chromosomal DNA using the primers 5'-ATGGAGTCGCACAACGAAAACAC-3' (SEQ ID:47) and 5'-GCTCACTCGGCCCACCAGC-3' (SEQ ID:48), cloned in the expression vector pTRc-His2 Topo and expressed in *E. coli*. Cell extracts of *E. coli* cells expressing ORF 1.4 as well as of cells not expressing it were analyzed by acrylimide gel electrophoresis on Phast™ Gels (Pharmacia Biotech, Piscataway, N.J.) and hydroxycaproate dehydrogenase activity was detected by the activity stain described above and shown in FIG. 8. The gel shown in FIG. 8 shows *E. coli* expressing ORF 1.4 (lanes 1, and 2) ORF 2.2 (lanes 3 and 4), the *E. coli* control (lane 5) and *E. coli* expressing ORF 1.3 (lane 6).

What is claimed is:

1. A isolated cyclohexanone monooxygenase polypeptide having an amino acid sequence selected from the group consisting of SEQ ID NO:6 and SEQ ID NO:22.

* * * * *